United States Patent
Ruthenburg et al.

(10) Patent No.: US 11,965,890 B2
(45) Date of Patent: Apr. 23, 2024

(54) COMPOSITIONS AND METHODS FOR QUANTITATIVE ASSESSMENT OF DNA-PROTEIN COMPLEX DENSITY

(71) Applicant: THE UNIVERSITY OF CHICAGO, Chicago, IL (US)

(72) Inventors: Alexander J. Ruthenburg, Chicago, IL (US); Adrian Grzybowski, Chicago, IL (US); Zhonglei Chen, Evanston, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 564 days.

(21) Appl. No.: 16/906,513

(22) Filed: Jun. 19, 2020

(65) Prior Publication Data
US 2020/0319204 A1 Oct. 8, 2020

Related U.S. Application Data

(62) Division of application No. 15/115,081, filed as application No. PCT/US2015/014296 on Feb. 3, 2015, now Pat. No. 10,732,185.

(60) Provisional application No. 61/935,129, filed on Feb. 3, 2014.

(51) Int. Cl.
*C12Q 1/6804* (2018.01)
*C12Q 1/68* (2018.01)
*G01N 33/68* (2006.01)

(52) U.S. Cl.
CPC ........... *G01N 33/6875* (2013.01); *C12Q 1/68* (2013.01); *C12Q 1/6804* (2013.01); *G01N 2440/00* (2013.01)

(58) Field of Classification Search
None
See application file for complete search history.

(56) References Cited

U.S. PATENT DOCUMENTS

2013/0217027 A1 8/2013 Bernstein et al.

FOREIGN PATENT DOCUMENTS

| WO | WO 2012/047726 | 4/2012 |
| WO | WO 2013/184930 | 12/2013 |

OTHER PUBLICATIONS

Alewood, P., Alewood, D., Miranda, L., Love, S., Meutermans, W., and Wilson, D. (1997). Rapid in situ neutralization protocols for Boc and Fmoc solid-phase chemistries. Methods Enzymol. 289, pp. 14-29.
Benayoun, B.A., Pollina, E.A., Ucar, D., Mahmoudi, S., Karra, K., Wong, E.D., Devarajan, K., Daugherty, A.C., Kundaje, A.B., Mancini, E., et al. (2014). H3K4me3 Breadth Is Linked to Cell Identity and Transcriptional Consistency. Cell 158, pp. 673-688.
Bernstein, B.E., Meissner, A., and Lander, E.S. (2007). The mammalian epigenome. Cell 128, pp. 669-681.
Bernt K.M. et al. (2011). MLL-rearranged leukemia is dependent on aberrant H3k79 methylation by DOT1L. Cancer Cell 20, pp. 66-78.
Bin Liu, Yi, J., SV, A., Lan, X., Ma, Y., Huang, T.H., Leone, G., and Jin, V.X. (2013). QChIPat: a quantitative method to identify distinct binding patterns for two biological ChIP-seq samples in different experimental conditions. BMC Genomics 14, S3.
Blankenberg, D., Von Kuster, G., Coraor, N., Ananda, G., Lazarus, R., Mangan, M., Nekrutenko, A., and Taylor, J. (2010). Galaxy: a web-based genome analysis tool for experimentalists. Curr. Protoc. Mol. Biol. Ed. Frederick M Ausubel AI Chapter 19, Unit 19.10. pp. 1-21.
Bock, I., Dhayalan, A., Kudithipudi, S., Brandt, O., Rathert, P., and Jeltsch, A. (2011). Detailed specificity analysis of antibodies binding to modified histone tails with peptide arrays. Epigenetics off. J. DNA Methylation Soc. 6, pp. 256-263.
Brand, M., Rampalli, S., Chaturvedi, C.-P., and Dilworth, F.J. (2008). Analysis of epigenetic modifications of chromatin at specific gene loci by native chromatin immunoprecipitation of nucleosomes isolated using hydroxyapatite chromatography. Nat. Protoc. 3, pp. 398-409.
Chen, Z., Grzybowski, A.T., and Ruthenburg, A.J. (2014). Traceless semisynthesis of a set of histone 3 species bearing specific lysine methylation marks. Chembiochem 15, pp. 2071-2075.
Chi, P., Allis, C. D. & Wang, G.G. (2010). Covalent histone modifications—miswritten, misinterpreted and mis-erased in human cancers. Nat. Rev. Cancer 10, pp. 457-469.
Daigle, S.R. et al. (2011). Selective killing of mixed lineage leukemia cells by a potent small-molecule DOT1L inhibitor. Cancer Cell 20(1) pp. 53-65.
Dawson, M.A., and Kouzarides, T. (2012). Cancer epigenetics: from mechanism to therapy. Cell 150, pp. 12-27.
Dawson, P.E., Muir, T.W., Clark-Lewis, I., and Kent, S.B. (1994). Synthesis of proteins by native chemical ligation. Science 266, pp. 776-779.
Egelhofer, T. A. et al. (2011). An assessment of histone-modification antibody quality. Nat Struct Mol Biol 18, pp. 91-93.

(Continued)

Primary Examiner — Christopher M Gross
(74) Attorney, Agent, or Firm — Ryan L. Marshall; Barnes & Thornburg LLP

(57) ABSTRACT

One aspect of the present invention describes materials and methods of quantitatively measuring the density or percent occupancy of DNA binding proteins such as histones, histone variants, histone post translational modifications and transcription factors in chromatin at given DNA loci. One embodiment measures a factor's average quantity at specific gene loci, and controls for a number of pitfalls concerning antibody quality and handling issues. Other embodiments include calibrating and quantifying chromatin immunoprecipitation assays, assessing an affinity reagent specificity, as well as required reagents and their formulation in kits. Another embodiment allows for the diagnosis of a condition or disease by measuring the density of a histone modification at a genomic locus.

14 Claims, 9 Drawing Sheets

Specification includes a Sequence Listing.

(56) References Cited

OTHER PUBLICATIONS

Feinberg, A.P. (2007). Phenotypic plasticity and the epigenetics of human disease. Nature 447, pp. 433-440.
Fuchs, S. M., Krajewski, K., Baker, R. W., Miller, V. L. & Strahl, B. D. Influence of combinatorial histone modifications on antibody and effector protein recognition. Curr Biol 21, pp. 53-58 (2011).
Giardine, B., Riemer, C., Hardison, R.C., Burhans, R., Elnitski, L., Shah, P., Zhang, Y., Blankenberg, D., Albert, I., Taylor, J., et al. (2005). Galaxy: a platform for interactive large-scale genome analysis. Genome Res. 15, pp. 1451-1455.
Goecks, J., Nekrutenko, A., Taylor, J., and Galaxy Team (2010). Galaxy: a comprehensive approach for supporting accessible, reproducible, and transparent computational research in the life sciences. Genome Biol. 11, R86.
Gryzbowski et al., Molecular Cell 58: pp. 886-899, (2015).
Guenther, M.G., Levine, S.S., Boyer, L.A., Jaenisch, R., and Young, R.A. (2007). A chromatin landmark and transcription initiation at most promoters in human cells. Cell 130, pp. 77-88.
Hattori, T., Taft, J.M., Swist, K.M., Luo, H., Witt, H., Slattery, M., Koide, A., Ruthenburg, A.J., Krajewski, K., Strahl, B.D., et al. (2013). Recombinant antibodies to histone post-translational modifications. Nat Methods 10, pp. 992-995.
Henikoff, S. (2008). Nucleosome destabilization in the epigenetic regulation of gene expression. Nat. Rev. Genet. 9, pp. 15-26.
Herold, J., Kurtz, S., and Giegerich, R. (2008). Efficient computation of absent words in genomic sequences. BMC Bioinformatics 9, 167.
International Search Report for PCT/US2015/014296, dated Jul. 13, 2015, 6 pgs.
Jiang, C., and Pugh, B.F. (2009). Nucleosome positioning and gene regulation: advances through genomics. Nat. Rev. Genet. 10, pp. 161-172.
Johnson, E.C.B., and Kent, S.B.H. (2006). Insights into the mechanism and catalysis of the native chemical ligation reaction. J. Am. Chem. Soc. 128, pp. 6640-6646.
Kroon E and Krosl J. (1998). Hoxa9 transforms primary bone marrow cells through specific collaboration with Meis1a but not Pbx1b. EMBO 17(13) pp. 3714-3725.
Kuan et al., (2011). "A Statistical Framework for the Analysis of ChIP-Seq Data," Journal of American Statistical Association, vol. 106, Iss. 495, pp. 1-35.
Landt, S. G. et al. (2012). "ChIP-seq guidelines and practices of the ENCODE and modENCODE consortia."Genome Res 22, pp. 1813-1831.
Langmead, B., Trapnell, C., Pop, M., and Salzberg, S.L. (2009). Ultrafast and memory-efficient alignment of short DNA sequences to the human genome. Genome Biol. 10, R25.
Lauberth, S.M., Nakayama, T., Wu, X., Ferris, A.L., Tang, Z., Hughes, S.H., and Roeder, R.G. (2013). H3K4me3 Interactions with TAF3 Regulate Preinitiation Complex Assembly and Selective Gene Activation. Cell 152, pp. 1021-1036.
Leroy, G., Dimaggio, P.A., Chan, E.Y., Zee, B.M., Blanco, M.A., Bryant, B., Flaniken, I.Z., Liu, S., Kang, Y., Trojer, P., et al. (2013). A quantitative atlas of histone modification signatures from human cancer cells. Epigenetics Chromatin 6, 20.
Li, B., and Carey, M. (2007). The Role of Chromatin during Transcription. Cell 128, pp. 707-719.
Li, H., Handsaker, B., Wysoker, A., Fennell, T., Ruan, J., Homer, N., Marth, G., Abecasis, G., Durbin, R., and 1000 Genome Project Data Processing Subgroup (2009). The Sequence Alignment/Map format and SAMtools. Bioinforma. Oxf. Engl. 25, pp. 2078-2079.
Liang, K., and Keles, S. (2012). Normalization of ChIP-seq data with control. BMC Bioinformatics 13, 199.
Lowary, P.T., and Widom, J. (1998). New DNA sequence rules for high affinity binding to histone octamer and sequence-directed nucleosome positioning. J. Mol. Biol. 276, pp. 19-42.
Luger, K., Rechsteiner, T.J., and Richmond, T.J. (1999). Preparation of nucleosome core particle from recombinant histones. Methods Enzymol. 304, pp. 3-19.

Marinov, G.K., Kundaje, A., Park, P.J., and Wold, B.J. (2014). Large-scale quality analysis of published ChIP-seq data. G3 (Bethesda) 4, pp. 209-223.
Mikkelsen, T.S., Ku, M., Jaffe, D.B., Issac, B., Lieberman, E., Giannoukos, G., Alvarez, P., Brockman, W., Kim, T.-K., Koche, R.P., et al. (2007). Genome-wide maps of chromatin state in pluripotent and lineage-committed cells. Nature 448, pp. 553-560.
Muthurajan, U.M., Park, Y.-J., Edayathumangalam, R.S., Suto, R.K., Chakravarthy, S., Dyer, P.N., and Luger, K. (2003). Structure and dynamics of nucleosomal DNA. Biopolymers 68, pp. 547-556.
Nady, N., Min, J., Kareta, M.S., Chédin, F., and Arrowsmith, C.H. (2008). A SPOT on the chromatin landscape? Histone peptide arrays as a tool for epigenetic research. Trends Biochem. Sci. 33, pp. 305-313.
Nishikori, S., Hattori, T., Fuchs, S.M., Yasui, N., Wojcik, J., Koide, A., Strahl, B.D., and Koide, S. (2012). Broad ranges of affinity and specificity of anti-histone antibodies revealed by a quantitative peptide immunoprecipitation assay. J Mol Biol 424, pp. 391-399.
Park, P.J. (2009). ChIP-seq: advantages and challenges of a maturing technology. Nat. Rev. Genet. 10, pp. 669-680.
Quinlan, A.R., and Hall, I.M. (2010). BEDTools: a flexible suite of utilities for comparing genomic features. Bioinforma. Oxf. Engl. 26, pp. 841-842.
Ruthenburg et al., "Recognition of a mononucleosomal histone modification patter by BPTF via multivalent interactions," Cell (May 27, 2012), vol. 145, No.5, pp. 692-706.
Ruthenburg, A.J., Li, H., Milne, T.A., Dewell, S., McGinty, R.K., Yuen, M., Ueberheide, B., Dou, Y., Muir, T.W., Patel, D.J., et al. (2011). Recognition of a mononucleosomal histone modification pattern by BPTF via multivalent interactions. Cell 145, pp. 692-706.
Ryuichiro et al., "Recent advances in ChiP-seq analysis: from quality management to whole-genome annotation," Briefings in Bioinformatics, (2017), 18(2), pp. 279-290.
Santos-Rosa, H., Schneider, R., Bannister, A.J., Sherriff, J., Bernstein, B.E., Emre, N.C.T., Schreiber, S.L., Mellor, J., and Kouzarides, T. (2002). Active genes are tri-methylated at K4 of histone H3. Nature 419, pp. 407-411.
Schubeler, D. (2004). The histone modification pattern of active genes revealed through genome-wide chromatin analysis of a higher eukaryote. Genes & Development 18, pp. 1263-1271.
Shah et al., (Molecular Cell 72: pp. 162-177, (2018).
Shogren-Knaak, M.A., and Peterson, C.L. (2003). Creating Designer Histones by Native Chemical Ligation. In Methods in Enzymology, C. David Allis and Carl Wu, ed. (Academic Press), pp. 62-76.
Supplementary Search Report for Appl. No. EP 15744035.5, dated Jun. 27, 2017.
Teytelman et al., "Highly expressed loci are vulnerable to misleading ChIP localization of multiple unrelated proteins," Proc. Natl. Acad. Sci. USA, 110 (46), pp. 18602-18607, (Nov. 12, 2013).
Trygve Tollefsbol Epigenetics in Human Disease 2012 Academic Press.
Voigt, P., Leroy, G., Drury, W.J., III, Zee, B.M., Son, J., Beck, D.B., Young, N.L., Garcia, B.A., and Reinberg, D. (2012). Asymmetrically modified nucleosomes. Cell 151, pp. 181-193.
Wan, Q., and Danishefsky, S.J. (2007). Free-radical-based, specific desulfurization of cysteine: a powerful advance in the synthesis of polypeptides and glycopolypeptides. Angew. Chem. Int. Ed Engl. 46, pp. 9248-9252.
Written Opinion for PCT/US2015/014296, dated Jul. 13, 2015, 10 pgs.
Yigit et al., "High-resolution nucleosome mapping of targeted regions using BAC-based enrichment," Nucleic Acids Research, (Feb. 2013), pp. 1-11.
Young, N.L., Dimaggio, P.A., Plazas-Mayorca, M.D., Baliban, R.C., Floudas, C.A., and Garcia, B.A. (2009). High throughput characterization of combinatorial histone codes. Mol Cell Proteomics 8, pp. 2266-2284.
Zhang, Y., Liu, T., Meyer, C.A., Eeckhoute, J., Johnson, D.S., Bernstein, B.E., Nussbaum, C., Myers, R.M., Brown, M., Li, W., et al. (2008). Model-based analysis of ChIP-Seq (MACS). Genome Biol 9, R137.

(56) References Cited

OTHER PUBLICATIONS

Zhang, Z., and Pugh, B.F. (2011). High-resolution genome-wide mapping of the primary structure of chromatin. Cell 144, pp. 175-186.

COMPOSITIONS AND METHODS FOR QUANTITATIVE ASSESSMENT OF DNA-PROTEIN COMPLEX DENSITY

CROSS-REFERENCES TO RELATED APPLICATIONS

This application is a divisional of U.S. patent application Ser. No. 15/115,081, filed Jul. 28, 2016, which claims the benefit of International Application PCT/US2015/014296, filed Feb. 3, 2015, which claims the benefit of U.S. Provisional Patent Application No. 61/935,129, filed Feb. 3, 2014, the contents of which applications are hereby incorporated by reference.

The present patent application claims the benefit of the filing date of U.S. Provisional Patent Application No. 61/935,129, filed Feb. 3, 2014, the contents of which is hereby incorporated by reference.

FEDERALLY SPONSORED RESEARCH

This invention was made with U.S. government support under grant numbers NIH-1R21HG007426. The government has certain rights in the invention.

BACKGROUND

Chromatin, the assemblage of protein and DNA that is the physiologic form of the genome, is a crucial regulator of underlying DNA function, playing key roles in all aspects of DNA metabolism, cell and whole organism function. The fundamental repeating unit of chromatin structure is the nucleosome: a DNA-binding spool of eight core histone proteins (two copies of H2A, H2B, H3, and H4), around which nearly two full turns of genomic DNA are wrapped. Individual nucleosomes may be generated, for example, by micrococcal nuclease digestion. The histones include the H1, H2A, H2B, H3, and H4 histones and may be modified to include a plurality of epitopes and post-translational modifications.

In the cell, post-translational modifications (or variation of the amino acid sequence) of the histone are able to regulate changes in local chromatin states that govern the accessibility of underlying DNA, regulating processes that range from transcriptional activation to gene silencing. These chemical modifications are referred to as "epigenetic marks" and add another layer of information without altering the standard base-pairing capacity of DNA and seem to act in concert with one another and other distinguishing chromatin features to control the genome. Cellular processes as varied as transcription, replication, stem cell pluripotency, gene silencing, X-chromosome inactivation, DNA repair, apoptosis, epigenetic inheritance, cellular identity retention, hematopoiesis, cancers, numerous disorders of the central nervous system, cardiovascular disease, diabetes, obesity, bacterial infections, and gene expression programs during development all appear to involve epigenetic modifications in their course or causation.

Chromatin immunoprecipitation (ChIP) is the central methodology for querying where these epigenetic modifications exist in the genome as well as tracking their changes as a function of cellular identity in development and pathological transitions (e.g., hematopoetic stem cell to leukemia). ChIP is well known in the art. In brief, ChIP is a pull-down assay that relies on fragmenting genomic material of living organisms by mechanical, physical, chemical or enzymatic shearing to generate a pool of protein-DNA fragments (largely nucleosomes) that can then be probed with an affinity reagent such as an antibody that binds a particular protein or posttranslational modification thereof to pull-down specific fragments of chromatin. ChIP uses affinity capture from a pool of fragmented chromatin "input" to enrich fragments that bear the epitope of interest. The identity, relative abundance and position in the genome of the indirectly captured DNA fragments can be identified by numerous techniques including RT-PCR, Next Generation Sequencing, ddPCR, qPCR, microarray probe hybridization and other methods with capability to read out and quantify DNA sequence, all of which are known in the art.

This information about the position of DNA associated with protein in situ can be then used to infer the position of the bound protein to the DNA in the intact genome, and provide an assessment of how much bound material was present at that DNA loci as compared to the frequency of that sequence in the initial pool of fragments subjected to affinity capture, i.e., "the input", or relative to some other genomic locus. In other words, the captured material is analyzed by qPCR, next generation sequencing, or the like and compared to negative controls to assess the relative enrichment afforded by the immunoprecipitation, also known as pull-down. Notably, present technology answers the "where in the genome" question in a relative sense, without providing meaningful information about the actual abundance of the targeted epitope at that site. Nevertheless, ChIP has provided insight into how a combination of positioning, histone marks and histone variants can regulate gene expression (Henikoff, 2008; Jiang and Pugh, 2009; Li and Carey, 2007) and how these changes can regulate cell differentiation (Bernstein et al., 2007). Moreover, it is a crucial tool in understanding the role of epigenetics in cancer and other diseases, including discovery of disease markers (Dawson and Kouzarides, 2012; Feinberg, 2007).

Despite serving as the central experimental technique in epigenetics research, chromatin immunoprecipitation coupled to deep sequencing (ChIP-seq) or other analysis suffers from several serious drawbacks. First, each ChIP measurement is relative, it is not standardized to any reference, which hinders direct comparison of data coming from different repetitions of the same sample, different cells, and different patients. Second, ChIP is heavily dependent on the quality of antibody reagents which vary in specificity and affinity even within different batches of the same antibody, which can have significant affinity for off-target epitopes often leading to false-positive detection and misinterpretation of the data (Bock et al., 2011; Nady et al., 2008; Park, 2009; Fuchs et al., 2011; Landt et al., 2012; Egelhofer et al., 2011). The greatest source of experimental error in ChIP is the quality of the antibody affinity reagents employed to capture desired epitopes (either histone modifications, variants or transcription factors). The troubling promiscuity of "ChIP grade" antibody binding revealed using immobilized arrays of related peptide epitopes (Bock et al., 2011; Egelhofer et al., 2011; Fuchs et al., 2011), is compounded by increasingly sophisticated measures of affinity, specificity and reproducibility; up to 80% of several hundred commercial antibodies failed stringent quality controls (Egelhofer et al., 2011; Landt et al., 2012). Even different lots of the same commercial antibody can vary in apparent affinity for target by up to 20-fold (Hattori et al., 2013) and display marked specificity differences (Nishikori et al., 2012). Yet at present, there are no available measures of antibody specificity within ChIP experiments available, leading to substantial uncertainty in evaluating the data. Third, even with equivalent antibody affinity and specificity for two different epitopes, the wide variability of epitope abundance would preclude meaningful comparison of ChIP results (Leroy et al., 2013; Young et al., 2009). Finally, very small differences in ChIP preparation can yield significant differences in the output data, leading to inconsistency from experiment to experiment. Differences in experimenter handling (Marinov et al., 2014), as well as loading equivalent quantities of sample in each sequencer lane despite differential amplification (Zhang and Pugh, 2011) render unbiased ChIP-based comparisons problematic.

Because ChIP data are expressed on a relative scale that is severely dependent on the precise experimental conditions, normalization ultimately requires assumptions that may not be warranted (Bin Liu et al., 2013; Liang and Keles, 2012), or the bulk of experimental data must be sacrificed in peak calling to permit comparisons (Zhang et al., 2008). Beyond peak calling, there are few widely applied ChIP-seq quality controls, yet in the worst cases, ChIP is not reproducible (Egelhofer et al., 2011; Landt et al., 2012; Marinov et al., 2014). Yet none of these factors are taken into account in current methodologies or technologies. With present ChIP technology, it is impossible to measure the absolute densities of histone modifications in a locus-specific manner. Consequently, the peaks of different histone modifications that seem to overlap on certain genomic loci cannot be meaningfully compared. Moreover, experimental variation and pitfalls that are opaque to the experimenter preclude ChIP assays from serving as reliable patient diagnostics (despite clear connections between the epigenetic marks it measures and numerous disease states), as well as hinder the utility of ChIP in basic science research.

SUMMARY OF PRESENTLY PREFERRED EMBODIMENTS OF THE INVENTION

One aspect of the he present invention provides materials and methods to make pull-down assays, such as ChIP, applicable to medical diagnostics and research. The present invention enables quantification of results from pull-down assays with absolute values. Materials and Methods are provided that are related to evaluating samples containing nucleosomes to determine the density of specific epitopes at genomic loci across multiple samples.

In one aspect of the invention, there are methods to transform the results of a pull-down assay from an arbitrary scale with arbitrary units into a standardized scale with absolute units, which improve accuracy of data interpretation. In one embodiment of the invention a standard comprises at least one reconstituted, recombinant, semi-synthetic and/or variant-containing DNA-binding protein, such as a histone comprising a post-translational modification of interest, with native-like affinity, specificity and avidity of a true positive epitope. In a preferred embodiment a standard also contains a barcode molecule that is linked to the reconstituted, recombinant, semi-synthetic and/or variant-containing DNA-binding protein. Numerous standards of the same type may constitute a standard. Numerous standards of different types may also constitute a standard. A "standard" can be, for example, a plurality of histone-barcode molecules of the same type or, in other embodiments, can include histone-barcode molecules including a number of different barcode molecules, each indicating, for example different concentrations at which the standard in doped into the library.

In another aspect of the invention, pull-down efficiency of false positive and true positive epitopes in situ is quantified, which improves precision of data interpretation, by employing a set of standards. In one embodiment, a set of standards includes at least one reconstituted, semi-synthetic or variant-containing DNA-binding protein with native-like affinity, specificity and avidity of a true positive epitope and at least one semi-synthetic or variant-containing DNA-binding protein with native-like affinity, specificity and avidity of a false positive epitope. The use of said set of standards improves absolute quantification of pull-down assay as it enables one to quantitate abundance of false positive and true positive epitopes in situ. The knowledge of abundance of false positive and true positive epitopes in situ improves data analysis as a Positive Predictive Value can be readily calculated. Knowledge of a Positive Predictive Value improves data analysis, as it allows an estimation of minimal abundance of epitope at a certain confidence level to be considered true positive, which is critical for such uses as medical diagnostics and research.

In another aspect of the invention, the invention provides a kit comprising a standard or a set of standards and one or more affinity reagents for absolute quantification of true positive and—in the case of a set of standards—false positive epitopes in chromatin immunoprecipitation assay. In yet another aspect of the invention, the invention provides a method of comparing pull-down assay results across multiple samples.

In another aspect, the invention provides a method of determining a density of a first epitope of a core histone at a genomic locus in chromatin of a cell. The method includes preparing a library of native nucleosomes from the chromatin, wherein the library comprises a nucleosome comprising the core histone having the first epitope and a nucleosome nucleotide sequence indicative of the genomic locus. A standard is added to the library to create a doped library; wherein the standard comprises a reconstituted nucleosome comprising (i) a standard histone or standard histone fragment having the first epitope and (ii) a standard molecule comprising a standard nucleotide sequence linking to a barcode molecule, wherein the standard histone or standard histone fragment and the standard nucleotide sequence form a stable protein-DNA association.

A first affinity reagent is added to the doped library to capture an amount of native nucleosomes and standard comprising the first epitope and a relative genomic abundance determined for the first epitope by comparing the amount of a given nucleotide sequence associated with the captured native nucleosomes comprising the first epitope and the amount of a given nucleotide sequence associated with the native nucleosome in an input amount from the doped library. A standard capture efficiency is determined for the first epitope by comparing the amount of a barcode sequence associated with the captured standard and the amount of a given nucleotide sequence associated with the standard in an input amount from the doped library. The density of the first epitope of the core histone at the genomic locus id determined by comparing the relative genomic abundance to the standard capture efficiency.

In one embodiment, determining the standard capture efficiency comprises comparing the ratio of a captured amount of the barcode molecule to an input amount of the reconstituted nucleosomes. In another embodiment, determining the relative genomic abundance comprises comparing the ratio of a captured amount of the native nucleosome nucleotide sequence to an input amount of native nucleosome nucleotide sequence. In yet another embodiment, the first affinity agent is an antibody directed towards the first epitope.

In certain embodiments a plurality of standards is added to the library, each standard comprising a reconstituted nucleosome comprising (i) the standard histone having the first epitope and (ii) the standard molecule comprising the standard nucleotide sequence linking to the barcode molecule, wherein the barcode molecule encodes a concentration parameter indicative of the concentration of the standard added to the library and wherein standards having at least two differing concentrations are added to the library. The plurality of standards may further include standards comprising reconstituted nucleosomes comprising (i) one or more off-target epitopes and (ii) a standard molecule barcode encoding an off-target epitope identity and concentration parameters indicative to the off-target epitope.

Determining a specificity of off-target capture for the first affinity reagent may be based on one or more capture efficiencies for the off-target epitopes and correcting the density of the first epitope of the core histone at the genomic locus based on the specificity of off-target capture. The first epitope is a post-translational modification or a protein isoform. The barcode sequence may be a sequence absent in the genome of the cell.

The abundance of at least one of the nucleosome nucleotide sequence and the standard nucleotide sequence may be determined by a method selected from the group consisting of PCR, qPCR, ddPCR, Next Generation Sequencing, hybridization, autoradiography, fluorescent labeling, optical density and the use of intercalating fluorescent probes. The first epitope of the core histone may comprise at least one post-translational amino acid modification selected from the group consisting of N-acetylation of serine and alanine; phosphorylation of serine, threonine and tyrosine; N-crotonylation, N-acetylation of lysine; N6-methylation, N6,N6-dimethylation, N6,N6,N6-trimethylation of lysine; omega-N-methylation, symmetrical-dimethylation, asymmetrical-dimethylation of arginine; citrullination of arginine; ubiquitinylation of lysine; sumoylation of lysine; O-methylation of serine and threonine, and ADP-ribosylation of arginine, aspartic acid and glutamic acid.

The standard molecule may be a double stranded polynucleotide. The double-stranded polynucleotide may include a nucleotide sequence selected from the group consisting of a SEQ ID. NOs 1-115. The barcode molecule may include a molecule selected from the group consisting of a nucleotide barcode sequence molecule, a locked nucleic acid sequence and a DNA sequence.

The cell may be a cell from a patient and wherein the amount of the first epitope at a given locus is indicative of a disease or condition selected from the group consisting of renal cell carcinoma, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesothelioma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, glioma, liposarcoma, infections caused by *Heliocobacter pylori, Listeria monocytogenes, Shigella flexneri, Anaplasma phagocytophilum*, Chlamdophila, Epstein-Barr Virus, herpes, HIV, *Schistosoma haematobium*; Obesity, diabetes, heart disease; autism, fragile X syndrome, ATR-X syndrome, Angelman syndrome, Prader-Willi syndrome, Beckwith Wiedemann syndrome, Rett syndrome, Rubinstein-Taybi syndrome, Coffin-Lowry syndrome Immunodeficiency-centrometric instability-facial anomalies syndrome, α-thalassaemia, leukemia, Huntington's disease, schizophrenia, bipolar disease, aging, dementia, Alzheimer's disease, Parkinson's disease, Cornelia de Langue syndrome, Kabuki syndrome, Sjogren's syndrome, Vitiligo, progressive systemic sclerosis, psoriasis, primary biliary cirrhosis, Crohn's disease and ulcerative colitis, Hashimoto's thyroiditis, Grave's disease, inflammatory bowel disease, atherosclerosis, and cardiac hypertrophy.

Another embodiment provides a method of determining a density of a first epitope of a core histone at a genomic locus in chromatin of a cell. The method includes preparing a library of native nucleosomes from the chromatin, wherein the library comprises nucleosomes, each comprising the core histone and a nucleosome nucleotide sequence indicative of its genomic locus of origin. A standard is added to the library to create a doped library; wherein the standard comprises a reconstituted nucleosome comprising (i) a standard histone or standard histone fragment having the first epitope and (ii) a standard molecule comprising a barcode molecule, wherein the standard histone or standard histone fragment and the standard molecule form a stable protein-DNA association.

The amount of the core histone is determined at the genomic locus in the doped library and the amount of standard in the doped library is determined. An affinity reagent is added to the doped library to capture an amount of native nucleosomes and reconstituted nucleosomes comprising the epitope and a relative genomic abundance determined for the first epitope at a genomic locus based on the amount of the captured standard comprising the epitope and the amount of the core histone at the genomic locus in the doped library. A standard capture efficiency is determined for the epitope based on the amount of captured reconstituted nucleosomes and the amount of standard in the doped library and the relative genomic abundance determined of the first epitope of the core histone at the genomic locus based on the first epitope abundance for the core histone and the standard capture efficiency.

In one embodiment determining the amount of the core histone at the genomic locus in the doped library includes adding a second affinity reagent to the doped library to recover an amount of nucleosomes comprising a second epitope, wherein the second epitope is an invariant epitope present on the core histone, and determining an amount of nucleosome nucleotide sequence in the amount of recovered nucleosomes comprising the second epitope. In another embodiment determining the amount of standard in the doped library includes recovering an amount of reconstituted nucleosome; wherein the reconstituted nucleosome comprises the second epitope, and determining an amount of the standard molecule in the amount of recovered reconstituted nucleosomes comprising the second epitope. In yet another embodiment, the first affinity reagent is an antibody directed to the first epitope and wherein the second affinity reagent is an antibody directed to the second epitope.

Another aspect provides a composition comprising a nucleosome comprising a nucleotide sequence selected from the group consisting of sequences comprising SEQ ID. NOs 1-115. Yet another aspect provides a kit for performing the method as described herein. In one embodiment, the kit includes one or more standards comprising a plurality of epitopes and standard molecules comprising a barcode. In another embodiment, the kit comprises at least one affinity reagent that recognizes at least one of the plurality epitope.

DETAILED DESCRIPTION

Figure 1:
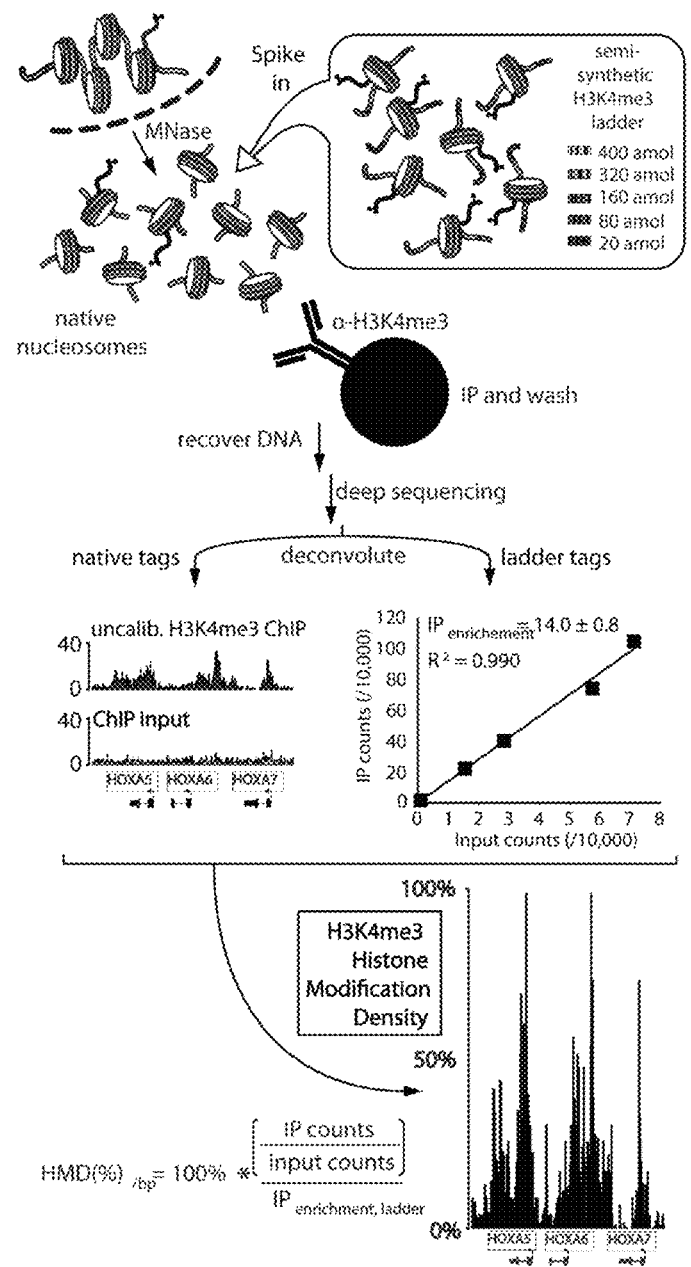
FIG. 1 is a schematic diagram of H3K4me3 ICe-ChIP-seq—one of the embodiments of calibrated chromatin immunoprecipitation experiments.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

I) Definitions

The term "Epitope" refers to any site on biomolecule that can evoke binding of affinity reagent. Affinity reagent might recognize linear sequence of biomolecule or biomolecule fragment, shape of biomolecule or biomolecule fragment, chemo-physical property of biomolecule or it fragment or combination of these.

"Amino acids" may be referred to herein by either their commonly known three letter symbols or by the one-letter symbols recommended by the IUPAC-IUB Biochemical Nomenclature Commission. Amino acid residues in proteins or peptides are abbreviated as follows: phenylalanine is Phe or F; leucine is Leu or L; isoleucine is Ile or I; methionine is Met or M; valine is Val or V; serine is Ser or S; proline is Pro or P; threonine is Thr or T; alanine is Ala or A; tyrosine is Tyr or Y; histidine is His or H; glutamine is Gln or Q; asparagine is Asn or N; lysine is Lys or K; aspartic acid is Asp or D; glutamic Acid is Glu or E; cysteine is Cys or C; tryptophan is Trp or W; arginine is Arg or R; and glycine is Gly or G.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs/orthologs, and alleles of the agents described herein.

An "antigen" as used herein may be any amino acid fragment (modified or unmodified) of 5 amino acids or more which are recognized by an antibody or for which recognizing antibodies can be raised. In certain embodiments, antigens may comprise modifications of an amino acid, such as acetylation, methylation (e.g. mono-, di-, tri-), phosphorylation, ubiquitination e.g. mono-, di-, tri-, poly-), sumoylation, ADP-ribosylation, citullination, biotinylation, and cis-trans isomerization. In other embodiments, antigens may comprise specific mutations, such as point mutations. In other yet embodiments, antigens may comprise wild-type amino acid sequence.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins, wherein the amino acid residues are linked by covalent peptide and/or pseudopeptide bonds.

The term "post-translational modification" refers to any modification of a natural or non-natural amino acid that occurs or would occur to such an amino acid after it has been incorporated into a polypeptide chain in vivo or in vitro. Such modifications include, but are not limited to, acetylation, methylation (e.g. mono-, di-, tri-), phosphorylation, ubiquitination (e.g. mono-, di-, tri-, poly-), sumoylation, ADP-ribosylation, citullination, biotinylation, and cis-trans isomerization. Such modifications may be introduced synthetically, e.g. chemically, during polypeptide synthesis or enzymatically after polypeptide synthesis or polypeptide purification.

The term "immunoprecipitation (IP) enrichment" refers to the internal standard reads from the immunoprecipitated sample divided by the internal standard reads from the input sample.

The term "asymmetric" refers to a nucleosome wherein one histone within a dimer of histones contains a post-translational modification. For example, the trimethyl modification is found on lysine 9 of one histone H3 but absent on the second H3 within a dimer.

The term "symmetric" refers to a nucleosome wherein both histones within a dimer of histones contain a post-translational modification. For example, the trimethyl modification is found on lysine 9 of both histone H3.

II) Internal Standard Calibrated ChIP (ICeChIP)

Currently performed pull-down assays suffer from arbitrary of the units of measurement, which makes any kind of comparison between any kind of pull-down experiment highly inaccurate and hinders use of pull-down assays in medical diagnostics and research. Accuracy of data interpretation is improved by a standardized scale with absolute units by uncoupling test outcome values from the assay and coupling them to actual biological phenomenon. One aspect of the present invention provides materials and methods enabling the use of pull-down assays in medical diagnostics such as in assays identifying disease markers. In these methods, the data resulting from the pull-down assay, such as ChIP, are characterized not by arbitrary values specific for an assay but by absolute values specific for the disease marker itself. This means that results from pull-downs of different samples, different pull-downs of the same sample, pull-downs of different epitopes, pull-downs performed in different laboratories may be readily and directly compared to each other which is often impossible with currently available methods and technologies.

One aspect of the invention includes a method of absolute assessment of DNA bound proteins, protein isoforms, and protein post-translational modification densities that we call Internal Standard Calibrated ChIP (ICeChIP). This method provides the first local measurement of histone modifications on a biologically meaningful scale. This improvement of ChIP utilizes a non-naturally occurring internal standard to which ChIP readout may be compared. As an internal standard, we have developed recombinant and semi-synthetic protein-DNA complexes engineered to contain epitopes with native-like affinity, specificity and avidity characteristics.

These protein-DNA complexes include nucleosomes bearing protein epitopes with native-like affinity, specificity and avidity for an affinity reagent, and a DNA sequence including a standard recognition molecule comprising a positioning sequence and a unique sequence or barcode. The "barcode", which provides a unique means of specific recognition of the DNA-protein complex, may be for example a nucleotide sequence such as DNA, a polypeptide, fluorophore, chromophore, RNA sequence, locked nucleic acid sequence, affinity tag etc., that identifies the identity and/or concentration of a specific standard semi-synthetic nucleosome. Here, the term "native-like" refers to any protein epitope having affinity, specificity and avidity properties similar to naturally occurring epitopes.

FIG. 1 shows one embodiment of an ICeChIP assay. In this schematic, a semi-synthetic nucleosome ladder of standards with modified histone H3 carrying N6,N6,N6-trimethylation of lysine 4 in defined concentrations (encoded by each unique DNA barcodes) is doped into a library of native nucleosomes isolated from human nuclei and released by in nucleo digestion with micrococcal nuclease. A sample of the ladder-doped library is then subjected to immunoprecipitation (IP), DNA purification and Next-Generation-Sequencing. Another sample of the ladder-doped library is retained as an input sample and is not subject to immunoprecipitation. Here, Immunoprecipitation (IP) or "pull-down" refers to a method or technique for purifying chromatin, nucleosomes, DNA-proteins complexes, or proteins including one or more epitopes of interest where the epitope is contacted with an affinity reagent specific to an epitope and separated from other components of the library.

The immunoprecipitated sample and the input sample are subject to a method with capability to read out and quantify DNA sequences. Recovered DNA fragments are mapped to the relative genomic position based on reference genome and abundance of these fragments is measured for every base pair of the genome for DNA recovered from IP (the sample produced through immunoprecipitation using an affinity reagent) and input (the sample not subject to immunoprecipitation). The same read counting from the sequencing data is performed for the unique nucleotide sequences used to make semi-synthetic nucleosomes. The ratio of abundance of semi-synthetic nucleosomes in IP and input is used to measure IP efficiency and the ratio of abundance of DNA fragments for any genomic loci in IP and input is used to measure relative enrichment. The resulting tag counts for the added semisynthetic nucleosomes constitute a calibration curve to derive histone modification density for native nucleosomes genome-wide. The average IP-enrichment ratio for the semi-synthetic nucleosome ladder bearing 100% of the modification is used as a scalar correction for native chromatin bearing the same epitope to compute the amount of modification over a desired genomic interval as a ratio of ratios. Subsequently IP efficiency is applied to relative enrichment to measure histone modification density of H3K4me3 histone post-translational modification with base pair resolution for the span of the whole genome. In some embodiments, protein epitopes having native-like affinity, specificity and avidity include a protein isoform and/or protein having a post-translational modification. For example, the epitope may be the histone modification to whose density is measured in the assay or an epitope having similar binding characteristics. In a preferred embodiment, the protein part of a DNA-protein complex is a core histone octamer complex containing core histones H2A, H2B, H3, H4. These sequences are described in Patent Application No: US2013/044537, the contents of which are incorporated by reference. In order to reproduce native-like affinity, specificity and avidity of the protein epitope for any of the aforementioned core histones can be represented by any histone variant including those in listed in Table 1a-f. In one embodiment of the invention, the protein epitope may be a fragment of a histone.

In another aspect of the invention, the protein-DNA complexes comprise a standard recognition molecule comprising but not limited to a positioning sequence and a unique sequence or barcode. Inclusion of a protein positioning sequence allows for the creation of a DNA-protein complex through specific native-like interaction with protein. In a preferred embodiment, the protein positioning sequence is a nucleosome positioning sequence. In one embodiment, the positioning sequence comprises a natural or synthetic double-stranded DNA sequence of at least 146 base pairs. In a more preferred embodiment, the protein positioning sequence is a "601-Widom" sequence—a synthetic nucleosome binding sequence made through a selection of sequences which exhibited affinity toward a nucleosome. While we have mentioned here a "601-Widom" sequence as a nucleosome positioning sequence the present embodiments encompass the use of other such synthetic and native sequences which exhibit affinity toward nucleosomes.

A unique sequence allows for specific identification of a DNA-protein complex in a library or pool of native DNA-protein complexes i.e. a barcode. In some embodiments the unique sequence can be substituted with another means of specific recognition e.g. a polypeptide, fluorophore, chromophore, RNA sequence, locked nucleic acid sequence, affinity tag etc. In one aspect, the unique sequence can be analyzed by known nucleotide analysis for example Next-Generation sequencing, qPCR. RT-PCR, or ddPCR. A unique sequence and a positioning sequence might be the same sequence and serve a dual function as the recognition molecule. The unique sequence may reside at the 5'-end of the positioning sequence, the 3'end of the positioning sequence, or at both ends of the positioning sequence.

In a preferred embodiment, a unique sequence is a duplex DNA sequence with minimal length to maintain a Hamming distance of at least 1 from the genomic sequence of the organism that is being investigated and all other sequences that might be found in the sample. In a more preferred embodiment, to guarantee robust discrimination of barcodes in the milieu of native genomic sequences, each barcode is made out of two 11 base pair (bp) sequences absent in human and mice genome (Herold et al., 2008), where 11 bp sequences is the shortest sequence guaranteeing Hamming distance of at least 1 for human and mice genome. In another embodiment, the barcode sequence is a sequence not present in the genome of the cell. In another embodiment, the barcode sequence is a sequence not present in nature. While 11 bp are mentioned here as the shortest possible sequence with Hamming distance of at least 1 for human and mouse there is unlimited number of longer sequences with Hamming distance of at least 1 which can be successfully used to serve as aforementioned unique sequences. Moreover the shortest sequence of unique sequence with Hamming distance of at least 1 for genomes of other organisms might be shorter than 11 bp and as such, shorter sequences than 11 bp might be successfully used for these organisms. The barcode is a molecule, in a preferred embodiment it is DNA, that can be analyzed by known DNA analysis comprising but not limited to Next-Generation sequencing and PCR. The barcode sequence encodes a concentration and/or identity of a given internal standard nucleosome.

In a preferred embodiment, a unique nucleotide sequence indicates the concentration and identity of a given internal standard. In one aspect of the invention, a unique sequence comprises a length of at least or at most 10, 11, 12, 13, 14, 15, 16, 17, 18, 19, 20, 25, 30, 35, 40, 45, 50, 60, 70, 80, 90 or 100 base pairs in length. In yet another embodiment, the total length of the positioning sequence and unique sequence has a length of at least 100 base pairs. In a preferred embodiment, a positioning sequence and a unique sequence are selected from Table 7. In one aspect, the unique sequence is micrococcal nuclease resistant. In one embodiment of the invention the standard molecule comprising but not limited to a positioning sequence and a unique sequence or barcode includes SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO: 11; SEQ ID NO:12; SEQ ID NO:13; SEQ ID NO:14; or SEQ ID NO:15. In a preferred embodiment, the standard molecule comprising but not limited to a positioning sequence and a unique sequence or barcode includes SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO: SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:87; SEQ ID NO:88; SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:100; SEQ ID NO:101; SEQ ID NO:102; SEQ ID NO:103; SEQ ID NO:104; SEQ ID NO: 105; SEQ ID NO:106 SEQ ID NO:107; SEQ ID NO:108; SEQ ID NO:109; SEQ ID NO:110; SEQ ID NO:111; SEQ ID NO:112; SEQ ID NO:113; SEQ ID NO:114; or SEQ ID NO:115.

In one embodiment of the method of determining epitope density as described wherein, a set of the aforementioned semi-synthetic nucleosomes with the standard recognition molecule is doped into a collection of native nucleosomes. The set may comprise of semi-synthetic nucleosomes with the standard recognition molecule harboring more than one epitope but comprising at least one epitope of interest. For example, a set of semi-synthetic nucleosomes may harbor the post-translational modification i.e. H3K9me3 and a conserved or invariant epitope such as the polypeptide sequence of the histone. Alternatively, a set of semi-synthetic nucleosomes may harbor more than one post-translational modification such as H3K9me3 or insert second epitope. In another aspect, the set of standards comprises at least one semi-synthetic, reconstituted, or variant-containing DNA-binding protein with native-like affinity, specificity and avidity of a false positive epitope that is different than the epitope of interest. In a preferred embodiment a set of semi-synthetic or variant containing nucleosomes including at least one nucleosome with native-like affinity, specificity and avidity of a true positive epitope and at least one nucleosome with native-like affinity, specificity and avidity of a false positive epitope.

To purify a population of native or semi-synthetic nucleosomes from a pool of protein-DNA complexes one may use an affinity capture step where an affinity reagent recognizes an invariant fragment of the nucleosome for example the histone. In one aspect the affinity reagent contacting the epitope of interest comprises an antibody, a monobody, an aptamer, a Fab, or a binding peptide. The method of purifying a population of nucleosomes may apply to semi-synthetic nucleosomes alone, native nucleosomes alone, or a native nucleosomes doped with semi-synthetic nucleosomes.

ICe-ChIP DATA ANALYSIS

In one embodiment, to perform ICe-ChIP a set of the aforementioned internal standards to which a ChIP read-out can be compared, is doped into a collection of native DNA-protein complexes. Below we describe how these standards are used to calculate Standard IP efficiency, which in turn can be used to calculate what we have called Protein or Epitope Density (PD), Protein Variant Density (PVD), or Protein Modification Density (PMD), depending whether the investigated epitope is an invariant protein fragment, protein isoform, or protein post-translational modification. Standards based on semi-synthetic or variant containing nucleosomes with native-like affinity, specificity and avidity improve a chromatin immunoprecipitation by allowing one to perform absolute quantification of Histone Modification Density (HMD) or Histone Variant Density (HVD).

Histone Modification Density is a standardized scale and is defined as the apparent percentage of nucleosomes bearing a specific epitope out of all nucleosomes in a given genomic position. Histone Modification Density is expressed on an analog scale ranging between 0%, meaning absence, and 100% meaning saturating presence of the epitope. For example 90% H3K4me3 Histone Modification Density for nucleosome +1 (the first nucleosome downstream of transcription start site) of GAPDH gene should be interpreted that in the population of all histone H3 molecules composing nucleosome +1 at the GAPDH gene promoter, 90% of them bear post translational modification N6,N6,N6-trimethylation of lysine 4 of histone H3 (H3K4me3) and 10% should be free of H3K4me3. While this example was given for region of genome spanning a single nucleosome, which is roughly 147 bp, the same can be applied to any span of the genome ranging from single base pair to the whole genome.

In order to calculate Protein or Epitope density one needs to know four things: genomic locus size, epitope abundance, general protein abundance, and ImmunoPrecipitation efficiency ("IP efficiency".) Genomic locus size is defined by the user and can range from a single base pair to the whole genome. Epitope abundance is defined as the abundance of the epitope over the span of the genomic locus. Abundance is usually inferred by quantifying the amount of DNA bound to DNA-protein complex as it is stoichiometric to protein and DNA is easy to quantify with numerous methods e.g. PCR, RT-PCR, ddPCR, Next-Generation-Sequencing, hybridization, autoradiography, fluorescent labeling, optical density, intercalating fluorescent probes etc. However, abundance may also be measured directly by measuring protein concentration through optical density, fluorescence, autoradiography, mass spectrometry, colorimetric assay, polypeptide total decomposition etc.

Epitope abundance is measured after an affinity capture step in which a specific affinity reagent recognizes the epitope, after which step epitope-affinity reagent complex is separated from unbound population of DNA-protein complexes. Most often epitope-affinity reagent complex is separated from unbound nucleosomes by immobilizing epitope-affinity reagent complex on the surface and washing away the unbound population of DNA-protein complexes. General protein abundance is defined as the abundance of all proteins of a given kind making DNA-complexes within the span of the given genomic locus. General protein abundance is measured with the same methods as epitope abundance.

To purify a population of nucleosomes from other protein-DNA complexes one can use an affinity capture step where an affinity reagent recognizes an invariant fragment of the nucleosome, for example the histone. However, if a given invariant fragment involved in making the protein-DNA complex is dominant over a considered genomic locus size then the affinity capture step for general protein population can be skipped under assumption that the population of other protein-DNA complexes is insignificant. The ratio of epitope abundance and general protein abundance should yield epitope density per protein. However it is rarely the case as the affinity capture step is 100% efficient and if two or more affinity capture steps are utilized their capture efficiencies will rarely be equal to each other. To solve this problem one needs to know relative IP efficiency between epitope abundance and general protein abundance measurement.

The "IP efficiency" refers to the relative recovery of the epitope between one or more pull-down. Knowledge of IP efficiency for the standard allows performing absolute quantification by correcting for differences in recovery between one or more pull-downs. In one embodiment, the aforementioned IP efficiency is measured by using a set of the aforementioned standards that has the same affinity, specificity and avidity as the native epitope and which abundance is easy to measure in a complex mixture. These semi-synthetic standards are doped into a pool of native DNA-Protein complexes, a sample of which will be subject to affinity capture. Following this step, the aforementioned measurements of epitope abundance and general protein density is performed for the semi-synthetic standards and the pool of native DNA-protein complexes population with one of the mentioned abundance measurement methods. In one embodiment, the set of standards includes standards that are added at differing concentrations. Here the concentration added is uniquely identified by the barcode.

In one embodiment, epitope abundance can be measured through quantification of DNA bound to DNA-protein complexes for standard DNA-protein complexes and native DNA-protein complexes. In a preferred embodiment, the ratio of epitope of a given standard barcode in the IP versus input material for semi-synthetic nucleosomes is equal to Standard IP Efficiency. Alternatively this Standard IP efficiency may be computed as a ratio of barcode abundance in the epitope-specific IP versus general protein abundance (for histone H3, for example the barcode counts in the anti-H3 general IP). Once IP efficiency is calculated, one may apply this Standard IP efficiency to IP/input DNA or IP-epitope/IP-general protein ratios any genomic locus. This is calculated by dividing the genomic IP efficiency—ratio of the epitope abundance in the IP (amount of DNA for a given genomic interval captured in the affinity step) to the amount of DNA covering the same interval present in the input—by the Standard IP efficiency. Alternatively this may be computed as the ratio of a given genomic DNA fragment in the IP divided amount of the same species in the general epitope abundance IP for any genomic locus as described above and then dividing by Standard IP efficiency. The resultant value is a Protein or Epitope Density (PD), also known as a Protein Variant Density (PVD), or Protein Modification Density (PMD).

$$PD(\text{per/bp}) = \frac{\left(\frac{IP}{\text{input}}\right) \cdot 100\%}{\text{Standard } IP \text{ efficiency}}$$

Correction of Off-Target Specificity

Another problem challenging analysis of pull-down experiments is the low precision of prediction stemming from off-target specificity of an affinity reagent used in a pull-down assay. The terms "false positive" and "off-target" are synonymous and refer to an epitope that contacts an affinity reagent promiscuously or non-specifically or an incorrect result. The term "true positive" and "on-target" are synonymous and refers to an epitope of interest or correct result.

Prevalence of false positive epitope signal varies between pull-down to pull-down and depends on the quality of affinity reagent (its intrinsic binding affinity for the desired epitope versus its affinity for other related epitopes), the abundance of on-versus off-target epitope in the native chromatin, the ratio of capacity of affinity reagent and loading levels of DNA-protein complexes in a pull-down, as well as other conditions under which the pull-down is performed. For different affinity reagents, on- and off-target binding both contribute to the apparent ChIP signal to different degrees, the extent to which either source contributes within a given experiment with conventional ChIP is unknown. In the absence of knowledge of the abundance of off-target binding, one cannot make a decision whether observed epitope abundance is significant or not, which in turn makes use of pull-down in medical diagnostics and research impractical. The inventors have found a method to quantitate IP efficiency of false positive and true positive epitopes in a pull-down assay in situ, which improves precision of data interpretation as Positive Predictive Value (PPV) may be readily calculated. PPV allows for an estimation of minimal abundance of epitope at a certain confidence level to be considered a true positive.

Using and the aforementioned methods of calculating IP efficiency and Standard IP efficiency, Positive Predictive Value (PPV) also referred to as Precision may be calculated. Knowledge of PPV streamlines any data analysis as it allows estimation of whether any difference in Protein Density is significant or not, which is not achievable with currently available methods and techniques.

$$\text{Precision} = PPV = \frac{\Sigma \alpha \cdot \eta_{TP}}{\Sigma \alpha \cdot \eta_{TP} + \Sigma \beta \cdot \eta_{FP}}$$

$\eta TP$ is IP efficiency of true positive epitope and $\alpha$ is a given weight of true positive epitope, $\eta FP$ is IP efficiency of false positive epitope, also known as off-target epitope and $\beta$ is a weight of false positive epitope. In the absence of prior knowledge of weight distribution $\alpha=\beta=1$. Other variants of this equation exist and use of knowledge of false positive and true positive epitope prevalence can be used in other applications.

There are two alternate ways to calibrate ChIP: global histone modification density calibration using an external standard and direct internal standard calibration. Like the relative internal standard approach that was predominantly employed in this work, these two can yield results expressed in "histone modification density" units, which are equal to apparent ratio of probed epitope to all other epitopes available in the given locus.

Global histone modification density calibration relies on a measurement of the total ratio of modification relative to the amount of histone, for example, knowing the percentage of all H3 that is K4 trimethylated. This global histone modification density, derived from either mass spectrometry or quantitative western blot measurements can be then redistributed among all IP peaks corrected for input depth in any given locus. The drawback of this method, apart from the sizable error in making the global abundance measurement (for example, MS accuracy plus the ambiguity of perhaps not observing all potential forms of the modification), is that such external measurements by orthogonal methodologies need to be made from the same nucleosomal sample used in the ChIP, and sample handling losses in both techniques are a considerable source of error. In particular, IP-efficiency is never 100% (in practice this can be considerably less), so the degree by which efficiency deviates from the theoretical maximum will be reflected in commensurately inflated values for apparent HMD.

Direct internal standard calibration measures the tag count of a spiked-in barcoded nucleosome standard through the ChIP process, knowing the precise molar concentrations of each internal standard ladder member in the input to extrapolate absolute molar abundance of probed epitope in the original sample. This sort of calibration is limited by the accuracy of counting the number of nuclei subjected to the micrococcal nuclease digest and biased loses that mount on the way from this well quantified number to exhaustively fragmented chromatin isolate. As we recover little more than 80% of the total nucleic acid from digested nuclei under highly optimized digest and isolation conditions, there is some systematic error due to biased genome recovery (Henikoff et al., 2009).

Yet another advantage of this embodiment is ability to deconvolute the true positive epitope signal from false positive epitope signal, presented here on the example of histone modification density, by solving the following matrix equation: A*x=b. For indicated datasets, ICeChIP-seq tracks were corrected for off-specificity by solving the following matrix equation: A*x=b, Another embodiment of the invention describes a method to deconvolute the true positive epitope signal from false positive epitope signal, presented here is the example of histone modification density, by solving the following matrix equation: A*x=b $$A = \begin{bmatrix} t_a^a & \cdots & t_z^a \\ \vdots & \ddots & \vdots \\ t_a^z & \cdots & t_z^z \end{bmatrix}, b = \begin{bmatrix} HMD_1^a & \cdots & HMD_n^a \\ \vdots & \ddots & \vdots \\ HMD_1^z & \cdots & HMD_n^z \end{bmatrix},$$

$$x = \begin{bmatrix} HMD(Cor)_1^a & \cdots & HMD(Cor)_n^a \\ \vdots & \ddots & \vdots \\ HMD(Cor)_1^z & \cdots & HMD(Cor)_n^z \end{bmatrix}$$

where, x is a matrix of corrected HMD scores, A is a matrix of correction factors and b is a matrix of non-corrected HMD scores, where, t is correction factor for specificity toward histone marks from the set of 'a' to 'z' histone marks (subscript), in the immunoprecipitation using antibody toward a histone mark from the set of 'a' to 'z' histone marks (superscript); HMD is histone modification density for a given histone mark ('a' to 'z') from the 1st to the nth locus; HMD(Cor) is corrected histone modification density for a given histone mark from the 1st to the nth locus, $$t_z^a = \frac{\frac{\Sigma_1^N IP_z^a}{\Sigma_1^N input_z}}{\frac{\Sigma_1^N IP_a^a}{\Sigma_1^N input_a}}$$

where, t is correction factor for specificity toward histone marks from the set of 'a' to 'z' histone marks (subscript), in the immunoprecipitation using antibody toward a histone mark from the set of 'a' to 'z' histone marks (superscript); HMD is histone modification density for a given histone mark ('a' to 'z') from the 1st to the nth locus; HMD(Cor) is corrected histone modification density for a given histone mark from the 1st to the nth locus, $$t_z^a = \frac{\frac{\Sigma_1^N IP_z^a}{\Sigma_1^N input_z}}{\frac{\Sigma_1^N IP_a^a}{\Sigma_1^N input_a}}$$

where, $\Sigma_1^N$ IP and $\Sigma_1^N$ input refer to abundance of the given barcode in the IP or in the input, superscript refers to histone mark toward which antibody was raised, while subscript refers to mark on the semisynthetic nucleosome that was pulled-down.

Disease Diagnosis

The main reasons why conventional ChIP assays have not been adopted in the clinic is that they are often irreproducible due to subtle handling differences and variable antibody specificity, making the % enrichment in the IP widely variant from experiment to experiment, and rendering unbiased comparisons problematic and unreliable. By virtue of having an internal standard that is subject to the steps of ChIP that are sensitive to variation, ICe-ChIP is far more robust in terms of replication and reliability of results, as demonstrated in FIGS. 6A, 6B, and 7A, and the numbers are readily compared as HMD is a universal, biologically relevant scale, made by direct in situ comparison to a well-defined internal standard.

Histone modifications and other epigenetic mechanisms are crucial for regulating gene activity and cellular processes. Different histone modifications regulate different processes, such as transcription, DNA replication, and DNA repair. Deregulation of any of these modifications can shift the balance of gene expression leading to aberrant epigenetic patterns and cellular abnormalities. For example, changes in histone post-translational modifications and variants have been detected in various cancers, and aberrant modification patterns are known to be drivers of disease in some cases (Daigle et al., 2011; Chi et al., 2010).

The present materials and methods can be used in the diagnosis, prognosis, classification, prediction of disease risk, detection of recurrence, selection of treatment, and evaluation of treatment efficacy for any disease associated with changes in histone post-translational modifications, including cancer in a patient, for example, a human patient. Such analyses could also be useful in conjunction with ex vivo culture of patient cells or induced pluripotency stem cells to assess the suitability of a given de-differentiation protocol for producing truly pluripotent stem cells, or the protocols for differentiating stem cells into specific cell types.

Any stage of progression can be detected, such as primary, metastatic, and recurrent cancer. Information regarding numerous types of cancer can be found, e.g., from the American Cancer Society (available on the worldwide web at cancer.org), or from, e.g., Harrison's Principles of Internal Medicine, (2005).

Certain aspects of the present invention provide methods for disease prognosis, such as estimating the likelihood of a patient developing cancer, classifying disease stages, and monitoring the efficacy of treatment in a patient with cancer. Such methods are based on the discovery that ICe-ChIP can be used to calibrate ChIP experiments to control for handling differences and antibody variability. Accordingly, by determining the level of a particular histone PTM (See, for example, Table 1) within a cell taken from the patient, including methylated histones as described herein, it is possible to determine whether or not the patient has a risk of developing a particular disease or has already developed a particular disease. For example, as described herein, quantification of histone PTM levels in cancerous tissues may be used for cancer prognosis or diagnosis.

In numerous embodiments of the present invention, the materials and methods described in certain aspects of the invention may be used to detect the levels of histone PTMs or variants in a biological sample at given genomic loci, thereby detecting the presence or absence of diseased cells in the biological sample. In some embodiments, the biological sample comprises a tissue sample from a tissue suspected of containing diseased cells, such as cancerous cells. Human chromatin DNA samples can be obtained by any means known in the art. In cases where a particular phenotype or disease is to be detected, histone-containing samples should be prepared from a tissue of interest, blood cells, or as appropriate, from cerebral spinal fluid. For example, histone-containing samples can be prepared from biopsy tissue to detect the histone PTM state associated with cancer.

As appropriate, the tissue or cells can be obtained by any method known in the art including by surgery. In other embodiments, a tissue sample known to contain cancerous cells, e.g., from a tumor, will be analyzed for the presence or quantity of histone PTMS at one or more of the histone PTM sites, such as those described in Table 1, to determine information about the disease, e.g., the efficacy of certain treatments, the survival expectancy of the individual, the presence of specific types of disease etc. In some embodiments, the methods may be used in conjunction with additional prognostic or diagnostic methods, e.g., detection of other disease markers, etc.

The materials and methods of certain aspects of the invention can be used to evaluate individuals known or suspected to have a disease, including cancer, or as a routine clinical test, e.g., in an individual not necessarily suspected to have a disease. Further diagnostic assays can be performed to confirm the status of disease in the individual.

Further, the present methods and materials may be used to assess the efficacy of a course of treatment. The efficacy of a treatment can be assessed by monitoring histone post-translational modifications or variant deposition using the methods and materials described herein over time in a mammal having a disease. For example, a reduction or absence of histone methylation in any of the methylation biomarkers as described herein in a biological sample taken from a mammal following a treatment, compared to a level in a sample taken from the mammal before, or earlier in, the treatment, indicates efficacious treatment. Detection of a histone PTM as described above can be used either alone, or in combination with other markers, for the diagnosis or prognosis of disease.

The materials and methods of certain embodiments can be used to determine the optimal course of treatment in a mammal with a disease. For example, the presence of methylated histone marks within certain methylation biomarkers as described herein or an increased quantity of methylation within certain of the methylation biomarkers can indicate a reduced survival expectancy of a mammal with cancer, thereby indicating a more aggressive treatment for the mammal. In addition, a correlation can be readily established between the presence, absence or quantity of methylation at a methylation biomarkers, as described herein, and the relative efficacy of one or another anti-cancer agent. Such analyses can be performed, e.g., retrospectively, i.e., by detecting methylation using the materials and methods described herein in one or more of the methylation biomarkers in samples taken previously from mammals that have subsequently undergone one or more types of anti-cancer therapy, and correlating the known efficacy of the treatment with the presence, absence or levels of methylation of one or more of the methylation biomarkers as described above.

In making a diagnosis, prognosis, risk assessment, classification, detection of recurrence or selection of therapy based on the presence, absence, or HMD of a particular histone PTM, the quantity of the PTM or variant may be compared to a threshold value that distinguishes between one diagnosis, prognosis, risk assessment, classification, etc., and another. For example, a threshold value can represent the degree of histone methylation that adequately distinguishes between cancer samples and normal biopsy samples with a desired level of sensitivity and specificity. With the use of ICe-ChIP the threshold value will not vary depending on the antibody used or the handling conditions. Threshold value or range can be determined by measuring the particular histone PTM of interest in diseased and normal samples using ICe-ChIP and then determining a value that distinguishes at least a majority of the cancer samples from a majority of non-cancer samples.

In some embodiments, the methods comprise recording a diagnosis, prognosis, risk assessment or classification, based on the histone PTM status determined from an individual. Any type of recordation is contemplated, including electronic recordation, e.g., by a computer.

Certain embodiments of the present invention provide for determination of histone post-translational modification status in a patient's cancer. The histone post-translational modification information may be used for cancer prognosis, assessment, classification and/or treatment. Cancers which may be examined by a method described herein may include, but are not limited to, renal cell carcinoma, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesothelioma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, glioma, or liposarcoma.

In certain embodiments the following diseases may be diagnosed using the present methods and materials: Bacterial infections caused by *Heliocobacter pylori, Listeria monocytogenes, Shigella flexneri, Anaplasma phagocytophilum,* Chlamdophila, Epstein-Barr Virus, herpes, HIV, *Schistosoma haematobium*; Obesity, diabetes, heart disease, autism, fragile X syndrome, ATR-X syndrome, Angelman syndrome, Prader-Willi syndrome, Beckwith Wiedemann syndrome, Rett syndrome, Rubinstein-Taybi syndrome, Coffin-Lowry syndrome, Immunodeficiency-centrometric instability-facial anomalies syndrome, α-thalassaemia, leukemia, Huntington's disease, schizophrenia, bipolar disease, aging, dementia, Alzheimer's disease, Parkinson's disease, Cornelia de Langue syndrome, Kabuki syndrome, Sjogren's syndrome, Vitiligo, progressive systemic sclerosis, psoriasis, primary biliary cirrhosis, Crohn's disease and ulcerative colitis, Hashimoto's thyroiditis, Grave's disease, inflammatory bowel disease, atherosclerosis, and cardiac hypertrophy.

Reagents and Kits

Another aspect of the invention provides reagents and kits including reagents for carrying out one of the methods described herein. The reagents may be included suitable packages or containers. The kit may include one or more reagents containing standards as described herein for the absolute quantification of true positive and false positive epitopes, for example in a pull-down assay or chromatin immunoprecipitation assay. The kit may also include at least one affinity reagent as described herein, for example an antibody. The standards may have native-like affinity, specificity and avidity for a true positive epitope. The kit can also comprise at least one standard with native-like affinity, specificity and avidity of epitope for false positive epitope.

In another preferred embodiment, the aforementioned standards include DNA-protein complexes comprising semi-synthetic nucleosomes, made with histones, histone isoforms or histone post-translational modifications with native-like affinity, specificity and avidity and a barcode molecule. In various embodiments, any variant of core histone sequences, which are known in the art, or post-translational modification, including those defined in Table 1, can be installed on the histones that comprise the histone octamer under presumption that native-like affinity, specificity and avidity of epitope is maintained. In a preferred embodiment, a set of standards is comprised of at least a single standard of DNA-complexes with native-like affinity, specificity and avidity of epitope for true positive epitope and multiple standard DNA-complexes with native-like affinity, specificity and avidity of epitope covering a range of possible off-target epitopes (false positive epitopes) present in the native pool of DNA-protein complexes.

In other embodiments, the kit may include one or more wash buffers, (for example, Phosphate buffered saline) and/or other buffers in packages or containers. In yet other embodiments, the kits may include reagents necessary for the separation of the captured agents, for example a solid-phase capture reagent including, for example, paramagnetic particles linked to a second antibody or protein-A. The kit may also include reagents necessary for the measurement of the amount of captured standard or sample.

When a kit is supplied, the different components may be packaged in separate containers and admixed immediately before use. Such packaging of the components separately may permit long-term storage without losing the active components' functions. Kits may also be supplied with instructional materials. Instructions may be printed on paper or other substrate, and/or may be supplied as an electronic-readable medium.

Example 1: H3K4Me3 Ice-ChIP-Seq of Mouse ESC E14 Cell Line

Figure 4:
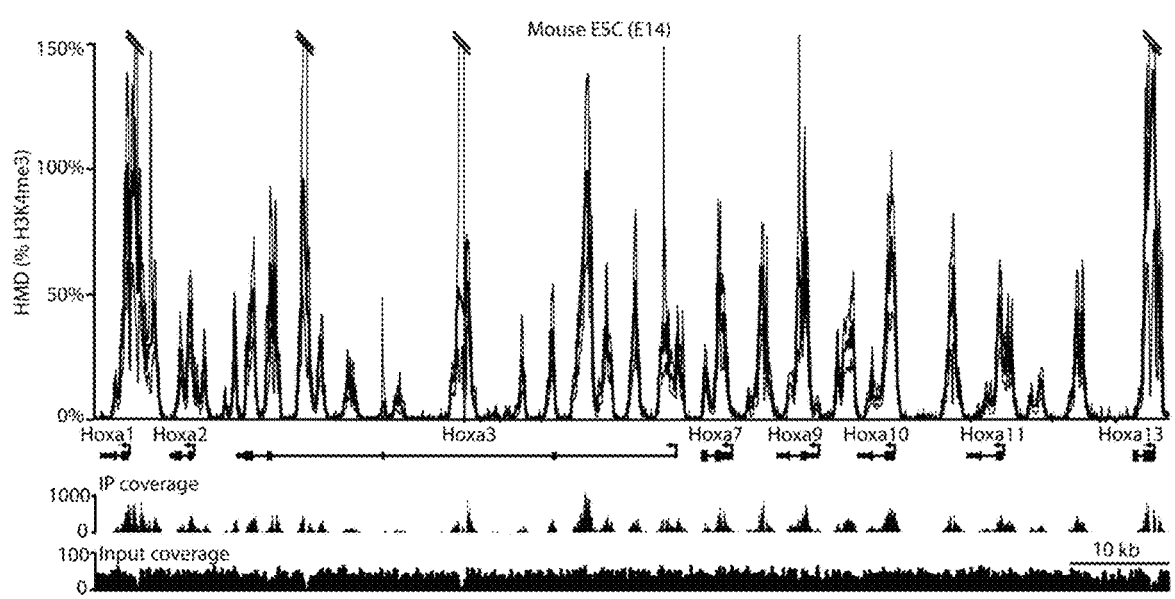
FIG. 4: The H3K4me3 ICe-ChIP-seq of mESCs E14 cell line shows Histone Modification Density to be within expected range. The top graph represents actual H3K4me3 Histone Modification Density for HOXA gene cluster in the mESC E14 cell line as a function of chromosomal coordinate for Chr6. ICeChIP coupled to Illumina paired-end sequencing reveals H3K4me3 modification density per base pair (HMD, darker line, 95% confidence interval, lighter line)) at the Hoxa gene cluster in the E14 mESC line as a function of chromosomal coordinate. Coding and non-coding genes are marked with bars and directional arrows below each graph. The small peaks below represent H3K4me3 ChIP signal (top) and input signal (bottom), expressed in raw read count.

To normalize chromatin immunoprecipitation to a biologically meaningful scale, we adapted the analytical chemistry concept of calibration by defined internal standards. We spiked-in reconstituted nucleosomes bearing a posttranslational modification that precisely resembles its native mononucleosomal counterpart isolated by micrococcal nuclease fragmentation in conventional native ChIP (Brand et al., 2008). FIG. 4 shows data for H3K4me3 ICe-ChIP-seq for HOXA gene cluster of mouse ESC E14 cell line. Histone Modification Density values lays within expected range (0-100%). As shown previously H3K4me3 is predominantly enriched at transcription start sites and enhancers.

In ICeChIP, such nucleosomal internal standards take the form of a "ladder" or concentration series of the same modified nucleosome, distinct only in short barcoded sequences that encode the relative concentration of each ladder member so that a calibration curve can be constructed. See FIG. 2.

Figure 2:
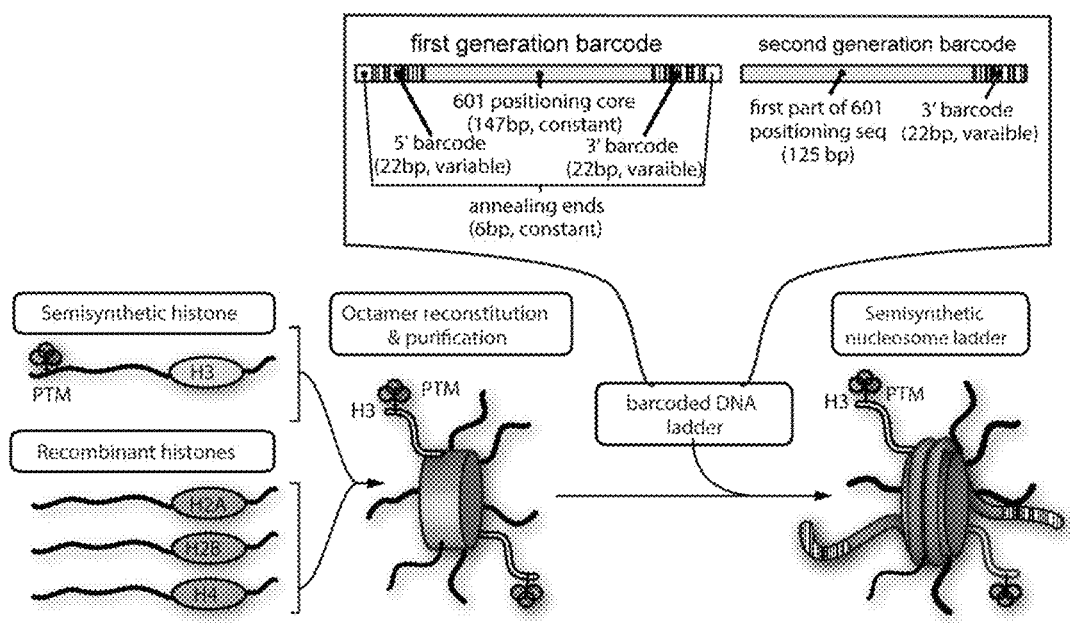
FIG. 2 illustrates the design and preparation of barcoded semisynthetic nucleosomes. Schematic depiction of the reconstitution of a semisynthetic H3K4me3 nucleosome ladder: histone octamers, produced by refolding equimolar core histones from recombinant and semisynthetic sources, are purified then mixed with equal amounts of barcoded ladder DNA. Schematic representation of barcoded nucleosome positioning DNA sequences based on the 601 positioning nucleosome sequence.
Figure 3:
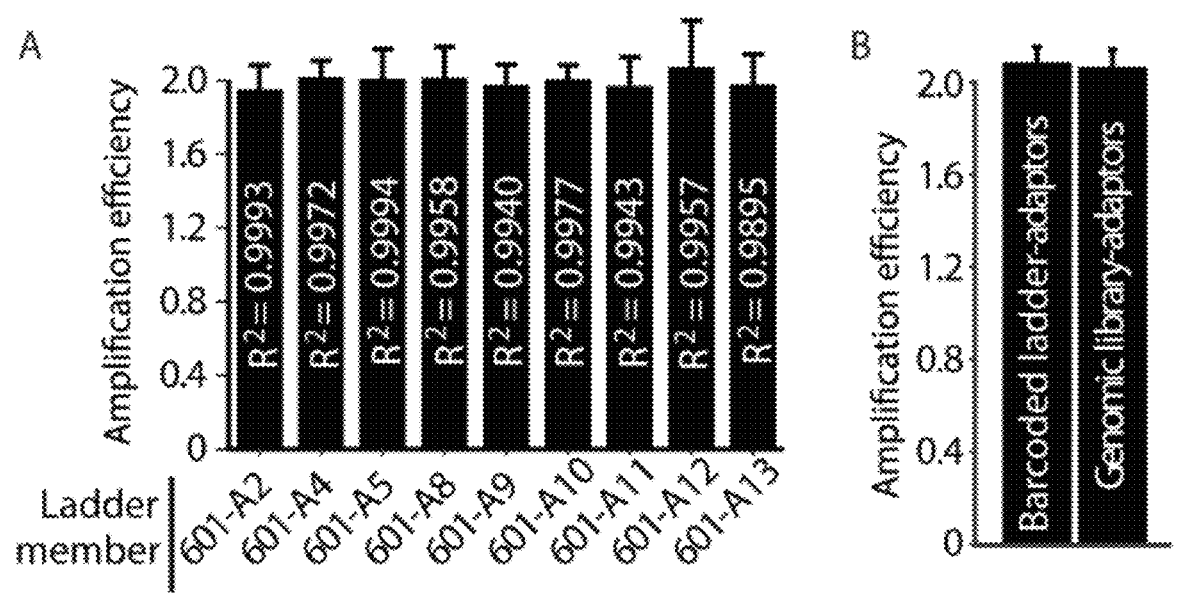
FIG. 3: (A) Amplification per cycle of barcoded ladder DNA is measured with qPCR utilizing a 2× serial dilution series fit by linear regression ($R^2$ of the fit displayed in each bar). (B) Amplification per cycle of all barcoded DNA ladder members versus native genomic DNA fragments after ligation of sequencing adaptors with primers that hybridize to these adaptors.

The second component of the nucleosomal internal standard is a set of barcoded DNA species that will stably associate with histone octamer upon reconstitution and can be readily distinguished from genomic sequences. We constructed a nine member DNA library composed of a constant "601" nucleosome-positioning sequence (Lowary and Widom, 1998) and variable flanking barcodes sequences selected to be both unique and devoid of PCR amplification artifacts relative to random DNA (FIG. 2). Barcode sequences were designed to be substantially different from the human, mouse and yeast genomes so that deconvolution of the internal standard ladder from genomic DNA sequences is robust to four or more base-calling errors in paired-end sequencing. Candidate barcodes were appended in pairs flanking the 601-core and further selected for clean single-band PCR product formation with high and equal amplification efficiency (FIG. 3A). As our ICeChIP analytical readouts entail PCR, either to prepare libraries for sequencing or to directly make the measurement (qPCR or ddPCR), we examined whether our ladder DNA displays any amplification bias relative to genomic DNA and found no detectable differences (FIG. 3B). We prepared the ICeChIP nucleosome ladder by gradient dialysis of histone octamer with a concentration series of different barcoded DNAs in a single tube (Luger et al., 1999; Ruthenburg et al., 2011) (FIG. 2).

We performed ICeChIP-seq by doping a nucleosome internal standard bearing the H3K4me3 mark into digested genomic chromatin prior to immunoprecipitation or pull-down. Here we present ICeChIP-seq data for E14 mouse embryonic stem cells (FIG. 4). We found that subtle improvements to the Dilworth protocol for native ChIP (Brand et al., 2008) maximized recovery of chromatin (>80% by qPCR) affording at least 95% pure mononucleosomes, and thereby minimized euchromatin bias. This native nucleosome population was then spiked with the internal standard ladder and subjected to hydroxyapatite chromatography purification prior to immunoprecipitation or pull-down. We quantified the number of nuclei prior to MNase digestion in order to stage our nucleosome ladder range around the genome copies represented so that our ladder concentration range is representative of a given native nucleosome. With miniscule quantities of ladder added (typically 0.0001-0.002% of total nucleosomes in the input), we do not appreciably undercut our sequencing depth, nor perturb native nucleosome capture. We subjected both the immunoprecipitated material and doped-input to Illumina sequencing; reads from the ladder and native nucleosomes were deconvoluted by alignment to the appropriate genome assembly concatenated with the internal standard DNA sequences.

As opposed to conventional ChIP, where the peak heights lack direct biological meaning, ICeChIP is able to calculate histone modification density (HMD %): the actual percentage of a mark's epitope present on a given chromosomal interval, with the bp resolution proper to ChIP-seq. With a good antibody, HMD % typically spans 0-100% but is not restricted to be in this range (FIG. 4). In ICeChIP-seq, the ratio of internal standard reads in the IP and input is a direct measure of IP enrichment, a value applied to the ratio of aligned native IP/input reads per base pair, genome wide (FIG. 1).

As a representative region of H3K4me3 enrichment, we present the HOXA/Hoxa gene clusters in mouse cells (Bernstein et al., 2006; Guenther et al., 2007; Mikkelsen et al., 2007) (FIG. 4). At this sequencing depth, significantly enriched peaks range in HMD between as little as 1% to over 100%. The error estimates spike asymptotically near the dyad of high-occupancy nucleosomes; as number of reads from these regions are low, the statistics of small numbers on a bp interval are a large source of experimental error. Greater input sequencing depth reduces the magnitude of the error, discernable by comparing the ~4-fold deeper sequencing (error$\propto 1/\sqrt{\text{depth}}$). Alternatively, HMD can be expressed over larger chromosomal intervals with reduced uncertainty. Importantly, these data are within a physically plausible range—apparent modification density rarely exceeds 100% within experimental error. In particular, of 60,530 called peaks in the mESC H3K4me3 dataset (MACS2, p<10-20), 18,300 of these have an HMD/bp value that exceeds 100% at any point within the peak, yet only 1627 have an HMD/bp value where the lower bound of the 95% confidence interval is greater than 100%. Nonetheless, we undertook a more careful appraisal of this method's validity in measuring histone modification density.

Figure 5:
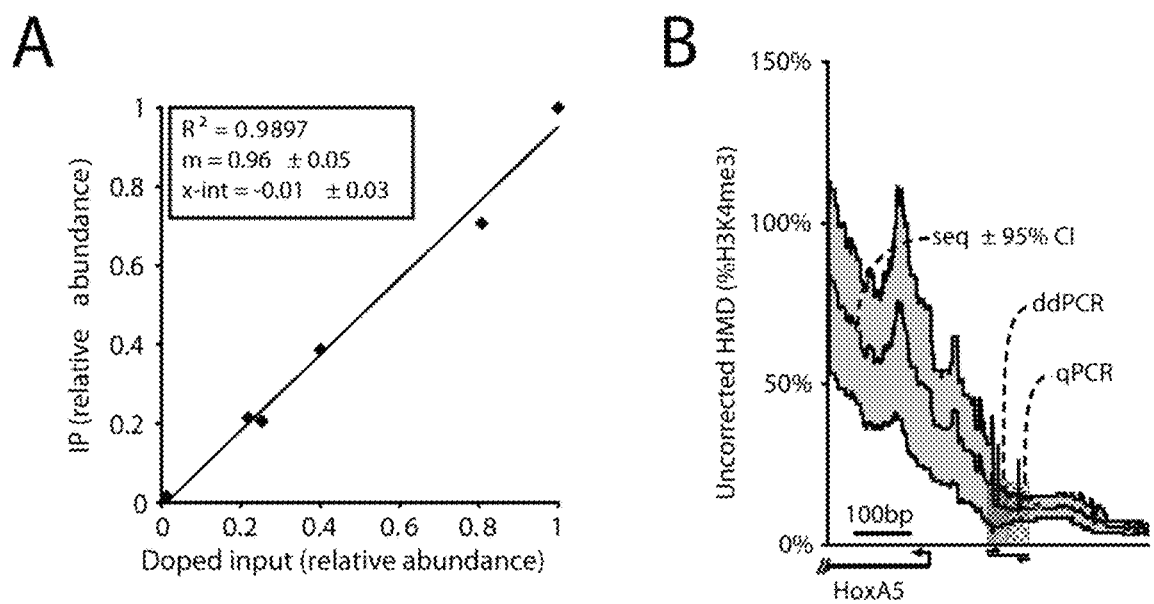
FIG. 5. A Critical examination of ICeChIP (A) The relative abundance of barcode tags normalized to the most abundant ladder member measured in IP and input from HEK293 H3K4me3 ICeChIP-seq. (B) ICeChIP-seq compared to ddPCR and qPCR: the middle line represents uncorrected H3K4me3 Histone Modification Density (HMD)±95% CI (top and bottom lines) in the mESC E14 cell line as a function of chromosomal windows. bars represent H3K4me3 measured by ddPCR and qPCR respectively on the same HMD scale (error bars are 95% CI), positioned over the indicated amplicon.
Figure 9:
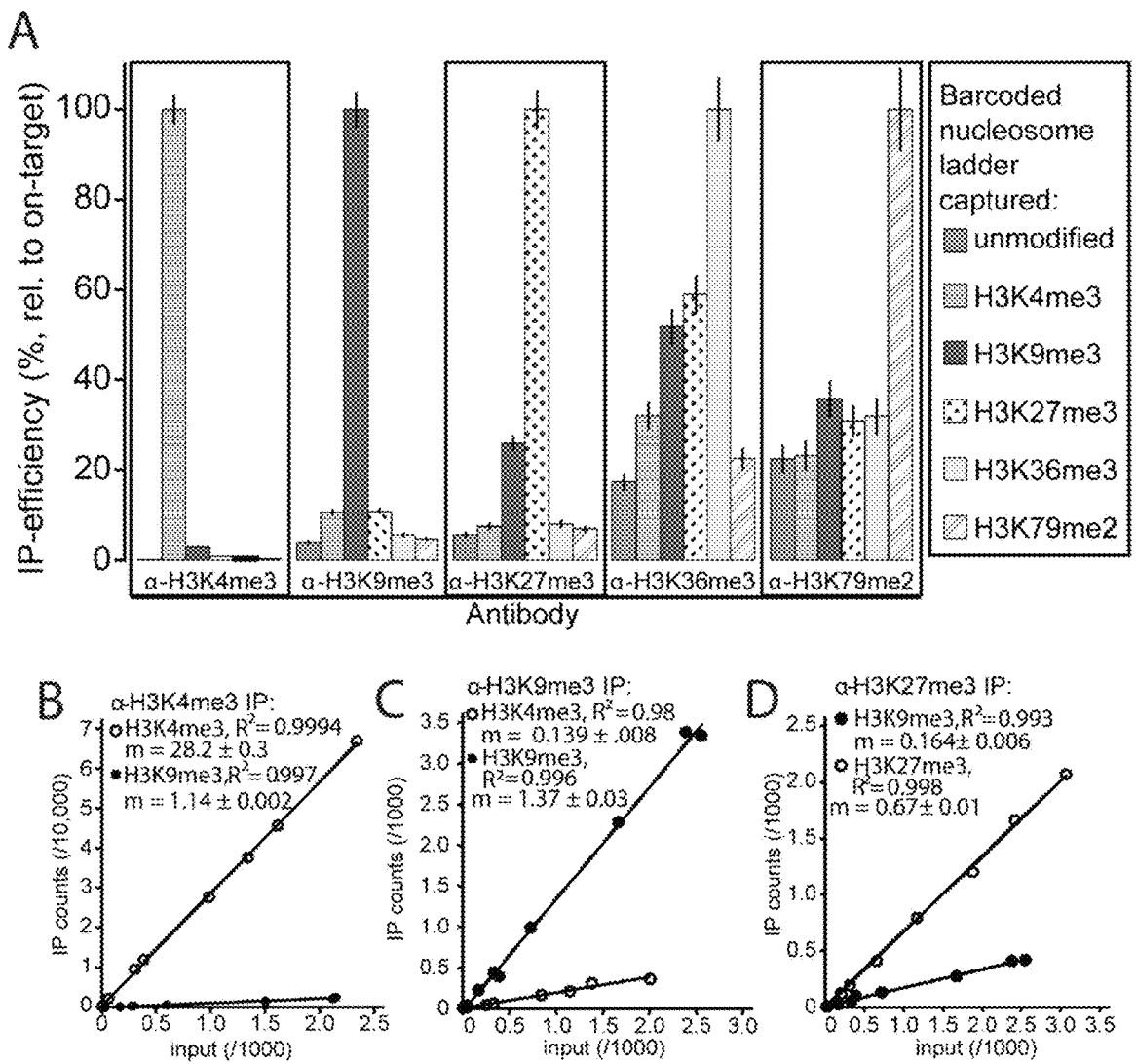
FIG. 9: ICeChIP with multiple internal standards reveals the specificity of the IP in situ. (A) A comparison of internal standard capture (unmodified, H3K4me3, H3K9me3, H3K27me3, H3K36me3, H3K79me2 barcoded nucleosome ladders simultaneously doped in equimolar concentration) in five multi-standard ICeChIP-seq experiments with antibodies to each of the methyl marks. The data, presented as relative IP-efficiency, normalized to the on-target ladder, permit facile comparison to potential off-target methylated nucleosomes, as well unmodified nucleosomes. (B) Calculation of IP-enrichment in multi-standard ICeChIP experiments from mESCs presented as raw ladder member read counts in the IP versus input for the on-target mark, as well as the highest off-target background ladders for H3K4me3 (Active Motif AM39159), (C) H3K9me3 (M309M3-A (Hattori et al., 2013)), (D) H3K27me3 (Millipore 07-449)

The behavior of internal standards in the course of performing the ICeChIP-seq measurements in FIG. 4 affords a direct assessment of precision. Linear regression of the observed relative abundances of each ladder member in the IP versus the input for our HEK293 ICeChIP directed against H3K4me3 revealed a marked correlation with a slope of 1.02±0.02 and an $R^2$ of 0.998 (FIG. 5A). Additional independent experiments revealed similarly striking linearity indicative of very high precision with no apparent systematic deviations suggesting that each ladder member displays equivalent IP-enrichment (FIG. 9B-D). These experiments represent the first demonstration that there can be a linear relationship between the amount of epitope and corresponding ChIP-signal intensity. Such linearity is a requirement for using scalar factor correction in ICeChIP, and therefore is routinely examined for strict linearity prior to applying ICeChIP scaling. In our experiments this linearity exists through a useful working range as we have staged the concentration series of nucleosomal internal standards in approximately the same range of the number of nuclei in the experiment. We sought ways to compare HMD/bp computed from Illumina sequencing to other quantitative DNA counting methods. Digital droplet PCR (ddPCR) and quantitative PCR (qPCR) rely on amplicons defined by specific primer sets, so that HMD/bp derived from ICeChIP-seq averaged over the chromosomal interval of the amplicon may be directly compared. To our surprise, we found a 5.7-fold enrichment of DNA fragments larger than mononucleosomes in our IP relative to input by paired-end sequencing, leading to ~16% inflation of apparent HMD. We refer to this overrepresentation as an "oligonucleosome avidity bias", which we believe stems from a higher valence of epitope per DNA fragment. As a correction, we typically filter raw paired-end sequencing data to remove DNA larger fragments. However, measurements made with qPCR and ddPCR cannot distinguish between mononucleosome and oligonucleosome-derived signal without stringent size selection. Thus, for comparison purposes we display the uncorrected HMD signal (FIG. 5B), and provide the mononucleosome-corrected HMD in the supplemental information. With this analysis, the three methods of measurement were identical within experimental error at HoxA5 lociin mESCs. (FIG. 5B). Further, we performed ICeChIP with antibodies for histones H3 and H4 and found the expected ~2:2 ratio in nucleosomes to be indistinguishable for all three measurement modalities. This congruence suggests that either the ICeChIP is accurate or harbors systematic error independent of the method of DNA quantification.

Semi-Synthetic Histone Preparation

Human histone H3.2(C110A)K4me3 was made by semisynthesis (Ruthenburg et al., 2011; Shogren-Knaak and Peterson, 2003), but distinct in one critical respect—the ligation junction is scarless following a desulfurization step (Wan and Danishefsky, 2007)—the resulting histone is identical to the native modified histone save for the C110A mutation that is frequently made to ease of handling in recombinant histone. The sequence corresponding to residues 1-20 of histone 3, bearing the K4me3 modification was synthesized as a peptide thioester by Boc-chemistry SPPS on S-trityl-β-mercaptopronionyl-β-methyl-benzhydrylamine resin (Nova Biochem)(Alewood et al., 1997). Resin was swelled for 1 hour with DMF and subsequently deprotected by washing it three times for three minutes with 95% TFA, 2.5% triisopropylsilane, and 2.5% $H_2O$. All amino acid couplings were performed with 4 molar equivalents of Boc-protected amino acid, 3.9 molar equivalents of HBTU and 6 molar equivalents of DIPEA incubated with resin for 10 minutes under nitrogen agitation. Following coupling, the resin was washed three times with DMF (with exception of glutamine where DCM was used instead), and Boc deprotection effected with three washes of TFA, where the first one is a flow wash. After last amino acid deprotection, the resin was washed sequentially with DMF, DCM and methanol. All peptides were cleaved off of resin with HF/DMS/anisole (10:1:1), precipitated with cold diethyl ether and lyophilized.

Truncated histone H3.2A20 (C10A) was expressed recombinantly with $His_6$-tag at N-terminus and a TEV protease cleavage site (ENLYFQ^C) inserted after position H3.2L20, replacing A21, so that upon TEV protease cleavage, an N-terminal cysteine is released. The C-terminal peptidyl thioester described above was ligated to the recombinant histone H3.2A20-A21C fragment through native chemical ligation (Dawson et al., 1994), using the MPAA ligation auxiliary (Johnson and Kent, 2006). Briefly, equimolar amounts of peptidyl 3-mercaptopropionamide thioester and truncated histone were mixed at 2 mM final concentration in NCL buffer (6M Guanidinium chloride, 200 mM phosphate pH 7.0) in the presence of 30 mM MPAA and 20 mM TCEP. If needed pH was adjusted to 7.0 and reaction was incubated for 12-16 hrs at room temperature. Subsequently, the completion of reaction was validated with MALDI MS and product was purified by semipreparative HPLC (column YMC pack C8, 250 mm*10 mm, 5 µm, 30 nm). The native alanine at position 21 was restored by radical-mediated desulfurization of cysteine (Wan and Danishefsky, 2007). The completion of reaction was validated by ESI MS, purified by semipreparative HPLC (YMC pack C8, 250 mm*10 mm, 5 µm, 30 nm) and subsequently lyophilized.

Octamers were prepared on 250-500 µg scale as previously described (Luger et al., 1999; Muthurajan et al., 2003), using human histones expressed in E. coli (Ruthenburg et al., 2011). Briefly, equimolar core histones were mixed in unfolding buffer (50 mM Tris-HCl pH 8, 6.3 M Guanidine-HCl, 10 mM 2-mercaptoethanol, 4 mM EDTA) to final concentration of total histone >1 mg/mL, and dialyzed against two changes of 500 volumes of refolding buffer (20 mM Tris-HCl pH 7.8, 2M NaCl, 1 mM EDTA, 5 mM DTT) over 16 hours in 3500 MWCO SnakeSkin dialysis tubing (Pierce) at 4° C. Following dialysis and centrifugation to remove any precipitated material, the soluble fraction of crude octamer was subjected to gel filtration chromatography (Superdex 200 10/300 GL, GE Healthcare) resolved in refolding buffer. Fractions containing pure octamer were pooled and concentrated with Amicon Ultra-4 centrifugal filters (10 k MWCO, Millipore) to a final concentration of 5-M (measured spectroscopically, $\varepsilon_{280nm}$=44700 M$^{-1}$ cm$^{-1}$, blanked with concentrator flow-through).

DNA for nucleosome reconstitution is based on "601-Widom" nucleosome positioning sequence (Lowary and Widom, 1998). To each end of 601 sequence we have appended 22 bp barcode sequences—each composed of two catenated 11 bp sequences absent in human and mouse genome (Herold et al., 2008)—flanked by constant 6 bp of linker DNA.

Nucleosomes were reconstituted by mixing equimolar histone octamer and DNA to final concentrations of 1 µM, them dialyzing this solution in dialysis buttons (Hampton Research) against a non-linear gradient starting with 2M NaCl and ending at 200 mM NaCl over the course of 12-16 hours in buffer containing 20 mM Tris-HCl pH 7.5, 1 mM EDTA, 10 mM 2-mercaptoethanol (Ruthenburg et al., 2011). Subsequent to dialysis, semi-synthetic nucleosomes were diluted 1:1 with 2× storage buffer (20 mM Na-Cacodylate pH 7.5, 10% v/v glycerol, 1 mM EDTA), 1×RL Protease Inhibitor Cocktail [1 mM PMSF, 1 mM ABESF, 0.8 µM aprotinin, 20 µM leupeptin, 15 µM pepstatin A, 40 µM bestatin, 15 µM E-64], 200 µM PMSF and kept at 4° C. The concentration of nucleosomes was measured in triplicate by stripping DNA with 2M NaCl and measuring concentration of DNA by densitometry of ethidium bromide-stained agarose gels calibrated in situ with the Thermo Scientific MassRuler Low Range DNA Ladder. Working concentrations of semi-synthetic nucleosomes were prepared by dilution to desired concentrations in long-term storage buffer (10 mM Na Cacodylate pH 7.5, 100 mM NaCl, 50% Glycerol, 1 mM EDTA, 1×RL Protease Inhibitor Cocktail, 200 µM PMSF) and stored at −20° C.

ICeChIP

The ICeChIP protocol is a pull-down protocol like a native ChIP protocol (Brand et al., 2008). Plate-adhered cells (~10$^7$ cells per IP) were washed twice with 10 mL of PBS, and released by 5 mL Accutase (Millipore) for 5 minutes in 37° C., quenched with 2 mL of complete media, and collected by centrifugation (500×g, for 5 minutes at 4° C.). All subsequent steps were performed on ice with ice-cold buffers. Cells were washed twice with 10 mL PBS, and twice with 5 mL of Buffer N (15 mM Tris pH 7.5, 15 mM NaCl, 60 mM KCl, 8.5% (w/v) Sucrose, 5 mM MgCl$_2$, 1 mM CaCl$_2$ 1 mM DTT, 200 µM PMSF, 1×RL Protease Inhibitor Cocktail). Cells were resuspended in 2 PCVs (packed cell volumes) of Buffer N and lysed by adding 2 PCV of 2×Lysis Buffer (Buffer N supplemented with 0.6% NP-40 substitute (Sigma)) for 10 minutes at 4° C. Nuclei were collected by centrifugation (500×g for 5 minutes at 4° C.) and were resuspended in 6 PCVs of Buffer N. To remove cell debris, resuspended nuclei were overlaid on the surface of 7.5 mL of sucrose cushion (10 mM HEPES pH 7.9, 30% (w/v) sucrose, 1.5 mM MgCl$_2$) in a 50 mL centrifuge tube centrifuged (1300×g, Sorvall Legend XTR swinging bucket rotor for 12 minutes at 4° C.). Most cell debris remained in upper layer while nuclei sedimented through the sucrose cushion and pelleted on the bottom of the tube. The supernatant was discarded and nuclei were resuspended in 2 PCVs of Buffer N. To measure apparent concentration of chromatin, 2 µL of resuspended nuclei were diluted in 98 µL of 2M NaCl in triplicate, total nucleic acid absorbance was measured at 260 nm by Nanodrop (Thermo Scientific), and the conversion factor assuming 1A$_{260}$=50 ng/µL of chromatin employed. Based on these measurements, apparent concentration of chromatin was adjusted to 1 µg/µL with Buffer N. The quantity and quality of nuclei were also assessed using a hemocytometer.

At this stage, a ladder of semisynthetic nucleosomes was doped into the pool of native nucleosomes. The amount of spiked ladder was comparable to estimated amount of genome copies in the pool based on the nuclei counting times the average DNA content per cell (~2.5 copy of genome per cell).

To remove debris coming from nuclei lysis and MNase digestion as well as strip chromatin bound factors, the pool of nucleosomes was subjected to hydroxyapatite chromatography purification (Brand et al., 2008). Fragmented chromatin with internal standard ladders were split into 100 µg total nucleic acid fractions and each fraction was mixed with 66 mg of hydroxyapatite (HAP) resin (Bio-Rad Macro-Prep® Ceramic Hydroxyapatite Type I 20 µm) rehydrated with 200 µL of HAP buffer 1 (3.42 mM Na$_2$HPO$_4$ and 1.58 mM NaH$_2$PO$_4$ final pH 7.2, 600 mM NaCl, 1 mM EDTA, 200 µM PMSF), incubated for 10 minutes at 4° C. on rotator and subsequently was applied to the centrifugal filter unit (Millipore Ultrafree® MC-HV Centrifugal Filter 0.45 µm). The chromatin-loaded resin in the column was drained and then washed four times with 200 µL HAP buffer 1 and four times with 200 µL of HAP buffer 2 (3.42 mM Na$_2$HPO$_4$ and 1.58 mM NaH$_2$PO$_4$ final pH 7.2, 100 mM NaCl, 1 mM EDTA, 200 µM PMSF) by centrifugation (600×g, 1 minute at 4° C. in fixed angle rotor. Nucleosomes were eluted from the HAP column with three 100 µL washes of HAP elution buffer (342 mM Na$_2$HPO$_4$ and 158 mM NaH$_2$PO$_4$ final pH 7.2, 100 mM NaCl, 1 mM EDTA, 200 µM PMSF). To measure apparent concentration of HAP purified chromatin fragments, 10 µL of HAP elution was diluted in 40 µL of 2M NaCl in triplicate, and absorbance measured at 260 nm averaged and adjusted (1A$_{260}$=50 ng/µL of chromatin). Apparent concentration of chromatin was adjusted to 20 µg/mL with ChIP Buffer 1(25 mM Tris pH 7.5, 5 mM MgCl$_2$, 100 mM KCl, 10% (v/v) glycerol, 0.1% (v/v) NP-40 substitute).

H3K4me3 ChIP was performed with 10 µg of chromatin and 15 µL of AM39159 antibody, H3 and H4 ChIP was performed with 1 µg of chromatin and 15 µL of AM61277 and AM61299 antibody, respectively (Active Motif). 10% of initial chromatin for each IP was set aside to serve as ChIP input. Each IP experiment used 50 µL of Protein A Dynabeads (Invitrogen) that were washed twice with 1 mL of ChIP buffer 1 with 1 min collection on magnetic rack after each wash. To prepare the resin, 15 µL of antibody and 85 µL of ChIP buffer 1 was added to Protein A Dynabeads and incubated for 10 minutes at room temperature on a rotator, then washed twice with 1 mL of ChIP Buffer 1. Chromatin (10 µg unless otherwise indicated) in 500 µL of ChIP buffer 1 was then added to magnetic beads and incubated for 15 minutes at room temperature on rotator. Beads were washed 3 times with 1 mL of ChIP Buffer 2 (mM Tris pH 7.5, 5 mM $MgCl_2$, 300 mM KCl, 10% (v/v) glycerol, 0.1% (v/v) NP-40 substitute), then twice with ChIP buffer 3 (10 mM Tris pH 7.5, 250 mM LiCl, 1 mM EDTA, 0.5% Na-Deoxycholate, 0.5% (v/v) NP-40 substitute), each wash consisting of a 10 minute rotating incubation and 1 minute collection on magnetic rack at 4° C. During the course of washing, at least two tube changes reduced non-specific background. Beads were then rinsed with 1 mL of ChIP Buffer 1 and 1 mL of TE buffer, followed with two 200 µL ChIP elution buffer steps (50 mM Tris pH 7.5, 1 mM EDTA, 1% w/v SDS). Each elution step consisted of 10 minute incubation at 65° C. in a Thermoshaker (Eppendorf) at 900 rpm. Elutions were combined and ChIP elution buffer was added to inputs to match volume of ChIP elutions. After adjusting the buffer to 200 mM NaCl, 100 ng of RNase A was added into the mixture and incubated at 65° C. for 45 minutes in Thermoshaker at 800 rpm, and terminated with 10 mM EDTA. Next, protein digestion was accomplished with 20 ug of proteinase K (Roche) for 2 hrs at 42° C. in the Thermoshaker at 800 rpm. DNA was recovered and purified with Qiaquick columns (Qiagen): 6 volumes of PB buffer were added to the digestion and this solution applied to the column (17900×g, 30 s) followed by 3×750 µL of PE buffer washes (17900×g, 30 s) with an extra 1 minute spin to remove residual ethanol. DNA was eluted by applying two times 25 µL of TE buffer at 50° C. and centrifuging (17900×g, 1 min).

Illumina Library Preparation

For library preparation 10 ng of DNA isolated from IP or input was used. In cases in which the total amount of DNA was below 10 ng, all available DNA was subjected to library preparation. Ends of DNA were blunted using the End-it™ DNA End-Repair Kit (Epicentre) (7 µL 10× End-It buffer, 7 µL 2.5 mM dNTP Mix, 7 µL 10 mM ATP, 1.4 µL of End-Repair Enzyme Mix and 47.6 µL of DNA in TE buffer, incubated for 45 minutes at room temperature. DNA was purified with 126 µL (1.8 volume) of Ampure XP Beads (Beckman Coulter). Beads were mixed with End repair mixture by pipetting 10 times up and down followed by 5 minutes incubation at room temperature. Magnetic beads were collected on side of the tube by magnet and two 30 sec 250 µL 80% EtOH washes on magnet were performed. Tubes were removed from the magnetic rack and 34 µL of TE buffer was added to beads and pipetted 10 times up and down. Magnetic beads were not removed from elution and remained in the tube during A-tailing. Addition of single adenosine to 3' ends of DNA was accomplished by adding to 5 µL NEB buffer 2, 10 µL 1 mM dATP, 1 µL Klenow fragment (3'→5' exo-, NEB) to the End-repaired DNA, and with incubation at 37° C. for 30 minutes. To purify DNA, 110 µL (2.2 volume) of SPRI Buffer (20% PEG6000, 2.5M NaCl) was added to the reaction and was pipetted 10 times up and down followed by 5 minutes incubation at room temperature. Magnetic beads were collected on side of the tube with magnet and two 30 sec 200 µL 80% EtOH washes on magnet were performed. Tubes were then taken out of magnetic rack and 13 µL of TE buffer was added to beads and mixed by pipette. Magnetic beads were not removed from elution and remained in the tube during adaptor ligation. To ligate adaptors, the following mixture was prepared: 2× Quick DNA ligase buffer, 2 µL 2 µM of adaptor duplex, 1 µL of Quick DNA ligase (NEB) and added to 13 µL of A-tailed DNA. The reaction was incubated for 15 minutes at room temperature. To purify DNA, 21 µL (0.7 volume) of SPRI Buffer was added to the reaction and was pipetted 10 times up and down followed by 5 minutes incubation at room temperature. Magnetic beads were collected via magnet and washed twice with 30 sec 200 µL 80% EtOH incubations, and eluted with 46 µL of TE buffer. The supernatant was transferred to the new siliconized tube.

Quantitative-PCR was run to estimate minimal number of PCR cycles to amplify DNA library. 7.15 µL of H2O, 1 µL of 10×AccuPrime PCR buffer II, 0.25 µL of 20×EvaGreen® dye (Biotum) to final 0.5× dilution, 1 µL of DNA library, 0.2 µL of 25 µM MP_PCR_Primer1, 0.2 µL of 25 µM MP_PCR_Primer2, and 0.2 µL AccuPrime Taq DNA Polymerase (Invitrogen #12339-016). Bio-Rad CFX384 qPCR machine program was set to: 1-95° C. for 5 min, 2-95° C. for 80 s, 3-65° C. for 90 s—read at the end, 4—go back to step 2 for 24 times. Based on the readings, cycle number to amplify library was set to $C_t$+3 cycles. If the $C_t$ value observed was below 7 cycles, the template was diluted 10 fold and procedure were be repeated.

DNA library was amplified by mixing: 40 µL of DNA library, 5 µL 10×AccuPrime PCR buffer II, 1 µL 25 µM MP_PCR_Primer1, 1 µL 25 µM MP_PCR_Primer2_INDEX, 1 µL AccuPrime Taq DNA Polymerase, and 2 µL of $H_2O$, followed by thermal cycling in a C1000 (Bio-Rad). The machine was set to: 1-95° C. for 5 min, 2-95° C. for 80 s, 3-65° C. for 90 s, 4—go back to step 2 for number of cycles determined with qPCR ($C_t$+3 cycles). Amplified DNA was purified with 90 µL (1.8 volume) of Agencourt Ampure XP Beads. Beads were mixed with PCR mixture by pipetting 10 times up and down, followed by 5 minutes incubation at room temperature. Magnetic beads were collected on the side of the tube via magnet and two 30 s 250 µL 80% EtOH washes on magnet were performed. The tube was removed from the magnetic rack and 25 µL of TE buffer was added to beads and pipetted 10 times up and down. Magnetic beads were collected on the side of the tube and supernatant was moved to new siliconized tube. Size distribution and concentration of amplified library was assessed with Agilent Technologies 2100 Bioanalyzer.

Sequencing and Data Analysis

Cluster generation and sequencing was performed using the standard Illumina protocol for Illumina HiSeq 2500 by the University of Chicago Functional Genomics core facility. Data analysis was performed with Galaxy(Blankenberg et al., 2010; Giardine et al., 2005; Goecks et al., 2010). Raw reads in FastQ fromat were first submitted to FastQ Groomer. Reads were mapped with Bowtie2 (Langmead et al., 2009) (sensitive preset option, end-to-end alignment), depending on organism of origin, to mouse (MM10) reference genomes with sequences of barcodes catenated at the end (each barcode with its own entry). Resulting SAM files were then filtered using SAMtools (Li et al., 2009). Reads that were unmapped, unpaired (distance >1000 bp) and paired in wrong pair were removed from the set by this data analysis pipeline. To remove noise coming from low quality reads and contaminants as well to mask repeatable genomic sequences, reads with mapping quality lower than 20 were removed. To avoid signal artifacts and not distort Poisson sampling statistics paired reads were merged together into single entries (overlapping fragments were flattened and gaps were filled). To avoid oligonucleosome avidity bias, reads longer than 220 bps were removed, except where explicitly stated otherwise. BEDTools (Quinlan and Hall, 2010) was used to create genome coverage bedgraphs.

In order to get high precision we have aimed to achieve IP coverage ranging between 1000 and 10 reads of depth and average depth of input to be at least ~20. However, the deeper input sequencing the better, as it is limiting factor for precision. In order to compute barcode IP efficiency, we calculated the ratio of integrated coverage over the whole sequence of each barcode in IP over the input.

$$\text{IP efficiency} = \frac{\Sigma_1^n IP}{\Sigma_1^n \text{input}}$$

where, n is the length of barcoded construct, in this case it is 203 bp, IP is integrated counts for IP and input is integrated counts for input.

To increase accuracy, we have averaged the barcode IP efficiency values for multiple barcodes. To calculate Histone Modification Density (HMD) we have applied the following equation to genome coverage information for IP and input:

$$\text{HMD (per/bp)} = \frac{\left(\frac{IP}{\text{input}}\right) \cdot 100\%}{IP \text{ efficiency}}$$

To estimate HMDs confidence intervals 95% we have applied following equation:

$$CI^{95\%}_{HMD\left(\frac{per}{bp}\right)} \cong 1.96 * \sqrt{\left(\frac{100\% * \sqrt{IP}}{\text{input} * IP \text{ efficiency}}\right)^2 + \left(\frac{100\% * IP * \sqrt{\text{input}}}{\text{input}^2 * IP \text{ efficiency}}\right)^2}$$

Here we assume that standard deviation of efficiency is negligible, and sampling of reads in IP and input follows Poisson Sampling statistics. To calculate total HMD content genome-wide (percent of all nucleosomes in all genomic loci bearing modification), HMD signal was integrated and subsequently divided by total number of base pairs for which we had genome coverage or alternatively by reported total genome size.

Example 2: Validation of ICeChIP-Seq: Reproducibility and Robustness

Figure 6:
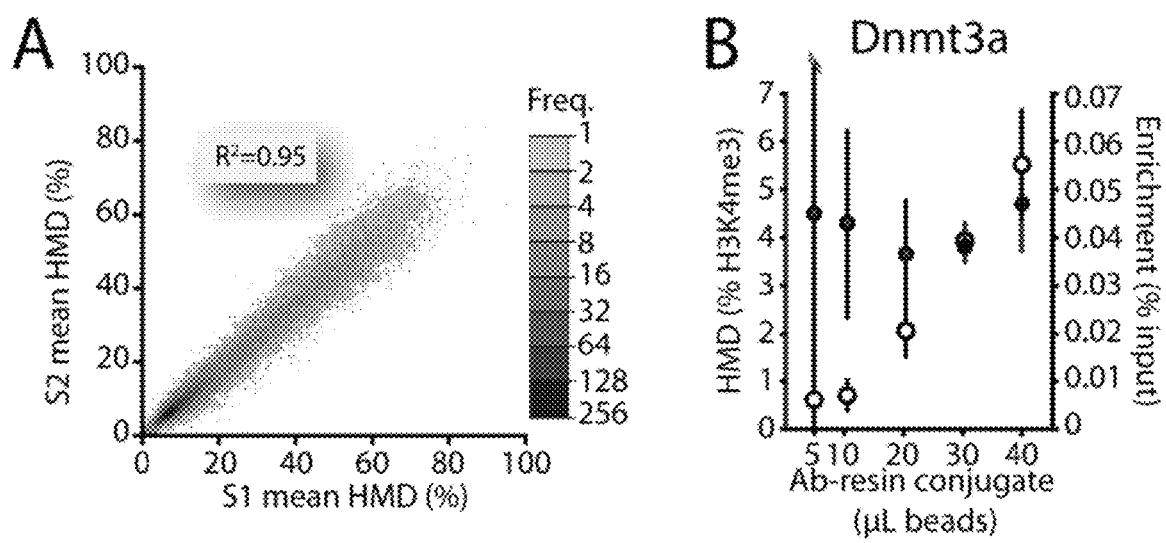
FIG. 6: ICeChIP is highly reproducible and more robust to experimental differences than conventional ChIP (A) Scatter plot comparison of the two samples (S1 and S2) via plotting the mean mononucleosome HMD (% H3K4me3) for called peaks at the same loci. (B) Measurement of HMD (% H3K4me3) versus enrichment (% IP/input, representing the conventional way of presenting ChIP data) at the DNMT3a locus by ICeChIP-qPCR in mESCs as a function of antibody-resin conjugate with fixed 10 µg of chromatin input.

To examine the consistency of ICeChIP upon replication we repeated the H3K4me3 ICeChIP-seq in mESCs and observed tight coupling of HMD tracks. Correspondingly, mean HMD values for each biological replicate at called peaks are highly correlated ($R^2=0.95$) and the distribution is within the estimated error (FIG. 6A).

Figure 7:
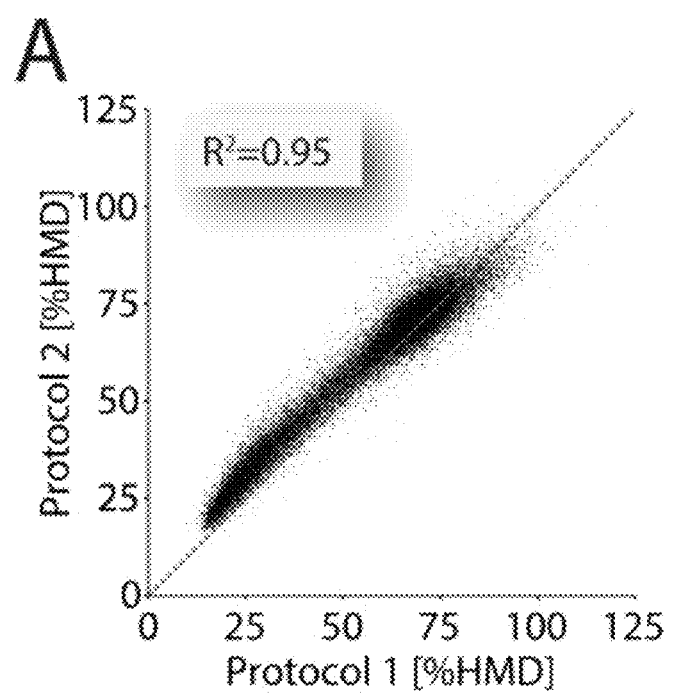
FIG. 7: The reproducibility and robustness of ICeChIP. (A) Comparison of two H3K27me3-directed ICeChIP experiments from *Drosophila* S2 cells, staged from the same input but with great variation in IP and washes. Sample 1 data was generated using our standard ICeChIP conditions (15 minute incubation of resin-Ab conjugate with input, followed by five washes over 50 minutes) whereas the Sample 2 IP was performed with a shorter incubation and flow washes of the resin with the same volumes applied over the span of one minute. Each data point corresponds to mean H3K27me3 averaged over 3000 bp non-overlapping window (N=41158); windows with insufficient input depth were excluded from analysis (cut-off>5). Data pooled from technical triplicates for each protocol (independent IPs and measurements).
Figure 8:
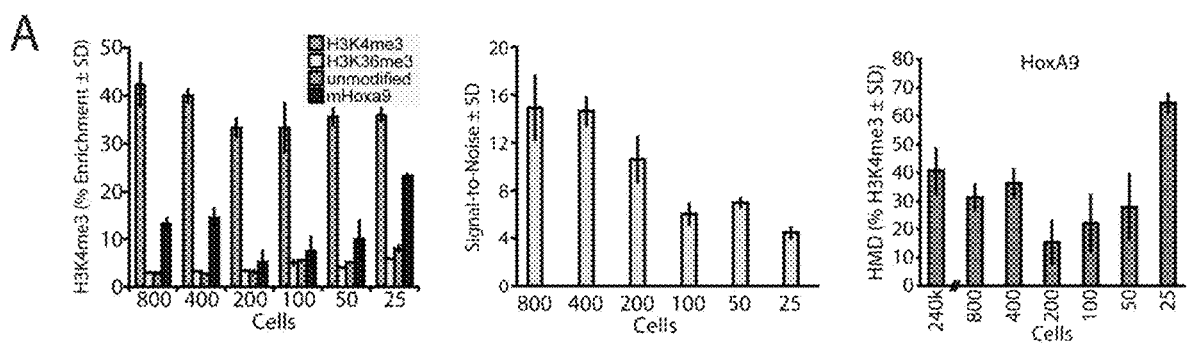
FIG. 8: ICeChIP with multiple internal standards. Chromatin input titration for a small scale ICeChIP experiment as presented in FIG. 9. The method works well down to the chromatin equivalent of 400 cells.

Variation of IP enrichment as a consequence of different experimental handling conditions is a major complicating factor in the reproducibility of conventional ChIP (Marinov et al., 2014). By tethering the output values of each experiment to a defined internal standard, HMD measured by ICeChIP is more tolerant of experimental variation. As apparent ChIP enrichment is a function of the amount of input chromatin relative to the number of epitope binding sites on the resin, we sought to simulate experimental handling disparities by manipulating the ratio of input relative to resin-immobilized antibody. In a linear staging regime, we examined H3K4me3 HMD via ICeChIP-qPCR and found that it is independent of the amount of input, traceable to relatively uniform IP enrichment of H3K4me3 at the GAPDH locus. Although these experiments confirmed that HMD is consistent over a typical ChIP input range, we sought experimental conditions that yielded differential enrichment. For a fixed amount of input, altering the amount of resin-immobilized antibody used in the immunoprecipitation produced a range of IP efficiencies greater than 6-fold, yet H3K4me3 density computed from these experiments for the Dnmt3A and Hoxa9 locus was identical within experimental error (FIG. 6B). Similarly, radical alteration of binding and wash conditions during ICeChIP-seq afford very similar HMD measurements (FIG. 7A). Finally, we titrated down the input quantity to examine the performance of ICeChIP near the limits of low-cell number protocols, and found it to perform stably down to the input equivalent to ~ 400 cells (FIG. 8). Collectively, these data indicate that while IP enrichment may vary as a function of the experimental conditions, HMD is stable and highly reproducible.

Example 3: Multiple Ladder ICeChIP Measures IP Specificity In Situ

Apparent ChIP signal is an admixture of on-target capture, off-target capture of related epitopes (for example other lysine methyl marks) and non-specific adhesion of nucleosomes to the antibody resin. ICeChIP performed with several different types of internal standards measures all three of these possible sources of ChIP signal, thereby critically addressing the true signal and error of a ChIP for the first time. We queried mESC nucleosomes doped with three types internal standards, H3K4me3, H3K36me3, and unmodified nucleosomes reconstituted on distinguishable DNA species (two nucleosomes of each type) by ICeChIP-qPCR. H3K36me3 was chosen as it bears a trimethyllysine embedded in a different sequence context and modest off-target affinity of this antibody for H3K36me3 has been previously observed on peptide arrays (Bock et al., 2011). By inspection of our internal standards, we observed a barely detectable enrichment of H3K36me3 (2.8±0.4) beyond the unmodified nucleosome background (1.9±0.2). As compared to the robust on target signal (81±10), there is a 30-fold apparent specificity in this experiment. Thus, off-target binding of the antibody to H3K36me3-bearing nucleosomes is a negligible contributor to apparent H3K4me3 density.

In order to establish a more comprehensive set of internal standards, we constructed a number of modified histones encompassing many of the most well-studied di- and tri-methyllysines in histone H3 (Chen et al., 2014) and engineered a much larger set of barcoded DNA templates. Specifically, we designed a second generation of potential DNA templates (n=100) that had the additional feature of being putatively MNase resistant relative to our first generation. We tested all of these templates when reconstituted into H3K4me3-bearing nucleosomes in two parallel ICeChIP experiments, spiking them in either before or after MNase digestion of mESC nuclei. The 72 unique barcoded templates that passed this stringent test (essentially combining all elements of our previous validation at once) were divided into nine sets, each with 8 members. We reconstituted six discrete ladders for unmodified, H3K4me3, H3K9me3, H3K27me3, H3K36me3 and H3K79me2 nucleosomes, and doped an equivalent of each ladder into a single pool of mESC nuclei. This combined mixture was subjected to micrococcal nuclease digestion, followed by hydroxyapatite purification as before, and then the pool of largely mononucleosomes was probed with the most well validated antibodies available for each of these marks.

Sequencing of each ICeChIP afforded a direct in situ assessment of antibody specificity by comparison of on- versus off-target internal standard capture (FIG. 9A). Gratifyingly, the H3K4me3 antibody proved to be highly specific when challenged with these other nucleosomal internal standards (H3K9me3 is equivalent to 3% of the on-target capture). H3K9me3 and H3K27me3 antibodies were slightly less specific, with mutual cross-recognition (representing 10% and 26% of the on-target signal, respectively) as might be expected as both marks reside within in an "ARKS" motif. Surprisingly, the most widely used antibodies for H3K36me3 and H3K79me2 were quite promiscuous in this experiment (around 2-3 fold specific at best, despite passing several independent ENCODE validations). The modest selectivity apparent is especially problematic for these two marks, as they are far less abundant than most of the off-target nucleosomal marks that their antibodies also recognize. In particular, mass spectrometry measurements from the same cell line report H3K36me3 and H3K79me2 to account for 2.5% and 0.5% of all H3, whereas H3K9me3 and H3K27me3 are an order of magnitude more abundant (Voigt et al., 2012). Thus, the modest fold-specificities are more than offset by the fold-abundance differences in the opposite direction.

The off-target capture is linear with respect to the amount of nucleosomal epitope for five different antibodies (FIG. 9B-D). While antibody specificity may vary, the background for a given antibody is deterministic and proportional to the amount of the off-target species present in the input. Thus our approach of applying the internal standard as a scalar is valid when the internal standard is linear and the background binding is modest and measurable. Specific HMD signal for a given mark can be corrected by solving a set of linear equations. Despite higher apparent HMD values for H3K36me3 and H3K79me2 at loci previously reported to be enriched in these marks, HMD as well as native ChIP measurements with these antibodies represent more noise than signal in our experiments (FIG. 9A. Conversely, HMD values for H3K4me3, H3K9me3 and H3K27me3 display minimal inflation and correctable off-target binding, so that we can quantitatively compare the amounts of these three marks genome wide.

With accurate measurements of actual histone amounts from H3K4me3, H3K9me3 and H3K27me3 ICeChIP-seq from diploid cells, we make statistical arguments about nucleosomal co-occupancy of marks when the sum of HMDs from two marks exceeds 100%. This interpretation applies to two different marks as well as one versus two copies of a given mark within a nucleosome, termed asymmetrically and symmetrically modified nucleosomes, respectively (Voigt et al., 2012). Plotting heat maps for H3K4me3 and H3K27me3 modification density arranged in rank order from highest to lowest TSS-localized H3K4me3 HMD for all genes in mESCs reveals several broad classes of genes with different patterns of these two modifications. Surprisingly, the levels of H3K27me3 are only modestly reduced at genes that are highly expressed, as exemplified by metabolic/housekeeping genes, whereas the highest HMDs for this mark are present at a subset of early developmental genes. Indeed, other repressed late development genes from classes that are silent in mESCs, such as neurological and immune system processes (58 and 62% H3K27me3), are significantly less enriched in H3K27me3 ($p<10$ 56, 10 19, respectively) than repressed cell differentiation genes (70% H3K27me3). Developmental genes in *Drosophila* S2 cells also bear the highest H3K27me3 average HMD.

The H3K4me3 mark promotes transcriptional initiation via several known mechanisms (Guenther et al., 2007; Lauberth et al., 2013; Ruthenburg et al., 2007a; Santos-Rosa et al., 2002; Schubeler, 2004). A priori, HMD might be construed to be uninformative for examining correlations to gene expression, because relative ChIP-seq peak height is equivalent to HMD when correlated to gene expression. Yet, when H3K4me3 is examined on a biologically meaningful scale, binned mRNA abundance reveals an intriguing sigmoidal dependence on average apparent HMD at the corresponding TSSs. Assuming accurate measurement of H3K4me3 density, the inflection point of this curve (~50% HMD) lies approximately at the statistical boundary between, on average, asymmetrically-versus symmetrically-modified nucleosomes over both alleles. Could the lower HMD population simply represent a broader spatial distribution of the H3K4me3 beyond the TSS as has recently been suggested to reduce transcriptional variation (Benayoun et al., 2014)? Close examination reveals quite the opposite— mean peak HMD values positively correlate with peak span in mouse and human cells; again this distribution is bimodal and that larger modification domains have higher average HMD values consistent with symmetric modification.

Example 4: ICe-ChIP as a Diagnostic Tool

The ICe-ChIP materials and methods described herein are envisioned for use in assays aimed at detecting levels of histone PTMs at particular genetic loci within mammalian samples. The present materials and methods can be used in the diagnosis, prognosis, classification, prediction of disease risk, detection of recurrence, selection of treatment, and evaluation of treatment efficacy for any disease associated with changes in histone post-translational modifications, including cancer.

For example, H3K79me2 driven expression of two crucial genes, HOXA9 and MEIS1 is a common checkpoint driving a large percentage of acute myelogenous leukemias that arise from diverse genetic mutations (Bernt et al., 2011; Kroon et al., 1998). The present invention can be used to measure the H3K79me2 HMD at these loci from a patient blood sample to determine whether a patient's cells have passed this checkpoint and whether acute myelogenous leukemias can be diagnosed. The H3K79me2 HMD at these loci in the patient blood sample are compared to the H3K79me2 HMD at these loci from a normal sample and an increase in HMD in the patient sample relative to the control indicates a high risk of acute myelogenous leukemia.

In another embodiment, anti-cancer treatment can be assessed by monitoring histone post-translational modifications described herein over time in a mammal having receiving treatment for a disease. For example, prior to administration of an H3K79me2-methyltransferase inhibitor, such as DOT1L inhibitor (Diagle et al., 2011), to treat acute myelogenous leukemia, the post-translational modification status of H3K79me2 at the HOXA9 and MEIS1 loci can be determined using ICe-ChIP. Effectiveness of the inhibitor is then determined by comparing the H3K79me2 HMD to the pre-treatment sample, a control sample, or a pre-established threshold as described above. Because ICe-ChIP standardizes the analysis across multiple samples, comparison between pre- and post-treatment or healthy and unhealthy samples yield biologically relevant information and is thus useful for diagnostics that assess efficacy of a therapeutic in patients, including during the course of pharmaceutical development.

Further, the present methods and materials may be used to detect whether a particular drug has had no effect on histone, thereby indicating the specificity of a drug for modifying histone post-translation modifications of interest.

TABLE 1 (a)

Post translational modifications for Human Histones H2A type 1/2/3, H2A.X, H2A.Z and H2A.V Isoform 1/2/3/4/5

Post translational modifications of: Human Histone H2A type 1/2/3

| Position | Description of Modification Type |
|---|---|
| 1 | N-acetylserine |
| 1 | Phosphoserine |
| 3 | Citrulline |
| 5 | N6-acetyllysine |
| 36 | N6-crotonyl-L-lysine |
| 118 | N6-crotonyl-L-lysine |
| 119 | N6-crotonyl-L-lysine; |
| 120 | Phosphothreonine |
| 126 | N6-crotonyl-L-lysine |
| 13 | Glycyl lysine isopeptide (Lys-Gly) (interchain with G-Cter in ubiquitin) |
| 15 | Glycyl lysine isopeptide (Lys-Gly) (interchain with G-Cter in ubiquitin) |
| 119 | Glycyl lysine isopeptide (Lys-Gly) (interchain with G-Cter in ubiquitin) |

Post translational modifications of: Human Histone H2A.X

| Position | Description of Modification Type |
|---|---|
| 1 | N-acetylserine |
| 1 | Phosphoserine |
| 36 | N6-acetyllysine |
| 119 | Phosphoserine |
| 142 | Phosphotyrosine |
| 13 | Glycyl lysine isopeptide (Lys-Gly) (interchain with G-Cter in ubiquitin) |
| 15 | Glycyl lysine isopeptide (Lys-Gly) (interchain with G-Cter in ubiquitin) |
| 119 | Glycyl lysine isopeptide (Lys-Gly) (interchain with G-Cter in ubiquitin) |

Post translational modifications of: Human Histone H2A.Z

| Position | Description of Modification Type |
|---|---|
| 1 | N-acetylalanine |
| 4 | N6-acetyllysine |
| 7 | N6-acetyllysine |
| 11 | N6-acetyllysine |
| 13 | N6-acetyllysine |
| 121 | Glycyl lysine isopeptide (Lys-Gly) (interchain with G-Cter in ubiquitin) |

Post translational modifications of: Human Histone H2A.V Isoform 1/2/3/4/5

| Position | Description of Modification Type |
|---|---|
| 4 | N6-acetyllysine |
| 7 | N6-acetyllysine |
| 11 | N6-acetyllysine |
| 121 | Glycyl lysine isopeptide (Lys-Gly) (interchain with G-Cter in ubiquitin) |

TABLE 1 (b)

Post translational modifications for Human Histone H2A.J and H2B type 1

Post translational modifications of: Human Histone H2A.J

| Position | Description of Modification Type |
|---|---|
| 1 | N-acetylserine |
| 1 | Phosphoserine |
| 5 | N6-acetyllysine |
| 120 | Phosphothreonine |
| 122 | Phosphoserine |

TABLE 1 (b)-continued

Post translational modifications for Human Histone H2A.J and H2B type 1

Post translational modifications of: Human Histone H2A.J

| | |
|---|---|
| 13 | Glycyl lysine isopeptide (Lys-Gly) (interchain with G-Cter in ubiquitin) |
| 15 | Glycyl lysine isopeptide (Lys-Gly) (interchain with G-Cter in ubiquitin) |
| 119 | Glycyl lysine isopeptide (Lys-Gly) (interchain with G-Cter in ubiquitin) |

Post translational modifications of: Human Histone H2B type 1

| | |
|---|---|
| 1 | N-acetylproline |
| 6 | N6-acetyllysine |
| 6 | N6-crotonyl-L-lysine |
| 12 | N6-acetyllysine |
| 12 | N6-crotonyl-L-lysine |
| 13 | N6-acetyllysine |
| 13 | N6-crotonyl-L-lysine |
| 16 | N6-acetyllysine |
| 16 | N6-crotonyl-L-lysine |
| 17 | N6-acetyllysine |
| 17 | N6-crotonyl-L-lysine |
| 21 | N6-acetyllysine |
| 21 | N6-crotonyl-L-lysine |
| 24 | N6-acetyllysine |
| 24 | N6-crotonyl-L-lysine |
| 35 | N6-crotonyl-L-lysine |
| 37 | Phosphoserine |
| 47 | N6-methyllysine |
| 58 | N6, N6-dimethyllysine |
| 80 | Dimethylated arginine |
| 85 | Phosphoserine |
| 86 | N6, N6, N6-trimethyllysine |
| 86 | N6-acetyllysine |
| 87 | Omega-N-methylarginine |
| 93 | Omega-N-methylarginine |
| 109 | N6-methyllysine |
| 116 | Phosphothreonine |
| 117 | N6-methylated lysine |
| 35 | Glycyl lysine isopeptide (Lys-Gly) (interchain with G-Cter in ubiquitin) |
| 121 | Glycyl lysine isopeptide (Lys-Gly) (interchain with G-Cter in ubiquitin) |

TABLE 1 (c)

Post translational modifications for Human Histone H2B type 2/3/F-S

Post translational modifications of: Human Histone H2B type 2/3/F-S

| Position | Description of Modification Type |
|---|---|
| 1 | N-acetylproline |
| 5 | N6-acetyllysine |
| 5 | N6-crotonyl-L-lysine |
| 11 | N6-acetyllysine |
| 11 | N6-crotonyl-L-lysine |
| 12 | N6-acetyllysine |
| 12 | N6-crotonyl-L-lysine |
| 14 | Phosphoserine |
| 15 | N6-acetyllysine |
| 15 | N6-crotonyl-L-lysine |
| 16 | N6-acetyllysine |
| 16 | N6-crotonyl-L-lysine |
| 20 | N6-acetyllysine |
| 20 | N6-crotonyl-L-lysine |
| 23 | N6-acetyllysine |
| 23 | N6-crotonyl-L-lysine |
| 34 | N6-crotonyl-L-lysine |
| 36 | Phosphoserine |
| 46 | N6-methyllysine |
| 57 | N6, N6-dimethyllysine |
| 79 | Dimethylated arginine |
| 85 | N6, N6, N6-trimethyllysine |
| 85 | N6-acetyllysine |
| 86 | Omega-N-methylarginine |
| 92 | Omega-N-methylarginine |
| 108 | N6-methyllysine |
| 115 | Phosphothreonine |
| 116 | N6-methylated lysine |

TABLE 1 (c)-continued

Post translational modifications for Human Histone H2B type 2/3/F-S

Post translational modifications of: Human Histone H2B type 2/3/F-S

| | |
|---|---|
| 112 | O-linked (GlcNAc) |
| 34 | Glycyl lysine isopeptide (Lys-Gly) (interchain with G-Cter in ubiquitin) |
| 121 | Glycyl lysine isopeptide (Lys-Gly) (interchain with G-Cter in ubiquitin) |

TABLE 1 (d)

Post translational modifications for Human Putative Histone H2B type 2-D/2-C
Post translational modifications of: Human Putative Histone H2B type 2-D/2-C

| Position | Description of Modification Type |
|---|---|
| 1 | N-acetylproline |
| 5 | N6-acetyllysine |
| 5 | N6-crotonyl-L-lysine |
| 11 | N6-acetyllysine |
| 11 | N6-crotonyl-L-lysine |
| 12 | N6-acetyllysine |
| 12 | N6-crotonyl-L-lysine |
| 14 | Phosphoserine |
| 15 | N6-acetyllysine |
| 15 | N6-crotonyl-L-lysine |
| 16 | N6-acetyllysine |
| 16 | N6-crotonyl-L-lysine |
| 20 | N6-acetyllysine |
| 20 | N6-crotonyl-L-lysine |
| 23 | N6-acetyllysine |
| 23 | N6-crotonyl-L-lysine |
| 34 | N6-crotonyl-L-lysine |
| 36 | Phosphoserine |
| 46 | N6-methyllysine |
| 57 | N6, N6-dimethyllysine |
| 79 | Dimethylated arginine |
| 85 | N6, N6, N6-trimethyllysine |
| 85 | N6-acetyllysine |
| 86 | Omega-N-methylarginine |
| 92 | Omega-N-methylarginine |

TABLE 1(e)

Post translational modifications for Human Histone H3.1/H3.1t/H3.2/H3.3/H3.3C
Post translational modifications of: Human Histone H3.1/H3.1t/H3.2/H3.3/H3.3C

| Position | Modification Type |
|---|---|
| 2 | Asymmetric dimethylarginine |
| 3 | Phosphothreonine |
| 4 | Allysine |
| 4 | N6, N6, N6-trimethyllysine |
| 4 | N6, N6-dimethyllysine |
| 4 | N6-acetyllysine |
| 4 | N6-crotonyl-L-lysine |
| 4 | N6-methyllysine |
| 6 | Phosphothreonine |
| 8 | Citrulline |
| 8 | Symmetric dimethylarginine |
| 9 | N6, N6, N6-trimethyllysine |
| 9 | N6, N6-dimethyllysine |
| 9 | N6-acetyllysine |
| 9 | N6-crotonyl-L-lysine |
| 9 | N6-methyllysine |
| 10 | Phosphoserine |
| 11 | Phosphothreonine |
| 14 | N6-acetyllysine |
| 17 | Asymmetric dimethylarginine |
| 17 | Citrulline |
| 18 | N6-acetyllysine |
| 18 | N6-crotonyl-L-lysine |
| 18 | N6-methyllysine |
| 23 | N6-acetyllysine |
| 23 | N6-crotonyl-L-lysine |
| 23 | N6-methyllysine |
| 27 | N6, N6, N6-trimethyllysine |
| 27 | N6, N6-dimethyllysine |
| 27 | N6-acetyllysine |
| 27 | N6-crotonyl-L-lysine |
| 27 | N6-methyllysine |
| 28 | Phosphoserine |
| 36 | N6, N6, N6-trimethyllysine |
| 36 | N6, N6-dimethyllysine |
| 36 | N6-acetyllysine |
| 36 | N6-methyllysine |
| 37 | N6-methyllysine |
| 41 | Phosphotyrosine |
| 56 | N6, N6, N6-trimethyllysine |
| 56 | N6-acetyllysine |
| 56 | N6-crotonyl-L-lysine |
| 56 | N6-methyllysine |
| 57 | Phosphoserine |
| 64 | N6-methyllysine |
| 79 | N6, N6, N6-trimethyllysine |
| 79 | N6, N6-dimethyllysine |
| 79 | N6-acetyllysine |
| 79 | N6-methyllysine |
| 80 | Phosphothreonine |
| 107 | Phosphothreonine |
| 115 | N6-acetyllysine |
| 122 | N6-acetyllysine |
| 122 | N6-methyllysine |

TABLE 1 (f)

Post translational modifications for Human Histone H3-like centromeric protein A and Human Histone H4

Post translational modifications of: Human Histone H3-like centromeric protein A

| Position | Description of Modification Type |
|---|---|
| 6 | Phosphoserine; by AURKA and AURKB |
| 16 | Phosphoserine |

TABLE 1 (f)-continued

Post translational modifications for Human Histone H3-like centromeric protein A and Human Histone H4

Post translational modifications of: Human Histone H3-like centromeric protein A

| | |
|---|---|
| 18 | Phosphoserine |
| 26 | Phosphoserine |

Post translational modifications of: Human Histone H4

| | |
|---|---|
| 1 | N-acetylserine |
| 1 | Phosphoserine |
| 3 | Asymmetric dimethylarginine |
| 3 | Citrulline |
| 3 | Omega-N-methylarginine |
| 3 | Symmetric dimethylarginine |
| 5 | N6-acetyllysine |
| 5 | N6-crotonyl-L-lysine |
| 8 | N6-acetyllysine |
| 8 | N6-crotonyl-L-lysine |
| 12 | N6-acetyllysine |
| 12 | N6-crotonyl-L-lysine |
| 16 | N6-acetyllysine |
| 16 | N6-crotonyl-L-lysine |
| 20 | N6, N6, N6-trimethyllysine |
| 20 | N6, N6-dimethyllysine |
| 20 | N6-methyllysine |
| 31 | N6-acetyllysine |
| 47 | Phosphoserine |
| 51 | Phosphotyrosine |
| 88 | Phosphotyrosine |
| 91 | N6-acetyllysine |
| 91 | Glycyl lysine isopeptide (Lys-Gly) (interchain with G-Cter in ubiquitin) |

TABLE 2

| SEQ ID NO | Name | extended name | Sequence | Length [bp] | Performance in ICeChIP |
|---|---|---|---|---|---|
| 1 | 601-A1 | 601-0102 | GGCGGCcgacgcgatacaccgttcgtcgctggagaatcccggtgccgaggcc gctcaattggtcgtagacagctctagcaccgcttaaacgcacgtacgcgctgtcc ccgcgttttaaccgccaaggggattactccctagtctccaggcacgtgtcagat atatacatcctgtgcgttcgacggtacgtcgagcgGCCGCC | 203 | Poor |
| 2 | 601-A2 | 601-0304 | GGCGGCgtatcgcgtcgcgcgtaatcgactggagaatcccggtgccgaggcc gctcaattggtcgtagacagctctagcaccgcttaaacgcacgtacgcgctgtcc ccgcgttttaaccgccaaggggattactccctagtctccaggcacgtgtcagat atatacatcctgtgcgcgacgttacgctcgacgtaGCCGCC | 203 | Poor |
| 3 | 601-A3 | 601-0506 | GGCGGCaccgatacgcgcgcggtacgatctggagaatcccggtgccgaggcc gctcaattggtcgtagacagctctagcaccgcttaaacgcacgtacgcgctgtcc ccgcgttttaaccgccaaggggattactccctagtctccaggcacgtgtcagat atatacatcctgttaatcgacgcgatatcgcgcgtGCCGCC | 203 | Poor |
| 4 | 601-A4 | 601-0708 | GGCGGCatatcgcgcgtcgtatcgcggtctggagaatcccggtgccgaggcg ctcaattggtcgtagacagctctagcaccgcttaaacgcacgtacgcgctgtccc cgcgttttaaccgccaaggggattactccctagtctccaggcacgtgtcagata tatacatcctgttcgtatcgcgccgcgtattcggGCCGCC | 203 | Good |
| 5 | 601-A5 | 601-0910 | GGCGGCccgcgcgatattacgcgcgaatctggagaatcccggtgccgaggcc gctcaattggtcgtagacagctctagcaccgcttaaacgcacgtacgcgctgtcc ccgcgttttaaccgccaaggggattactccctagtctccaggcacgtgtcagat atatacatcctgtacgaacgtcgatcgtcgattcgGCCGCC | 203 | Poor |
| 6 | 601-A6 | 601-1112 | GGCGGCcgacgaacggttcgtacgcgagctggagaatcccggtgccgaggcc gctcaattggtcgtagacagctctagcaccgcttaaacgcacgtacgcgctgtcc ccgcgttttaaccgccaaggggattactccctagtctccaggcacgtgtcagat atatacatcctgttcgcgtacgaatcgcgtaatcgGCCGCC | 203 | Poor |
| 7 | 601-A7 | 601-1314 | GGCGGCcgcgtaatacgccgcgatacgactggagaatcccggtgccgaggcc gctcaattggtcgtagacagctctagcaccgcttaaacgcacgtacgcgctgtcc ccgcgttttaaccgccaaggggattactccctagtctccaggcacgtgtcagat atatacatcctgtaacgcgtatcgcgcgtaacgcgGCCGCC | 203 | Poor |

TABLE 2-continued

| SEQ ID NO | Name | extended name | Sequence | Length [bp] | Performance in ICeChIP |
|---|---|---|---|---|---|
| 8 | 601-A8 | 601-1516 | GGCGGCcgtacgacgctcgcgatatccgctggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtcgacgttaacgcgttacgcgtcGCCGCC | 203 | Poor |
| 9 | 601-A9 | 601-1718 | GGCGGCgcgttcgacgggtcgcgaactactggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtgtcgcgaactacgtcgttcgacGCCGCC | 203 | Poor |
| 10 | 601-A10 | 601-1920 | GGCGGCtacgctcggactcgcgcgatgactggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtcgatcgtcgcatcggtacgctaGCCGCC | 203 | Poor |
| 11 | 601-A11 | 601-2122 | GGCGGCtattatgcgcgacccgcgtacgctggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtcgtaccgcgatccgacgatcgaGCCGCC | 203 | Good |
| 12 | 601-A12 | 601-2324 | GGCGGCtcgcgaccgtacgaatttcgcgctggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtcgcgtcaatcgcgattacgcgaGCCGCC | 203 | Poor |
| 13 | 601-A13 | 601-2526 | GGCGGCtcgtacgaccgcgcgtatcgggctggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtgcgatcgtacgcgcgacgttaaGCCGCC | 203 | Poor |
| 14 | 601-A14 | 601-0916 | GGCGGCccgcgcgatattacgcgcgaatctggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtcgacgttaacgcgttacgcgtcGCCGCC | 203 | Good |
| 15 | 601-A15 | 601-1510 | GGCGGCcgtacgacgctcgcgatatccgctggagaatcccggtgccgaggcc gctcaattggtcgtagacagctctagcaccgcttaaacgcacgtacgcgctgtcc cccgcgttttaaccgccaaggggattactccctagtctccaggcacgtgtcagat atatacatcctgtacgaacgtcgatcgtcgattcgGCCGCC | 203 | Poor |
| 16 | C001 | 601_C001_Rev | ctggagaatcccggtgccgaggccgctcaattggtcgtagacagctctagcacc gcttaaacgcacgtacgcgctgtccccgcgttttaaccgccaaggggattactc cctagtctccaggctattatgcgcgcgatacgcgttTC | 147 | Good |
| 17 | C002 | 601_C002_Rev | ctggagaatcccggtgccgaggccgctcaattggtcgtagacagctctagcacc gcttaaacgcacgtacgcgctgtccccgcgttttaaccgccaaggggattactc cctagtctccaggccgcgcataataatcgcgcgattTC | 147 | Good |
| 18 | C003 | 601_C003_Rev | ctggagaatcccggtgccgaggccgctcaattggtcgtagacagctctagcacc gcttaaacgcacgtacgcgctgtccccgcgttttaaccgccaaggggattactc cctagtctccaggcatatcgcgcgttcgacgttcgtTC | 147 | Good |
| 19 | C004 | 601_C004_Rev | ctggagaatcccggtgccgaggccgctcaattggtcgtagacagctctagcacc gcttaaacgcacgtacgcgctgtccccgcgttttaaccgccaaggggattactc cctagtctccaggcacgcgcgatattatcgcgtcgtTC | 147 | Good |
| 20 | C005 | 601_C005_Rev | ctggagaatcccggtgccgaggccgctcaattggtcgtagacagctctagcacc gcttaaacgcacgtacgcgctgtccccgcgttttaaccgccaaggggattactc cctagtctccaggctcgtcgacgatcgtcgaatcgtTC | 147 | Good |
| 21 | C006 | 601_C006_Rev | ctggagaatcccggtgccgaggccgctcaattggtcgtagacagctctagcacc gcttaaacgcacgtacgcgctgtccccgcgttttaaccgccaaggggattactc cctagtctccaggctcgtcgattcgacgcgaatcgtTC | 147 | Good |
| 22 | C007 | 601_C007_Rev | ctggagaatcccggtgccgaggccgctcaattggtcgtagacagctctagcacc gcttaaacgcacgtacgcgctgtccccgcgttttaaccgccaaggggattactc cctagtctccaggctacgcgattcgtcgtttcgcgtTC | 147 | Good |
| 23 | C008 | 601_C008_Rev | ctggagaatcccggtgccgaggccgctcaattggtcgtagacagctctagcacc gcttaaacgcacgtacgcgctgtccccgcgttttaaccgccaaggggattactc cctagtctccaggctatacgcgtcgacgattcgcgtTC | 147 | Good |
| 24 | C009 | 601_C009_Rev | ctggagaatcccggtgccgaggccgctcaattggtcgtagacagctctagcacc gcttaaacgcacgtacgcgctgtccccgcgttttaaccgccaaggggattactc cctagtctccaggctcgcgtaatcgtttcgacgcgtTC | 147 | Good |

TABLE 2-continued

| SEQ ID NO | Name | extended name | Sequence | Length [bp] | Performance in ICeChIP |
|---|---|---|---|---|---|
| 25 | C010 | 601_C010_Rev | ctggagaatcccggtgccgaggccgctcaattggtcgtagacagctctagcacc gcttaaacgcacgtacgcgctgtccccgcgttttaaccgccaaggggattactc cctagtctccaggcttaacgtcgcgcgttcgaacgtTC | 147 | Good |
| 26 | C011 | 601_C011_Rev | ctggagaatcccggtgccgaggccgctcaattggtcgtagacagctctagcacc gcttaaacgcacgtacgcgctgtccccgcgttttaaccgccaaggggattactc cctagtctccaggccgtattacgcgaatcgcgcgatTC | 147 | Good |
| 27 | C012 | 601_C012_Rev | ctggagaatcccggtgccgaggccgctcaattggtcgtagacagctctagcacc gcttaaacgcacgtacgcgctgtccccgcgttttaaccgccaaggggattactc cctagtctccaggctcgattacgcgtcgcgcgtaatTC | 147 | Good |
| 28 | C013 | 601_C013_Rev | ctggagaatcccggtgccgaggccgctcaattggtcgtagacagctctagcacc gcttaaacgcacgtacgcgctgtccccgcgttttaaccgccaaggggattactc cctagtctccaggccgtttcgtacgcgcgacgtaatTC | 147 | Good |
| 29 | C014 | 601_C014_Rev | ctggagaatcccggtgccgaggccgctcaattggtcgtagacagctctagcacc gcttaaacgcacgtacgcgctgtccccgcgttttaaccgccaaggggattactc cctagtctccaggctcgcgtatacgtacgcgcgaatTC | 147 | Good |
| 30 | C015 | 601_C015_Rev | ctggagaatcccggtgccgaggccgctcaattggtcgtagacagctctagcacc gcttaaacgcacgtacgcgctgtccccgcgttttaaccgccaaggggattactc cctagtctccaggccgcgtaatacgcgcgaaattcgTC | 147 | Good |
| 31 | C016 | 601_C016_Rev | ctggagaatcccggtgccgaggccgctcaattggtcgtagacagctctagcacc gcttaaacgcacgtacgcgctgtccccgcgttttaaccgccaaggggattactc cctagtctccaggcgatagtcgacgttatcgcgtcgTC | 147 | Good |
| 32 | C017 | 601_C017_Rev | ctggagaatcccggtgccgaggccgctcaattggtcgtagacagctctagcacc gcttaaacgcacgtacgcgctgtccccgcgttttaaccgccaaggggattactc cctagtctccaggccgtacgaaacgcgttaacgtcgTC | 147 | Good |
| 33 | C018 | 601_C018_Rev | ctggagaatcccggtgccgaggccgctcaattggtcgtagacagctctagcacc gcttaaacgcacgtacgcgctgtccccgcgttttaaccgccaaggggattactc cctagtctccaggccgtcgactatctcgtcgtatcgTC | 147 | Good |
| 34 | C019 | 601_C019_Rev | ctggagaatcccggtgccgaggccgctcaattggtcgtagacagctctagcacc gcttaaacgcacgtacgcgctgtccccgcgttttaaccgccaaggggattactc cctagtctccaggcttacgcgtaccaacgcgtatcgTC | 147 | Good |
| 35 | C020 | 601_C020_Rev | ctggagaatcccggtgccgaggccgctcaattggtcgtagacagctctagcacc gcttaaacgcacgtacgcgctgtccccgcgttttaaccgccaaggggattactc cctagtctccaggccgaatcgcgtattacgcgatcgTC | 147 | Good |
| 36 | C021 | 601_C021_Rev | ctggagaatcccggtgccgaggccgctcaattggtcgtagacagctctagcacc gcttaaacgcacgtacgcgctgtccccgcgttttaaccgccaaggggattactc cctagtctccaggctcggtacgctatcgtacgatcgTC | 147 | Good |
| 37 | C022 | 601_C022_Rev | ctggagaatcccggtgccgaggccgctcaattggtcgtagacagctctagcacc gcttaaacgcacgtacgcgctgtccccgcgttttaaccgccaaggggattactc cctagtctccaggccgacgcgtatacgaatttcgcgTC | 147 | Good |
| 38 | C023 | 601_C023_Rev | ctggagaatcccggtgccgaggccgctcaattggtcgtagacagctctagcacc gcttaaacgcacgtacgcgctgtccccgcgttttaaccgccaaggggattactc cctagtctccaggctcgacgcgataattacgtcgcgTC | 147 | Good |
| 39 | C024 | 601_C024_Rev | ctggagaatcccggtgccgaggccgctcaattggtcgtagacagctctagcacc gcttaaacgcacgtacgcgctgtccccgcgttttaaccgccaaggggattactc cctagtctccaggctcgcgcgaatattcgtatcgcgTC | 147 | Good |
| 40 | C025 | 601_C025_Rev | ctggagaatcccggtgccgaggccgctcaattggtcgtagacagctctagcacc gcttaaacgcacgtacgcgctgtccccgcgttttaaccgccaaggggattactc cctagtctccaggctatcgcgtcgagtgatatcgcgTC | 147 | Good |
| 41 | C026 | 601_C026_Rev | ctggagaatcccggtgccgaggccgctcaattggtcgtagacagctctagcacc gcttaaacgcacgtacgcgctgtccccgcgttttaaccgccaaggggattactc cctagtctccaggccgcgtaatcgatacgttacgcgTC | 147 | Good |
| 42 | C027 | 601_C027_Rev | ctggagaatcccggtgccgaggccgctcaattggtcgtagacagctctagcacc gcttaaacgcacgtacgcgctgtccccgcgttttaaccgccaaggggattactc cctagtctccaggcttacgtcgcgataatcgacgcgTC | 147 | Good |
| 43 | C028 | 601_C028_Rev | ctggagaatcccggtgccgaggccgctcaattggtcgtagacagctctagcacc gcttaaacgcacgtacgcgctgtccccgcgttttaaccgccaaggggattactc cctagtctccaggctattcgcgcgatcgcgattacgTC | 147 | Good |

TABLE 2-continued

| SEQ ID NO | Name | extended name | Sequence | Length [bp] | Performance in ICeChIP |
|---|---|---|---|---|---|
| 44 | C029 | 601_C029_Rev | ctggagaatcccggtgccgaggccgctcaattggtcgtagacagctctagcacc gcttaaacgcacgtacgcgctgtccccgcgttttaaccgccaaggggattactc cctagtctccaggccgattacgcgaacgattcgacgTC | 147 | Good |
| 45 | C030 | 601_C030_Rev | ctggagaatcccggtgccgaggccgctcaattggtcgtagacagctctagcacc gcttaaacgcacgtacgcgctgtccccgcgttttaaccgccaaggggattactc cctagtctccaggccgtatacgcgattaacgcgacgTC | 147 | Good |
| 46 | C031 | 601_C031_Rev | ctggagaatcccggtgccgaggccgctcaattggtcgtagacagctctagcacc gcttaaacgcacgtacgcgctgtccccgcgttttaaccgccaaggggattactc cctagtctccaggctagcgtaccgacgacgttaacTC | 147 | Good |
| 47 | C032 | 601_C032_Rev | ctggagaatcccggtgccgaggccgctcaattggtcgtagacagctctagcacc gcttaaacgcacgtacgcgctgtccccgcgttttaaccgccaaggggattactc cctagtctccaggcatcgtcgacgaacgttcgaacTC | 147 | Good |
| 48 | C033 | 601_C033_Rev | ctggagaatcccggtgccgaggccgctcaattggtcgtagacagctctagcacc gcttaaacgcacgtacgcgctgtccccgcgttttaaccgccaaggggattactc cctagtctccaggccgaatcgacgatagttcgcgacTC | 147 | Good |
| 49 | C034 | 601_C034_Rev | ctggagaatcccggtgccgaggccgctcaattggtcgtagacagctctagcacc gcttaaacgcacgtacgcgctgtccccgcgttttaaccgccaaggggattactc cctagtctccaggccgcgacgttaacgcgatatcacTC | 147 | Good |
| 50 | C035 | 601_C035_Rev | ctggagaatcccggtgccgaggccgctcaattggtcgtagacagctctagcacc gcttaaacgcacgtacgcgctgtccccgcgttttaaccgccaaggggattactc cctagtctccaggcggtacgcgtaacgcgtcgattaTC | 147 | Good |
| 51 | C036 | 601_C036_Rev | ctggagaatcccggtgccgaggccgctcaattggtcgtagacagctctagcacc gcttaaacgcacgtacgcgctgtccccgcgttttaaccgccaaggggattactc cctagtctccaggctcgcgacgtaaaattcgcgcgtaTC | 147 | Good |
| 52 | C037 | 601_C037_Rev | ctggagaatcccggtgccgaggccgctcaattggtcgtagacagctctagcacc gcttaaacgcacgtacgcgctgtccccgcgttttaaccgccaaggggattactc cctagtctccaggccgcgtatcggtcgcgtaacgtaTC | 147 | Good |
| 53 | C038 | 601_C038_Rev | ctggagaatcccggtgccgaggccgctcaattggtcgtagacagctctagcacc gcttaaacgcacgtacgcgctgtccccgcgttttaaccgccaaggggattactc cctagtctccaggccgacgaacggtgtcgcgaactaTC | 147 | Good |
| 54 | C039 | 601_C039_Rev | ctggagaatcccggtgccgaggccgctcaattggtcgtagacagctctagcacc gcttaaacgcacgtacgcgctgtccccgcgttttaaccgccaaggggattactc cctagtctccaggccgaacggtcgtttcgcgcgataTC | 147 | Good |
| 55 | C040 | 601_C040_Rev | ctggagaatcccggtgccgaggccgctcaattggtcgtagacagctctagcacc gcttaaacgcacgtacgcgctgtccccgcgttttaaccgccaaggggattactc cctagtctccaggcccgacgatcgtacgacgcgataTC | 147 | Good |
| 56 | C041 | 601_C041_Rev | ctggagaatcccggtgccgaggccgctcaattggtcgtagacagctctagcacc gcttaaacgcacgtacgcgctgtccccgcgttttaaccgccaaggggattactc cctagtctccaggccgacgtaccgtttacgcgtcgaTC | 147 | Good |
| 57 | C042 | 601_C042_Rev | ctggagaatcccggtgccgaggccgctcaattggtcgtagacagctctagcacc gcttaaacgcacgtacgcgctgtccccgcgttttaaccgccaaggggattactc cctagtctccaggccgtacgacgctacgaacgtcgaTC | 147 | Good |
| 58 | C043 | 601_C043_Rev | ctggagaatcccggtgccgaggccgctcaattggtcgtagacagctctagcacc gcttaaacgcacgtacgcgctgtccccgcgttttaaccgccaaggggattactc cctagtctccaggcccgcgcgatatttttcgtcgcgaTC | 147 | Good |
| 59 | C044 | 601_C044_Rev | ctggagaatcccggtgccgaggccgctcaattggtcgtagacagctctagcacc gcttaaacgcacgtacgcgctgtccccgcgttttaaccgccaaggggattactc cctagtctccaggctcgcgcgacatcgtaatcgcgaTC | 147 | Good |
| 60 | C045 | 601_C045_Rev | ctggagaatcccggtgccgaggccgctcaattggtcgtagacagctctagcacc gcttaaacgcacgtacgcgctgtccccgcgttttaaccgccaaggggattactc cctagtctccaggccgcgcgatatgattacgcgcgaTC | 147 | Good |
| 61 | C046 | 601_C046_Rev | ctggagaatcccggtgccgaggccgctcaattggtcgtagacagctctagcacc gcttaaacgcacgtacgcgctgtccccgcgttttaaccgccaaggggattactc cctagtctccaggccgcgtattcggttcgtacgcgaTC | 147 | Good |
| 62 | C047 | 601_C047_Rev | ctggagaatcccggtgccgaggccgctcaattggtcgtagacagctctagcacc gcttaaacgcacgtacgcgctgtccccgcgttttaaccgccaaggggattactc cctagtctccaggctcgatcgtcggcgatcgtacgaTC | 147 | Good |

TABLE 2-continued

| SEQ ID NO | Name | extended name | Sequence | Length [bp] | Performance in ICeChIP |
|---|---|---|---|---|---|
| 63 | C048 | 601_C048_Rev | ctggagaatcccggtgccgaggccgctcaattggtcgtagacagctctagcacc gcttaaacgcacgtacgcgctgtccccgcgttttaaccgccaaggggattactc cctagtctccaggcacgatcgtcggtcgttcgacgaTC | 147 | Good |
| 64 | C049 | 601_C049_Rev | ctggagaatcccggtgccgaggccgctcaattggtcgtagacagctctagcacc gcttaaacgcacgtacgcgctgtccccgcgttttaaccgccaaggggattactc cctagtctccaggccgacgtatcggcgatacgacgaTC | 147 | Good |
| 65 | C050 | 601_C050_Rev | ctggagaatcccggtgccgaggccgctcaattggtcgtagacagctctagcacc gcttaaacgcacgtacgcgctgtccccgcgttttaaccgccaaggggattactc cctagtctccaggcatatcgcgcggtcgtcgaacgaTC | 147 | Good |
| 66 | C051 | 601_C051_Rev | ctggagaatcccggtgccgaggccgctcaattggtcgtagacagctctagcacc gcttaaacgcacgtacgcgctgtccccgcgttttaaccgccaaggggattactc cctagtctccaggccgacgtaacggacgcgaaacgaTC | 147 | Good |
| 67 | C052 | 601_C052_Rev | ctggagaatcccggtgccgaggccgctcaattggtcgtagacagctctagcacc gcttaaacgcacgtacgcgctgtccccgcgttttaaccgccaaggggattactc cctagtctccaggcacgaccgttcgcgtcgcgttaaTC | 147 | Good |
| 68 | C053 | 601_C053_Rev | ctggagaatcccggtgccgaggccgctcaattggtcgtagacagctctagcacc gcttaaacgcacgtacgcgctgtccccgcgttttaaccgccaaggggattactc cctagtctccaggccgtatcggtcgcgatcgcgtaaTC | 147 | Good |
| 69 | C054 | 601_C054_Rev | ctggagaatcccggtgccgaggccgctcaattggtcgtagacagctctagcacc gcttaaacgcacgtacgcgctgtccccgcgttttaaccgccaaggggattactc cctagtctccaggcctcgttcgtcgttcgcgcgtaaTC | 147 | Good |
| 70 | C055 | 601_C055_Rev | ctggagaatcccggtgccgaggccgctcaattggtcgtagacagctctagcacc gcttaaacgcacgtacgcgctgtccccgcgttttaaccgccaaggggattactc cctagtctccaggcaccgttcgtcgtcgacgcgtaaTC | 147 | Good |
| 71 | C056 | 601_C056_Rev | ctggagaatcccggtgccgaggccgctcaattggtcgtagacagctctagcacc gcttaaacgcacgtacgcgctgtccccgcgttttaaccgccaaggggattactc cctagtctccaggctacgtccgtcgcgacgcgataaTC | 147 | Good |
| 72 | C057 | 601_C057_Rev | ctggagaatcccggtgccgaggccgctcaattggtcgtagacagctctagcacc gcttaaacgcacgtacgcgctgtccccgcgttttaaccgccaaggggattactc cctagtctccaggcccgttacgtcgtatcgcgcgaaTC | 147 | Good |
| 73 | C058 | 601_C058_Rev | ctggagaatcccggtgccgaggccgctcaattggtcgtagacagctctagcacc gcttaaacgcacgtacgcgctgtccccgcgttttaaccgccaaggggattactc cctagtctccaggcacggtacgtcgttacgcgcgaaTC | 147 | Good |
| 74 | C059 | 601_C059_Rev | ctggagaatcccggtgccgaggccgctcaattggtcgtagacagctctagcacc gcttaaacgcacgtacgcgctgtccccgcgttttaaccgccaaggggattactc cctagtctccaggcccgatacgtcgtcgcgtacgaaTC | 147 | Good |
| 75 | C060 | 601_C060_Rev | ctggagaatcccggtgccgaggccgctcaattggtcgtagacagctctagcacc gcttaaacgcacgtacgcgctgtccccgcgttttaaccgccaaggggattactc cctagtctccaggctcgcacgatcgcgcgatacgaaTC | 147 | Good |
| 76 | C061 | 601_C061_Rev | ctggagaatcccggtgccgaggccgctcaattggtcgtagacagctctagcacc gcttaaacgcacgtacgcgctgtccccgcgttttaaccgccaaggggattactc cctagtctccaggctcgccgaatcgacgcgtcgaaaTC | 147 | Good |
| 77 | C062 | 601_C062_Rev | ctggagaatcccggtgccgaggccgctcaattggtcgtagacagctctagcacc gcttaaacgcacgtacgcgctgtccccgcgttttaaccgccaaggggattactc cctagtctccaggctatgcgtcgcgtcgcgacgaaaTC | 147 | Good |
| 78 | C063 | 601_C063_Rev | ctggagaatcccggtgccgaggccgctcaattggtcgtagacagctctagcacc gcttaaacgcacgtacgcgctgtccccgcgttttaaccgccaaggggattactc cctagtctccaggccatatcgcgcgcgtatcgcggtTC | 147 | Good |
| 79 | C064 | 601_C064_Rev | ctggagaatcccggtgccgaggccgctcaattggtcgtagacagctctagcacc gcttaaacgcacgtacgcgctgtccccgcgttttaaccgccaaggggattactc cctagtctccaggccgtatagcgcgccgtacgtcgtTC | 147 | Good |
| 80 | C065 | 601_C065_Rev | ctggagaatcccggtgccgaggccgctcaattggtcgtagacagctctagcacc gcttaaacgcacgtacgcgctgtccccgcgttttaaccgccaaggggattactc cctagtctccaggcaccgatacgcgtagcgacgcgtTC | 147 | Good |
| 81 | C066 | 601_C066_Rev | ctggagaatcccggtgccgaggccgctcaattggtcgtagacagctctagcacc gcttaaacgcacgtacgcgctgtccccgcgttttaaccgccaaggggattactc cctagtctccaggcccgaatacgcgtcgacgaccgtTC | 147 | Good |

TABLE 2-continued

| SEQ ID NO | Name | extended name | Sequence | Length [bp] | Performance in ICeChIP |
|---|---|---|---|---|---|
| 82 | C067 | 601_C067_Rev | ctggagaatcccggtgccgaggccgctcaattggtcgtagacagctctagcacc gcttaaacgcacgtacgcgctgtccccgcgttttaaccgccaaggggattactc cctagtctccaggctcgtacgaccgcggtcgaacgtTC | 147 | Good |
| 83 | C068 | 601_C068_Rev | ctggagaatcccggtgccgaggccgctcaattggtcgtagacagctctagcacc gcttaaacgcacgtacgcgctgtccccgcgttttaaccgccaaggggattactc cctagtctccaggcagcgtcgtacgtcgcgacgagtTC | 147 | Good |
| 84 | C069 | 601_C069_Rev | ctggagaatcccggtgccgaggccgctcaattggtcgtagacagctctagcacc gcttaaacgcacgtacgcgctgtccccgcgttttaaccgccaaggggattactc cctagtctccaggccgcgctatacgcgtaccgcgatTC | 147 | Good |
| 85 | C070 | 601_C070_Rev | ctggagaatcccggtgccgaggccgctcaattggtcgtagacagctctagcacc gcttaaacgcacgtacgcgctgtccccgcgttttaaccgccaaggggattactc cctagtctccaggccgaccgatacgcgcggtacgatTC | 147 | Good |
| 86 | C071 | 601_C071_Rev | ctggagaatcccggtgccgaggccgctcaattggtcgtagacagctctagcacc gcttaaacgcacgtacgcgctgtccccgcgttttaaccgccaaggggattactc cctagtctccaggcttcgagcgacgcggcgtacgatTC | 147 | Good |
| 87 | C072 | 601_C072_Rev | ctggagaatcccggtgccgaggccgctcaattggtcgtagacagctctagcacc gcttaaacgcacgtacgcgctgtccccgcgttttaaccgccaaggggattactc cctagtctccaggcgtcgaacgacgcggtcgacgatTC | 147 | Good |
| 88 | C073 | 601_C073_Rev | ctggagaatcccggtgccgaggccgctcaattggtcgtagacagctctagcacc gcttaaacgcacgtacgcgctgtccccgcgttttaaccgccaaggggattactc cctagtctccaggcgacgcgtaacgccgcgcgtaatTC | 147 | Good |
| 89 | C074 | 601_C074_Rev | ctggagaatcccggtgccgaggccgctcaattggtcgtagacagctctagcacc gcttaaacgcacgtacgcgctgtccccgcgttttaaccgccaaggggattactc cctagtctccaggctcgacgcgtagcgcgacgcaatTC | 147 | Good |
| 90 | C075 | 601_C075_Rev | ctggagaatcccggtgccgaggccgctcaattggtcgtagacagctctagcacc gcttaaacgcacgtacgcgctgtccccgcgttttaaccgccaaggggattactc cctagtctccaggccgacgaacgagtcgtatcgcggTC | 147 | Good |
| 91 | C076 | 601_C076_Rev | ctggagaatcccggtgccgaggccgctcaattggtcgtagacagctctagcacc gcttaaacgcacgtacgcgctgtccccgcgttttaaccgccaaggggattactc cctagtctccaggccgttacgcgtcttatcgcgcggTC | 147 | Good |
| 92 | C077 | 601_C077_Rev | ctggagaatcccggtgccgaggccgctcaattggtcgtagacagctctagcacc gcttaaacgcacgtacgcgctgtccccgcgttttaaccgccaaggggattactc cctagtctccaggctaacgtcgcgcattacgcgcggTC | 147 | Good |
| 93 | C078 | 601_C078_Rev | ctggagaatcccggtgccgaggccgctcaattggtcgtagacagctctagcacc gcttaaacgcacgtacgcgctgtccccgcgttttaaccgccaaggggattactc cctagtctccaggctacgtcggactatacgcgcggTC | 147 | Good |
| 94 | C079 | 601_C079_Rev | ctggagaatcccggtgccgaggccgctcaattggtcgtagacagctctagcacc gcttaaacgcacgtacgcgctgtccccgcgttttaaccgccaaggggattactc cctagtctccaggccgtcgttcgacacgacgtacggTC | 147 | Good |
| 95 | C080 | 601_C080_Rev | ctggagaatcccggtgccgaggccgctcaattggtcgtagacagctctagcacc gcttaaacgcacgtacgcgctgtccccgcgttttaaccgccaaggggattactc cctagtctccaggcgcgcgacgttacgattcgacggTC | 147 | Good |
| 96 | C081 | 601_C081_Rev | ctggagaatcccggtgccgaggccgctcaattggtcgtagacagctctagcacc gcttaaacgcacgtacgcgctgtccccgcgttttaaccgccaaggggattactc cctagtctccaggctgtcgcgcgtatacgctcgtcgTC | 147 | Good |
| 97 | C082 | 601_C082_Rev | ctggagaatcccggtgccgaggccgctcaattggtcgtagacagctctagcacc gcttaaacgcacgtacgcgctgtccccgcgttttaaccgccaaggggattactc cctagtctccaggcgtccgagcgtagtatcgcgtcgTC | 147 | Good |
| 98 | C083 | 601_C083_Rev | ctggagaatcccggtgccgaggccgctcaattggtcgtagacagctctagcacc gcttaaacgcacgtacgcgctgtccccgcgttttaaccgccaaggggattactc cctagtctccaggctcgcgaccgtagttacgcgtcgTC | 147 | Good |
| 99 | C084 | 601_C084_Rev | ctggagaatcccggtgccgaggccgctcaattggtcgtagacagctctagcacc gcttaaacgcacgtacgcgctgtccccgcgttttaaccgccaaggggattactc cctagtctccaggccgacggacgtacgtatccgtcgTC | 147 | Good |
| 100 | C085 | 601_C085_Rev | ctggagaatcccggtgccgaggccgctcaattggtcgtagacagctctagcacc gcttaaacgcacgtacgcgctgtccccgcgttttaaccgccaaggggattactc cctagtctccaggccgcgacgcatagcgttacgtcgTC | 147 | Good |

TABLE 2-continued

| SEQ ID NO | Name | extended name | Sequence | Length [bp] | Performance in ICeChIP |
|---|---|---|---|---|---|
| 101 | C086 | 601_C086_Rev | ctggagaatcccggtgccgaggccgctcaattggtcgtagacagctctagcacc gcttaaacgcacgtacgcgctgtccccgcgttttaaccgccaagggattactc cctagtctccaggcctacgcgtcgacgcgttagtcgTC | 147 | Good |
| 102 | C087 | 601_C087_Rev | ctggagaatcccggtgccgaggccgctcaattggtcgtagacagctctagcacc gcttaaacgcacgtacgcgctgtccccgcgttttaaccgccaagggattactc cctagtctccaggcccgacgatcgatcggcgtatcgTC | 147 | Good |
| 103 | C088 | 601_C088_Rev | ctggagaatcccggtgccgaggccgctcaattggtcgtagacagctctagcacc gcttaaacgcacgtacgcgctgtccccgcgttttaaccgccaagggattactc cctagtctccaggccgatcgtgcgacgcgactatcgTC | 147 | Good |
| 104 | C089 | 601_C089_Rev | ctggagaatcccggtgccgaggccgctcaattggtcgtagacagctctagcacc gcttaaacgcacgtacgcgctgtccccgcgttttaaccgccaagggattactc cctagtctccaggccgattcggcgatgcgacgatcgTC | 147 | Good |
| 105 | C090 | 601_C090_Rev | ctggagaatcccggtgccgaggccgctcaattggtcgtagacagctctagcacc gcttaaacgcacgtacgcgctgtccccgcgttttaaccgccaagggattactc cctagtctccaggctacggtcgcgaccgtcgaatcgTC | 147 | Good |
| 106 | C091 | 601_C091_Rev | ctggagaatcccggtgccgaggccgctcaattggtcgtagacagctctagcacc gcttaaacgcacgtacgcgctgtccccgcgttttaaccgccaagggattactc cctagtctccaggcatgtcgcgcgacgcgtcaatcgTC | 147 | Good |
| 107 | C092 | 601_C092_Rev | ctggagaatcccggtgccgaggccgctcaattggtcgtagacagctctagcacc gcttaaacgcacgtacgcgctgtccccgcgttttaaccgccaagggattactc cctagtctccaggccggtcgtacgacgcgatatgcgTC | 147 | Good |
| 108 | C093 | 601_C093_Rev | ctggagaatcccggtgccgaggccgctcaattggtcgtagacagctctagcacc gcttaaacgcacgtacgcgctgtccccgcgttttaaccgccaagggattactc cctagtctccaggctacgcgcgacacgtaatcggcgTC | 147 | Good |
| 109 | C094 | 601_C094_Rev | ctggagaatcccggtgccgaggccgctcaattggtcgtagacagctctagcacc gcttaaacgcacgtacgcgctgtccccgcgttttaaccgccaagggattactc cctagtctccaggccgtcgctcgaatatcggtcgcgTC | 147 | Good |
| 110 | C095 | 601_C095_Rev | ctggagaatcccggtgccgaggccgctcaattggtcgtagacagctctagcacc gcttaaacgcacgtacgcgctgtccccgcgttttaaccgccaagggattactc cctagtctccaggcgcgttcgacggattcgtcgcgTC | 147 | Good |
| 111 | C096 | 601_C096_Rev | ctggagaatcccggtgccgaggccgctcaattggtcgtagacagctctagcacc gcttaaacgcacgtacgcgctgtccccgcgttttaaccgccaagggattactc cctagtctccaggccgcgttacgcgcgatagtcgcgTC | 147 | Good |
| 112 | C097 | 601_C097_Rev | ctggagaatcccggtgccgaggccgctcaattggtcgtagacagctctagcacc gcttaaacgcacgtacgcgctgtccccgcgttttaaccgccaagggattactc cctagtctccaggccgcgtaacgcggtcgtatcgcgTC | 147 | Good |
| 113 | C098 | 601_C098_Rev | ctggagaatcccggtgccgaggccgctcaattggtcgtagacagctctagcacc gcttaaacgcacgtacgcgctgtccccgcgttttaaccgccaagggattactc cctagtctccaggctcggtacgcgccggatatcgcgTC | 147 | Good |
| 114 | C099 | 601_C099_Rev | ctggagaatcccggtgccgaggccgctcaattggtcgtagacagctctagcacc gcttaaacgcacgtacgcgctgtccccgcgttttaaccgccaagggattactc cctagtctccaggcccgtcgaacgccgcatatcgcgTC | 147 | Good |
| 115 | C100 | 601_C100_Rev | ctggagaatcccggtgccgaggccgctcaattggtcgtagacagctctagcacc gcttaaacgcacgtacgcgctgtccccgcgttttaaccgccaagggattactc cctagtctccaggcgcgcgtaccgataccgatcgcgTC | 147 | Good |

Nucleotide Sequences - Capital -> Annealing fragment; lowercase -> barcode; bolded lowercase -> nucleosome positioning sequence [601 Widom and Lowary]

BIBLIOGRAPHY

Alewood, P., Alewood, D., Miranda, L., Love, S., Meutermans, W., and Wilson, D. (1997). Rapid in situ neutralization protocols for Boc and Fmoc solid-phase chemistries. Methods Enzymol. 289, 14-29.

Benayoun, B. A., Pollina, E. A., Ucar, D., Mahmoudi, S., Karra, K., Wong, E. D., Devarajan, K., Daugherty, A. C., Kundaje, A. B., Mancini, E., et al. (2014). H3K4me3 Breadth Is Linked to Cell Identity and Transcriptional Consistency. Cell 158, 673-688.

Bernstein, B. E., Meissner, A., and Lander, E. S. (2007). The mammalian epigenome. Cell 128, 669-681.

Bernt K. M. et al. (2011). MLL-rearranged leukemia is dependent on aberrant H3 k79 methylation by DOT1L. Cancer Cell 20, 66-78.

Bin Liu, Yi, J., SV, A., Lan, X., Ma, Y., Huang, T. H., Leone, G., and Jin, V. X. (2013). QChIPat: a quantitative method to identify distinct binding patterns for two biological ChIP-seq samples in different experimental conditions. BMC Genomics 14, S3.

Blankenberg, D., Von Kuster, G., Coraor, N., Ananda, G., Lazarus, R., Mangan, M., Nekrutenko, A., and Taylor, J. (2010). Galaxy: a web-based genome analysis tool for experimentalists. Curr. Protoc. Mol. Biol. Ed. Frederick M Ausubel Al Chapter 19, Unit 19.10.1-21.

Bock, I., Dhayalan, A., Kudithipudi, S., Brandt, O., Rathert, P., and Jeltsch, A. (2011). Detailed specificity analysis of antibodies binding to modified histone tails with peptide arrays. Epigenetics Off. J. DNA Methylation Soc. 6, 256-263.

Brand, M., Rampalli, S., Chaturvedi, C.-P., and Dilworth, F. J. (2008). Analysis of epigenetic modifications of chromatin at specific gene loci by native chromatin immunoprecipitation of nucleosomes isolated using hydroxyapatite chromatography. Nat. Protoc. 3, 398-409.

Chen, Z., Grzybowski, A. T., and Ruthenburg, A. J. (2014). Traceless semisynthesis of a set of histone 3 species bearing specific lysine methylation marks. Chembiochem 15, 2071-2075.

Chi, P., Allis, C. D. & Wang, G. G. Covalent histone modifications—miswritten, misinterpreted and miserased in human cancers. Nat. Rev. Cancer 10, 457-469 (2010).

Daigle, S. R. et al. (2011). Selective killing of mixed lineage leukemia cells by a potent small-molecule DOT1L inhibitor. Cancer Cell 20(1) 53-65.

Dawson, M. A., and Kouzarides, T. (2012). Cancer epigenetics: from mechanism to therapy. Cell 150, 12-27.

Dawson, P. E., Muir, T. W., Clark-Lewis, I., and Kent, S. B. (1994). Synthesis of proteins by native chemical ligation. Science 266, 776-779.

Feinberg, A. P. (2007). Phenotypic plasticity and the epigenetics of human disease. Nature 447, 433-440.

Egelhofer, T. A. et al. An assessment of histone-modification antibody quality. *Nat Struct Mol Biol* 18, 91-93 (2011).

Fuchs, S. M., Krajewski, K., Baker, R. W., Miller, V. L. & Strahl, B. D. Influence of combinatorial histone modifications on antibody and effector protein recognition. *Curr Biol* 21, 53-58 (2011).

Giardine, B., Riemer, C., Hardison, R. C., Burhans, R., Elnitski, L., Shah, P., Zhang, Y., Blankenberg, D., Albert, I., Taylor, J., et al. (2005). Galaxy: a platform for interactive large-scale genome analysis. Genome Res. 15, 1451-1455.

Goecks, J., Nekrutenko, A., Taylor, J., and Galaxy Team (2010). Galaxy: a comprehensive approach for supporting accessible, reproducible, and transparent computational research in the life sciences. Genome Biol. 11, R86.

Guenther, M. G., Levine, S. S., Boyer, L. A., Jaenisch, R., and Young, R. A. (2007). A chromatin landmark and transcription initiation at most promoters in human cells. Cell 130, 77-88.

Hattori, T., Taft, J. M., Swist, K. M., Luo, H., Witt, H., Slattery, M., Koide, A., Ruthenburg, A. J., Krajewski, K., Strahl, B. D., et al. (2013). Recombinant antibodies to histone post-translational modifications. Nat Methods 10, 992-995.

Henikoff, S. (2008). Nucleosome destabilization in the epigenetic regulation of gene expression. Nat. Rev. Genet. 9, 15-26.

Herold, J., Kurtz, S., and Giegerich, R. (2008). Efficient computation of absent words in genomic sequences. BMC Bioinformatics 9, 167.

Jiang, C., and Pugh, B. F. (2009). Nucleosome positioning and gene regulation: advances through genomics. Nat. Rev. Genet. 10, 161-172.

Johnson, E. C. B., and Kent, S. B. H. (2006). Insights into the mechanism and catalysis of the native chemical ligation reaction. J. Am. Chem. Soc. 128, 6640-6646.

Kroon E and Krosl J. (1998). Hoxa9 transforms primary bone marrow cells through specific collaboration with Meisla but not Pbxlb. EMBO 17(13) 3714-3725.

Landt, S. G. et al. ChIP-seq guidelines and practices of the ENCODE and modENCODE consortia. Genome Res 22, 1813-1831 (2012).

Langmead, B., Trapnell, C., Pop, M., and Salzberg, S. L. (2009). Ultrafast and memory-efficient alignment of short DNA sequences to the human genome. Genome Biol. 10, R25.

Lauberth, S. M., Nakayama, T., Wu, X., Ferris, A. L., Tang, Z., Hughes, S. H., and Roeder, R. G. (2013). H3K4me3 Interactions with TAF3 Regulate Preinitiation Complex Assembly and Selective Gene Activation. Cell 152, 1021-1036.

Leroy, G., Dimaggio, P. A., Chan, E. Y., Zee, B. M., Blanco, M. A., Bryant, B., Flaniken, I. Z., Liu, S., Kang, Y., Trojer, P., et al. (2013). A quantitative atlas of histone modification signatures from human cancer cells. Epigenetics Chromatin 6, 20.

Li, B., and Carey, M. (2007). The Role of Chromatin during Transcription. Cell 128, 707-719.

Li, H., Handsaker, B., Wysoker, A., Fennell, T., Ruan, J., Homer, N., Marth, G., Abecasis, G., Durbin, R., and 1000 Genome Project Data Processing Subgroup (2009). The Sequence Alignment/Map format and SAMtools. Bioinforma. Oxf. Engl. 25, 2078-2079.

Liang, K., and Keles, S. (2012). Normalization of ChIP-seq data with control. BMC Bioinformatics 13, 199.

Lowary, P. T., and Widom, J. (1998). New DNA sequence rules for high affinity binding to histone octamer and sequence-directed nucleosome positioning. J. Mol. Biol. 276, 19-42.

Luger, K., Rechsteiner, T. J., and Richmond, T. J. (1999). Preparation of nucleosome core particle from recombinant histones. Methods Enzymol. 304, 3-19.

Marinov, G. K., Kundaje, A., Park, P. J., and Wold, B. J. (2014). Large-scale quality analysis of published ChIP-seq data. G3 (Bethesda) 4, 209-223.

Mikkelsen, T. S., Ku, M., Jaffe, D. B., Issac, B., Lieberman, E., Giannoukos, G., Alvarez, P., Brockman, W., Kim, T.-K., Koche, R. P., et al. (2007). Genome-wide maps of chromatin state in pluripotent and lineage-committed cells. Nature 448, 553-560.

Muthurajan, U. M., Park, Y.-J., Edayathumangalam, R. S., Suto, R. K., Chakravarthy, S., Dyer, P. N., and Luger, K. (2003). Structure and dynamics of nucleosomal DNA. Biopolymers 68, 547-556.

Nady, N., Min, J., Kareta, M. S., Chédin, F., and Arrowsmith, C. H. (2008). A SPOT on the chromatin landscape? Histone peptide arrays as a tool for epigenetic research. Trends Biochem. Sci. 33, 305-313.

Nishikori, S., Hattori, T., Fuchs, S. M., Yasui, N., Wojcik, J., Koide, A., Strahl, B. D., and Koide, S. (2012). Broad ranges of affinity and specificity of anti-histone antibodies revealed by a quantitative peptide immunoprecipitation assay. J Mol Biol 424, 391-399.

Park, P. J. (2009). ChIP-seq: advantages and challenges of a maturing technology. Nat. Rev. Genet. 10, 669-680.

Quinlan, A. R., and Hall, I. M. (2010). BEDTools: a flexible suite of utilities for comparing genomic features. Bioinforma. Oxf. Engl. 26, 841-842.

Ruthenburg, A. J., Li, H., Milne, T. A., Dewell, S., McGinty, R. K., Yuen, M., Ueberheide, B., Dou, Y., Muir, T. W., Patel, D. J., et al. (2011). Recognition of a mononucleosomal histone modification pattern by BPTF via multivalent interactions. Cell 145, 692-706.

Santos-Rosa, H., Schneider, R., Bannister, A. J., Sherriff, J., Bernstein, B. E., Emre, N. C. T., Schreiber, S. L., Mellor, J., and Kouzarides, T. (2002). Active genes are tri-methylated at K4 of histone H3. Nature 419, 407-411.

Schubeler, D. (2004). The histone modification pattern of active genes revealed through genome-wide chromatin analysis of a higher eukaryote. Genes & Development 18, 1263-1271.

Shogren-Knaak, M. A., and Peterson, C. L. (2003). Creating Designer Histones by Native Chemical Ligation. In Methods in Enzymology, C. David Allis and Carl Wu, ed. (Academic Press), pp. 62-76.

Trygve Tollefsbol Epigenetics in Human Disease 2012 Academic Press. Voigt, P., Leroy, G., Drury, W. J., III, Zee, B. M., Son, J., Beck, D. B., Young, N. L., Garcia, B. A., and Reinberg, D. (2012). Asymmetrically modified nucleosomes. Cell 151, 181-193.

Wan, Q., and Danishefsky, S. J. (2007). Free-radical-based, specific desulfurization of cysteine: a powerful advance in the synthesis of polypeptides and glycopolypeptides. Angew. Chem. Int. Ed Engl. 46, 9248-9252.

Young, N. L., Dimaggio, P. A., Plazas-Mayorca, M. D., Baliban, R. C., Floudas, C. A., and Garcia, B. A. (2009). High throughput characterization of combinatorial histone codes. Mol Cell Proteomics 8, 2266-2284.

Zhang, Y., Liu, T., Meyer, C. A., Eeckhoute, J., Johnson, D. S., Bernstein, B. E., Nussbaum, C., Myers, R. M., Brown, M., Li, W., et al. (2008). Model-based analysis of ChIP-Seq (MACS). Genome Biol 9, R137.

Zhang, Z., and Pugh, B. F. (2011). High-resolution genome-wide mapping of the primary structure of chromatin. Cell 144, 175-186.

We claim:

1. A method of determining a density of a first epitope of a core histone at a genomic locus in chromatin of a cell, the method comprising:
   preparing a library of native nucleosomes from the chromatin, wherein the library comprises nucleosomes, each comprising the core histone and a nucleosome nucleotide sequence indicative of its genomic locus of origin;
   adding a standard to the library to create a doped library; wherein the standard comprises a reconstituted nucleosome comprising (i) a standard histone or standard histone fragment having the first epitope and (ii) a standard molecule comprising a barcode molecule, wherein the standard histone or standard histone fragment and the standard molecule form a stable protein-DNA association;
   determining an amount of the core histone at the genomic locus in the doped library;
   determining an amount of the standard in the doped library;
   adding a first affinity reagent to the doped library to capture an amount of native nucleosomes and reconstituted nucleosomes comprising the epitope;
   determining a relative genomic abundance for the first epitope at a genomic locus based on the amount of the captured standard comprising the epitope and the amount of the core histone at the genomic locus in the doped library;
   determining a standard capture efficiency for the epitope based on the amount of captured standard compared to the amount of standard added to the doped library;
   determining the relative genomic abundance of the first epitope of the core histone at the genomic locus based on a first epitope abundance for the core histone and the standard capture efficiency.

2. The method of claim 1, wherein determining the amount of the core histone at the genomic locus in the doped library comprises:
   adding a second affinity reagent to the doped library to recover an amount of nucleosomes comprising a second epitope, wherein the second epitope is an invariant epitope present on the core histone, and
   determining an amount of nucleosome nucleotide sequence in the amount of recovered nucleosomes comprising the second epitope.

3. The method of claim 1, wherein determining the amount of standard in the doped library comprises:
   recovering an amount of reconstituted nucleosome; wherein the reconstituted nucleosome comprises a second epitope, and
   determining an amount of the standard molecule in the amount of recovered reconstituted nucleosomes comprising the second epitope.

4. The method of claim 2, wherein the first affinity reagent is an antibody directed to the first epitope and wherein the second affinity reagent is an antibody directed to the second epitope.

5. The method of claim 1, wherein the first affinity agent is an antibody directed towards the first epitope.

6. The method of claim 1, wherein the barcode molecule encodes a concentration parameter indicative of the concentration of the standard added to the library and wherein standards having at least two differing concentrations are added to the library.

7. The method of claim 6, wherein the plurality of standards further comprises standards comprising reconstituted nucleosomes comprising (i) one or more off-target epitopes and (ii) a standard molecule barcode encoding an off-target epitope identity and concentration parameters indicative to the off-target epitope.

8. The method of claim 1, wherein the first epitope is a post-translational modification or a protein isoform.

9. The method of claim 1, wherein the barcode sequence is a sequence absent in the genome of the cell.

10. The method of claim 1, wherein an abundance of at least one of the nucleosome nucleotide sequence and the standard nucleotide sequence is determined by a method selected from the group consisting of PCR, qPCR, ddPCR, Next Generation Sequencing, hybridization, autoradiography, fluorescent labeling, optical density and the use of intercalating fluorescent probes.

11. The method of claim 1, wherein the first epitope of the core histone comprises at least one post-translational amino acid modification selected from the group consisting of N-acetylation of serine and alanine; phosphorylation of serine, threonine and tyrosine; N-crotonylation, N-acetylation of lysine; N6-methylation, N6,N6-dimethylation, N6,N6,N6-trimethylation of lysine; omega-N-methylation, symmetrical-dimethylation, asymmetrical-dimethylation of arginine; citrullination of arginine; ubiquitinylation of lysine; sumoylation of lysine; O-methylation of serine and threonine, and ADP-ribosylation of arginine, aspartic acid and glutamic acid.

12. The method of claim 1, wherein the standard molecule is a double-stranded polynucleotide comprising a nucleotide sequence selected from the group consisting of a SEQ ID. NOs 1-115.

13. The method of claim 1, wherein the cell is a cell from a patient and wherein the amount of the first epitope at a given locus is indicative of a disease or condition selected from the group consisting of renal cell carcinoma, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesothelioma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, glioma, liposarcoma, infections caused by *Heliocobacter pylori, Listeria monocytogenes, Shigella flexneri, Anaplasma phagocytophilum*, Chlamdophila, Epstein-Barr Virus, herpes, HIV, *Schistosoma haematobium*; Obesity, diabetes, heart disease; autism, fragile X syndrome, ATR-X syndrome, Angelman syndrome, Prader-Willi syndrome, Beckwith Wiedemann syndrome, Rett syndrome, Rubinstein-Taybi syndrome, Coffin-Lowry syndrome Immunodeficiency-centrometric instability-facial anomalies syndrome, α-thalassaemia, leukemia, Huntington's disease, schizophrenia, bipolar disease, aging, dementia, Alzheimer's disease, Parkinson's disease, Cornelia de Langue syndrome, Kabuki syndrome, Sjogren's syndrome, Vitiligo, progressive systemic sclerosis, psoriasis, primary biliary cirrhosis, Crohn's disease and ulcerative colitis, Hashimoto's thyroiditis, Grave's disease, inflammatory bowel disease, atherosclerosis, and cardiac hypertrophy.

14. The method of claim 12, wherein the double-stranded polynucleotide comprises a nucleotide sequence corresponding to SEQ ID. NO 1.

* * * * *

SEQUENCE LISTING

```
<160> NUMBER OF SEQ ID NOS: 115

<210> SEQ ID NO 1
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 1
ggcggccgac gcgatacacc gttcgtcgct ggagaatccc ggtgccgagg ccgctcaatt      60
ggtcgtagac agctctagca ccgcttaaac gcacgtacgc gctgtccccc gcgttttaac    120
cgccaagggg attactccct agtctccagg cacgtgtcag atatatacat cctgtgcgtt    180
cgacggtacg tcgagcggcc gcc                                            203

<210> SEQ ID NO 2
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 2
ggcggcgtat cgcgtcgcgc gtaatcgact ggagaatccc ggtgccgagg ccgctcaatt      60
ggtcgtagac agctctagca ccgcttaaac gcacgtacgc gctgtccccc gcgttttaac    120
cgccaagggg attactccct agtctccagg cacgtgtcag atatatacat cctgtgcgcg    180
acgttacgct cgacgtagcc gcc                                            203

<210> SEQ ID NO 3
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 3
ggcggcaccg atacgcgcgc ggtacgatct ggagaatccc ggtgccgagg ccgctcaatt      60
ggtcgtagac agctctagca ccgcttaaac gcacgtacgc gctgtccccc gcgttttaac    120
cgccaagggg attactccct agtctccagg cacgtgtcag atatatacat cctgttaatc    180
```

```
gacgcgatat cgcgcgtgcc gcc                                            203
```

<210> SEQ ID NO 4
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 4

```
ggcggcatat cgcgcgtcgt atcgcggtct ggagaatccc ggtgccgagg ccgctcaatt     60
ggtcgtagac agctctagca ccgcttaaac gcacgtacgc gctgtccccc gcgttttaac    120
cgccaagggg attactccct agtctccagg cacgtgtcag atatatacat cctgttcgta    180
tcgcgccgcg tattcgggcc gcc                                            203
```

<210> SEQ ID NO 5
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 5

```
ggcggcccgc gcgatattac gcgcgaatct ggagaatccc ggtgccgagg ccgctcaatt     60
ggtcgtagac agctctagca ccgcttaaac gcacgtacgc gctgtccccc gcgttttaac    120
cgccaagggg attactccct agtctccagg cacgtgtcag atatatacat cctgtacgaa    180
cgtcgatcgt cgattcggcc gcc                                            203
```

<210> SEQ ID NO 6
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 6

```
ggcggccgac gaacggttcg tacgcgagct ggagaatccc ggtgccgagg ccgctcaatt     60
ggtcgtagac agctctagca ccgcttaaac gcacgtacgc gctgtccccc gcgttttaac    120
cgccaagggg attactccct agtctccagg cacgtgtcag atatatacat cctgttcgcg    180
tacgaatcgc gtaatcggcc gcc                                            203
```

<210> SEQ ID NO 7
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 7

```
ggcggccgcg taatacgccg cgatacgact ggagaatccc ggtgccgagg ccgctcaatt     60
ggtcgtagac agctctagca ccgcttaaac gcacgtacgc gctgtccccc gcgttttaac    120
cgccaagggg attactccct agtctccagg cacgtgtcag atatatacat cctgtaacgc    180
gtatcgcgcg taacgcggcc gcc                                            203
```

<210> SEQ ID NO 8
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 8

```
ggcggccgta cgacgctcgc gatatccgct ggagaatccc ggtgccgagg ccgctcaatt      60
ggtcgtagac agctctagca ccgcttaaac gcacgtacgc gctgtccccc gcgttttaac    120
cgccaagggg attactccct agtctccagg cacgtgtcag atatatacat cctgtcgacg    180
ttaacgcgtt acgcgtcgcc gcc                                             203
```

<210> SEQ ID NO 9
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 9

```
ggcggcgcgt tcgacgggtc gcgaactact ggagaatccc ggtgccgagg ccgctcaatt      60
ggtcgtagac agctctagca ccgcttaaac gcacgtacgc gctgtccccc gcgttttaac    120
cgccaagggg attactccct agtctccagg cacgtgtcag atatatacat cctgtgtcgc    180
gaactacgtc gttcgacgcc gcc                                             203
```

<210> SEQ ID NO 10
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 10

```
ggcggctacg ctcggactcg cgcgatgact ggagaatccc ggtgccgagg ccgctcaatt      60
ggtcgtagac agctctagca ccgcttaaac gcacgtacgc gctgtccccc gcgttttaac    120
cgccaagggg attactccct agtctccagg cacgtgtcag atatatacat cctgtcgatc    180
gtcgcatcgg tacgctagcc gcc                                             203
```

<210> SEQ ID NO 11
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 11

```
ggcggctatt atgcgcgacc cgcgtacgct ggagaatccc ggtgccgagg ccgctcaatt      60
ggtcgtagac agctctagca ccgcttaaac gcacgtacgc gctgtccccc gcgttttaac    120
cgccaagggg attactccct agtctccagg cacgtgtcag atatatacat cctgtcgtac    180
cgcgatccga cgatcgagcc gcc                                             203
```

<210> SEQ ID NO 12
<211> LENGTH: 203

```
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 12
ggcggctcgc gaccgtacga atttcgcgct ggagaatccc ggtgccgagg ccgctcaatt    60
ggtcgtagac agctctagca ccgcttaaac gcacgtacgc gctgtccccc gcgttttaac   120
cgccaagggg attactccct agtctccagg cacgtgtcag atatatacat cctgtcgcgt   180
caatcgcgat tacgcgagcc gcc                                           203

<210> SEQ ID NO 13
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 13
ggcggctcgt acgaccgcgc gtatcgggct ggagaatccc ggtgccgagg ccgctcaatt    60
ggtcgtagac agctctagca ccgcttaaac gcacgtacgc gctgtccccc gcgttttaac   120
cgccaagggg attactccct agtctccagg cacgtgtcag atatatacat cctgtgcgat   180
cgtacgcgcg acgttaagcc gcc                                           203

<210> SEQ ID NO 14
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 14
ggcggcccgc gcgatattac gcgcgaatct ggagaatccc ggtgccgagg ccgctcaatt    60
ggtcgtagac agctctagca ccgcttaaac gcacgtacgc gctgtccccc gcgttttaac   120
cgccaagggg attactccct agtctccagg cacgtgtcag atatatacat cctgtcgacg   180
ttaacgcgtt acgcgtcgcc gcc                                           203

<210> SEQ ID NO 15
<211> LENGTH: 203
<212> TYPE: DNA
<213> ORGANISM: Artificial Sequence
<220> FEATURE:
<223> OTHER INFORMATION: Nucleosome positioning sequence [601 Widom and
      Lowary]- Annealing  fragment-barcode sequence

<400> SEQUENCE: 15
ggcggccgta cgacgctcgc gatatccgct ggagaatccc ggtgccgagg ccgctcaatt    60
ggtcgtagac agctctagca ccgcttaaac gcacgtacgc gctgtccccc gcgttttaac   120
cgccaagggg attactccct agtctccagg cacgtgtcag atatatacat cctgtacgaa   180
cgtcgatcgt cgattcggcc gcc                                           203

<210> SEQ ID NO 16
<211> LENGTH: 147
<212> TYPE: DNA
<213> ORGANISM: Artificial Sequence
<220> FEATURE:
```

```
<223> OTHER INFORMATION: Nucleosome positioning sequence [601 Widom and
      Lowary]- Annealing fragment-barcode sequence

<400> SEQUENCE: 16
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggctattatg cgcgcgatac gcgtttc                                         147

<210> SEQ ID NO 17
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 17
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggccgcgcat aataatcgcg cgatttc                                         147

<210> SEQ ID NO 18
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 18
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcatatcgc gcgttcgacg ttcgttc                                         147

<210> SEQ ID NO 19
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 19
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcacgcgcg atattatcgc gtcgttc                                         147

<210> SEQ ID NO 20
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 20
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggctcgtcga cgatcgtcga atcgttc                                         147
```

<210> SEQ ID NO 21
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 21
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggctcgtcga ttcgacgcga atcgttc                                         147

<210> SEQ ID NO 22
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 22
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggctacgcga ttcgtcgttt cgcgttc                                         147

<210> SEQ ID NO 23
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 23
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggctatacgc gtcgacgatt cgcgttc                                         147

<210> SEQ ID NO 24
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 24
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggctcgcgta atcgtttcga cgcgttc                                         147

<210> SEQ ID NO 25
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 25

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcttaacgt cgcgcgttcg aacgttc                                       147
```

<210> SEQ ID NO 26
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 26

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgtatta cgcgaatcgc gcgattc                                       147
```

<210> SEQ ID NO 27
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 27

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgatta cgcgtcgcgc gtaattc                                       147
```

<210> SEQ ID NO 28
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 28

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgtttcg tacgcgcgac gtaattc                                       147
```

<210> SEQ ID NO 29
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 29

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgcgta tacgtacgcg cgaattc                                       147
```

<210> SEQ ID NO 30
<211> LENGTH: 147
<212> TYPE: DNA
<213> ORGANISM: Artificial Sequence

```
<220> FEATURE:
<223> OTHER INFORMATION: Nucleosome positioning sequence [601 Widom and
      Lowary]- Annealing fragment-barcode sequence

<400> SEQUENCE: 30
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggccgcgtaa tacgcgcgaa attcgtc                                         147

<210> SEQ ID NO 31
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 31
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcgatagtc gacgttatcg cgtcgtc                                         147

<210> SEQ ID NO 32
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 32
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggccgtacga aacgcgttaa cgtcgtc                                         147

<210> SEQ ID NO 33
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 33
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggccgtcgac tatctcgtcg tatcgtc                                         147

<210> SEQ ID NO 34
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 34
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcttacgcg taccaacgcg tatcgtc                                         147
```

<210> SEQ ID NO 35
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 35

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgaatcg cgtattacgc gatcgtc                                       147
```

<210> SEQ ID NO 36
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 36

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcggtac gctatcgtac gatcgtc                                       147
```

<210> SEQ ID NO 37
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 37

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgacgcg tatacgaatt tcgcgtc                                       147
```

<210> SEQ ID NO 38
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 38

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgacgc gataattacg tcgcgtc                                       147
```

<210> SEQ ID NO 39
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 39

-continued ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgcgcg aatattcgta tcgcgtc                                       147

<210> SEQ ID NO 40
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 40
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctatcgcg tcgagtgata tcgcgtc                                       147

<210> SEQ ID NO 41
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 41
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgcgtaa tcgatacgtt acgcgtc                                       147

<210> SEQ ID NO 42
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 42
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcttacgtc gcgataatcg acgcgtc                                       147

<210> SEQ ID NO 43
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 43
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctattcgc gcgatcgcga ttacgtc                                       147

<210> SEQ ID NO 44
<211> LENGTH: 147
<212> TYPE: DNA

```
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 44
ctggagaatc cggtgccga ggccgctcaa ttggtcgtag acagctctag caccgcttaa     60
acgcacgtac gcgctgtccc ccgcgtttta accgccaagg ggattactcc ctagtctcca    120
ggccgattac gcgaacgatt cgacgtc                                        147

<210> SEQ ID NO 45
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 45
ctggagaatc cggtgccga ggccgctcaa ttggtcgtag acagctctag caccgcttaa     60
acgcacgtac gcgctgtccc ccgcgtttta accgccaagg ggattactcc ctagtctcca    120
ggccgtatac gcgattaacg cgacgtc                                        147

<210> SEQ ID NO 46
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 46
ctggagaatc cggtgccga ggccgctcaa ttggtcgtag acagctctag caccgcttaa     60
acgcacgtac gcgctgtccc ccgcgtttta accgccaagg ggattactcc ctagtctcca    120
ggctagcgta ccgacgacgt taacgtc                                        147

<210> SEQ ID NO 47
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 47
ctggagaatc cggtgccga ggccgctcaa ttggtcgtag acagctctag caccgcttaa     60
acgcacgtac gcgctgtccc ccgcgtttta accgccaagg ggattactcc ctagtctcca    120
ggcatcgtcg acgaacgttc gaacgtc                                        147

<210> SEQ ID NO 48
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 48
ctggagaatc cggtgccga ggccgctcaa ttggtcgtag acagctctag caccgcttaa     60
acgcacgtac gcgctgtccc ccgcgtttta accgccaagg ggattactcc ctagtctcca    120
```

```
ggccgaatcg acgatagttc gcgactc                                        147
```

<210> SEQ ID NO 49
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 49

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgcgacg ttaacgcgat atcactc                                       147
```

<210> SEQ ID NO 50
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 50

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcggtacgc gtaacgcgtc gattatc                                       147
```

<210> SEQ ID NO 51
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 51

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgcgac gtaaattcgc gcgtatc                                       147
```

<210> SEQ ID NO 52
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 52

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgcgtat cggtcgcgta acgtatc                                       147
```

<210> SEQ ID NO 53
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 53

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgacgaa cggtgtcgcg aactatc                                       147
```

<210> SEQ ID NO 54
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 54

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgaacgg tcgtttcgcg cgatatc                                       147
```

<210> SEQ ID NO 55
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 55

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcccgacga tcgtacgacg cgatatc                                       147
```

<210> SEQ ID NO 56
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 56

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgacgta ccgtttacgc gtcgatc                                       147
```

<210> SEQ ID NO 57
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 57

```
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgtacga cgctacgaac gtcgatc                                       147
```

<210> SEQ ID NO 58
<211> LENGTH: 147
```

```
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 58
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggcccgcgcg atattttcgt cgcgatc                                         147

<210> SEQ ID NO 59
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 59
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggctcgcgcg acatcgtaat cgcgatc                                         147

<210> SEQ ID NO 60
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 60
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggccgcgcga tatgattacg cgcgatc                                         147

<210> SEQ ID NO 61
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 61
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggccgcgtat tcggttcgta cgcgatc                                         147

<210> SEQ ID NO 62
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 62
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
```
ggctcgatcg tcggcgatcg tacgatc                                        147

<210> SEQ ID NO 63
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 63
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcacgatcg tcggtcgttc gacgatc                                        147

<210> SEQ ID NO 64
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 64
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggccgacgta tcggcgatac gacgatc                                        147

<210> SEQ ID NO 65
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 65
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcatatcgc gcggtcgtcg aacgatc                                        147

<210> SEQ ID NO 66
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 66
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggccgacgta acggacgcga aacgatc                                        147

<210> SEQ ID NO 67
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 67
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcacgaccg ttcgcgtcgc gttaatc                                       147

<210> SEQ ID NO 68
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 68
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgtatcg gtcgcgatcg cgtaatc                                       147

<210> SEQ ID NO 69
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 69
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcctcgttc gtcgttcgcg cgtaatc                                       147

<210> SEQ ID NO 70
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 70
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcaccgttc gtcgtcgacg cgtaatc                                       147

<210> SEQ ID NO 71
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 71
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctacgtcc gtcgcgacgc gataatc                                       147

<210> SEQ ID NO 72

```
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 72
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcccgttac gtcgtatcgc gcgaatc                                       147

<210> SEQ ID NO 73
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 73
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcacggtac gtcgttacgc gcgaatc                                       147

<210> SEQ ID NO 74
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 74
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcccgatac gtcgtcgcgt acgaatc                                       147

<210> SEQ ID NO 75
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 75
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgcacg atcgcgcgat acgaatc                                       147

<210> SEQ ID NO 76
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 76
ctggagaatc ccggtgccga ggccgctcaa ttggtcgtag acagctctag caccgcttaa    60
```

```
acgcacgtac gcgctgtccc ccgcgtttta accgccaagg ggattactcc ctagtctcca    120
ggctcgccga atcgacgcgt cgaaatc                                        147

<210> SEQ ID NO 77
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 77
ctggagaatc ccggtgccga ggccgctcaa ttggtcgtag acagctctag caccgcttaa    60
acgcacgtac gcgctgtccc ccgcgtttta accgccaagg ggattactcc ctagtctcca    120
ggctatgcgt cgcgtcgcga cgaaatc                                        147

<210> SEQ ID NO 78
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 78
ctggagaatc ccggtgccga ggccgctcaa ttggtcgtag acagctctag caccgcttaa    60
acgcacgtac gcgctgtccc ccgcgtttta accgccaagg ggattactcc ctagtctcca    120
ggccatatcg cgcgcgtatc gcggttc                                        147

<210> SEQ ID NO 79
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 79
ctggagaatc ccggtgccga ggccgctcaa ttggtcgtag acagctctag caccgcttaa    60
acgcacgtac gcgctgtccc ccgcgtttta accgccaagg ggattactcc ctagtctcca    120
ggccgtatag cgcgccgtac gtcgttc                                        147

<210> SEQ ID NO 80
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 80
ctggagaatc ccggtgccga ggccgctcaa ttggtcgtag acagctctag caccgcttaa    60
acgcacgtac gcgctgtccc ccgcgtttta accgccaagg ggattactcc ctagtctcca    120
ggcaccgata cgcgtagcga cgcgttc                                        147

<210> SEQ ID NO 81
<211> LENGTH: 147
<212> TYPE: DNA
<213> ORGANISM: Artificial Sequence
<220> FEATURE:
<223> OTHER INFORMATION: Nucleosome positioning sequence [601 Widom and
```

Lowary]- Annealing fragment-barcode sequence

<400> SEQUENCE: 81
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcccgaata cgcgtcgacg accgttc                                        147

<210> SEQ ID NO 82
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 82
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgtacg accgcggtcg aacgttc                                        147

<210> SEQ ID NO 83
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 83
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcagcgtcg tacgtcgcga cgagttc                                        147

<210> SEQ ID NO 84
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 84
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgcgcta tacgcgtacc gcgattc                                        147

<210> SEQ ID NO 85
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 85
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgaccga tacgcgcggt acgattc                                        147

```
<210> SEQ ID NO 86
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 86
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcttcgagc gacgcggcgt acgattc                                       147

<210> SEQ ID NO 87
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 87
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcgtcgaac gacgcggtcg acgattc                                       147

<210> SEQ ID NO 88
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 88
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcgacgcgt aacgccgcgc gtaattc                                       147

<210> SEQ ID NO 89
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 89
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggctcgacgc gtagcgcgac gcaattc                                       147

<210> SEQ ID NO 90
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 90
ctggagaatc ccggtgccga ggccgctcaa ttggtcgtag acagctctag caccgcttaa    60
```

```
acgcacgtac gcgctgtccc ccgcgtttta accgccaagg ggattactcc ctagtctcca      120
ggccgacgaa cgagtcgtat cgcggtc                                          147

<210> SEQ ID NO 91
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 91
ctggagaatc ccggtgccga ggccgctcaa ttggtcgtag acagctctag caccgcttaa      60
acgcacgtac gcgctgtccc ccgcgtttta accgccaagg ggattactcc ctagtctcca      120
ggccgttacg cgtcttatcg cgcggtc                                          147

<210> SEQ ID NO 92
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 92
ctggagaatc ccggtgccga ggccgctcaa ttggtcgtag acagctctag caccgcttaa      60
acgcacgtac gcgctgtccc ccgcgtttta accgccaagg ggattactcc ctagtctcca      120
ggctaacgtc gcgcattacg cgcggtc                                          147

<210> SEQ ID NO 93
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 93
ctggagaatc ccggtgccga ggccgctcaa ttggtcgtag acagctctag caccgcttaa      60
acgcacgtac gcgctgtccc ccgcgtttta accgccaagg ggattactcc ctagtctcca      120
ggctacgctc ggactatacg cgcggtc                                          147

<210> SEQ ID NO 94
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 94
ctggagaatc ccggtgccga ggccgctcaa ttggtcgtag acagctctag caccgcttaa      60
acgcacgtac gcgctgtccc ccgcgtttta accgccaagg ggattactcc ctagtctcca      120
ggccgtcgtt cgacacgacg tacggtc                                          147

<210> SEQ ID NO 95
<211> LENGTH: 147
<212> TYPE: DNA
<213> ORGANISM: Artificial Sequence
<220> FEATURE:
```

<223> OTHER INFORMATION: Nucleosome positioning sequence [601 Widom and
      Lowary]- Annealing fragment-barcode sequence

<400> SEQUENCE: 95
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcgcgcgac gttacgattc gacggtc                                         147

<210> SEQ ID NO 96
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 96
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggctgtcgcg cgtatacgct cgtcgtc                                         147

<210> SEQ ID NO 97
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 97
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggcgtccgag cgtagtatcg cgtcgtc                                         147

<210> SEQ ID NO 98
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 98
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggctcgcgac cgtagttacg cgtcgtc                                         147

<210> SEQ ID NO 99
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 99
ctggagaatc ccggtgccga ggccgctcaa ttggtcgtag acagctctag caccgcttaa      60
acgcacgtac gcgctgtccc ccgcgtttta accgccaagg ggattactcc ctagtctcca    120
ggccgacgga cgtacgtatc cgtcgtc                                         147

<210> SEQ ID NO 100
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 100
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgcgacg catagcgtta cgtcgtc                                       147

<210> SEQ ID NO 101
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 101
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcctacgcg tcgacgcgtt agtcgtc                                       147

<210> SEQ ID NO 102
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 102
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggcccgacga tcgatcggcg tatcgtc                                       147

<210> SEQ ID NO 103
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 103
ctggagaatc ccggtgccga ggccgctcaa ttggtcgtag acagctctag caccgcttaa    60
acgcacgtac gcgctgtccc ccgcgtttta accgccaagg ggattactcc ctagtctcca   120
ggccgatcgt gcgacgcgac tatcgtc                                       147

<210> SEQ ID NO 104
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 104

```
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggccgattcg gcgatgcgac gatcgtc                                         147
```

<210> SEQ ID NO 105
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 105

```
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggctacggtc gcgaccgtcg aatcgtc                                         147
```

<210> SEQ ID NO 106
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 106

```
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggcatgtcgc gcgacgcgtc aatcgtc                                         147
```

<210> SEQ ID NO 107
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 107

```
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggccggtcgt acgacgcgat atgcgtc                                         147
```

<210> SEQ ID NO 108
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 108

```
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggctacgcgc gacacgtaat cggcgtc                                         147
```

<210> SEQ ID NO 109
<211> LENGTH: 147
<212> TYPE: DNA
<213> ORGANISM: Artificial Sequence

```
<220> FEATURE:
<223> OTHER INFORMATION: Nucleosome positioning sequence [601 Widom and
      Lowary]- Annealing fragment-barcode sequence

<400> SEQUENCE: 109
ctggagaatc cggtgccga ggccgctcaa ttggtcgtag acagctctag caccgcttaa       60
acgcacgtac gcgctgtccc ccgcgtttta accgccaagg ggattactcc ctagtctcca    120
ggccgtcgct cgaatatcgg tcgcgtc                                         147

<210> SEQ ID NO 110
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 110
ctggagaatc cggtgccga ggccgctcaa ttggtcgtag acagctctag caccgcttaa       60
acgcacgtac gcgctgtccc ccgcgtttta accgccaagg ggattactcc ctagtctcca    120
ggcgcgttcg acggattgcg tcgcgtc                                         147

<210> SEQ ID NO 111
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 111
ctggagaatc cggtgccga ggccgctcaa ttggtcgtag acagctctag caccgcttaa       60
acgcacgtac gcgctgtccc ccgcgtttta accgccaagg ggattactcc ctagtctcca    120
ggccgcgtta cgcgcgatag tcgcgtc                                         147

<210> SEQ ID NO 112
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 112
ctggagaatc cggtgccga ggccgctcaa ttggtcgtag acagctctag caccgcttaa       60
acgcacgtac gcgctgtccc ccgcgtttta accgccaagg ggattactcc ctagtctcca    120
ggccgcgtaa cgcggtcgta tcgcgtc                                         147

<210> SEQ ID NO 113
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 113
ctggagaatc cggtgccga ggccgctcaa ttggtcgtag acagctctag caccgcttaa       60
acgcacgtac gcgctgtccc ccgcgtttta accgccaagg ggattactcc ctagtctcca    120
ggctcggtac gcgccggata tcgcgtc                                         147
```

```
<210> SEQ ID NO 114
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 114
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggcccgtcga acgccgcata tcgcgtc                                         147

<210> SEQ ID NO 115
<211> LENGTH: 147
<212> TYPE: DNA
<213> ORGANISM: Artificial Sequence
<220> FEATURE:
<223> OTHER INFORMATION: Nucleosome positioning sequence [601 Widom and
      Lowary]- Annealing fragment-barcode sequence

<400> SEQUENCE: 115
ctggagaatc ccggtgccga ggccgctcaa ttggtcgtag acagctctag caccgcttaa      60
acgcacgtac gcgctgtccc ccgcgtttta accgccaagg ggattactcc ctagtctcca     120
ggcgcgcgta ccgataccga tcgcgtc                                         147
```